(12) United States Patent
Soula et al.

(10) Patent No.: US 9,492,467 B2
(45) Date of Patent: *Nov. 15, 2016

(54) RAPID-ACTING INSULIN FORMULATION COMPRISING AN OLIGOSACCHARIDE

(71) Applicant: ADOCIA, Lyons (FR)

(72) Inventors: Olivier Soula, Meyzieu (FR); Rémi Soula, Lyons (FR); Gérard Soula, Meyzieu (FR)

(73) Assignee: ADOCIA, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/581,239

(22) Filed: Dec. 23, 2014

(65) Prior Publication Data

US 2015/0231160 A1 Aug. 20, 2015

Related U.S. Application Data

(63) Continuation of application No. 13/668,000, filed on Nov. 2, 2012, now abandoned, and a continuation-in-part of application No. 13/287,793, filed on Nov. 2, 2011, now abandoned.

(51) Int. Cl.
*A61K 38/28* (2006.01)
*A61K 31/702* (2006.01)
*C07K 14/62* (2006.01)

(52) U.S. Cl.
CPC ............. *A61K 31/702* (2013.01); *A61K 38/28* (2013.01)

(58) Field of Classification Search
CPC ............................ A61K 38/28; A61K 31/702
See application file for complete search history.

(56) References Cited

U.S. PATENT DOCUMENTS

| | | |
|---|---|---|
| 2,387,201 A | 10/1945 | Weiner |
| 2,847,385 A | 8/1958 | Hiler |
| 4,006,059 A | 2/1977 | Butler |
| 4,011,137 A | 3/1977 | Thompson et al. |
| 4,126,628 A | 11/1978 | Paquet |
| 4,438,029 A | 3/1984 | Erickson et al. |
| 4,472,385 A | 9/1984 | Brange et al. |
| 4,826,818 A | 5/1989 | Mori et al. |
| 5,929,027 A | 7/1999 | Takama et al. |
| 8,241,620 B2 | 8/2012 | Dahri-Correia et al. |
| 2004/0131583 A1 | 7/2004 | Barritault et al. |
| 2004/0234616 A1 | 11/2004 | Sabetsky |
| 2007/0191757 A1 | 8/2007 | Steiner et al. |
| 2007/0235365 A1 | 10/2007 | Pohl et al. |
| 2008/0014250 A1 | 1/2008 | Soula et al. |
| 2008/0039365 A1 | 2/2008 | Steiner et al. |
| 2008/0039368 A1 | 2/2008 | Steiner et al. |
| 2008/0096800 A1 | 4/2008 | Pohl et al. |
| 2008/0234227 A1 | 9/2008 | Soula et al. |
| 2009/0221805 A1 | 9/2009 | Dahri-Correia et al. |
| 2009/0291114 A1 | 11/2009 | Soula et al. |
| 2010/0137456 A1 | 6/2010 | Soula et al. |
| 2010/0166867 A1 | 7/2010 | Soula et al. |
| 2010/0167991 A1 | 7/2010 | Soula et al. |
| 2010/0227795 A1 | 9/2010 | Steiner et al. |
| 2010/0249020 A1 | 9/2010 | Soula et al. |
| 2011/0159068 A1 | 6/2011 | Soula et al. |
| 2011/0172166 A1 | 7/2011 | Charvet et al. |
| 2011/0195025 A1 | 8/2011 | Kett et al. |
| 2011/0195913 A1 | 8/2011 | Charvet et al. |
| 2011/0212901 A1 | 9/2011 | Akiyoshi et al. |
| 2012/0041079 A1 | 2/2012 | Soula et al. |
| 2012/0094902 A1 | 4/2012 | Soula et al. |
| 2012/0178675 A1 | 7/2012 | Pohl et al. |
| 2012/0295833 A1 | 11/2012 | Charvet et al. |
| 2012/0309680 A1 | 12/2012 | Charvet et al. |
| 2013/0231281 A1 | 9/2013 | Soula et al. |
| 2014/0142034 A1 | 5/2014 | Soula et al. |

FOREIGN PATENT DOCUMENTS

| | | |
|---|---|---|
| EP | 0 214 826 A2 | 3/1987 |
| EP | 0 441 563 A2 | 8/1991 |
| EP | 0 648 495 A2 | 4/1995 |
| EP | 0 681 833 A2 | 11/1995 |
| EP | 0 700 683 A1 | 3/1996 |
| EP | 1 623 979 A1 | 2/2006 |
| EP | 2 319 500 A1 | 5/2011 |
| FR | 2 224 164 A1 | 10/1974 |
| FR | 2 914 305 A1 | 10/2008 |
| FR | 2 936 800 A1 | 4/2010 |
| JP | 2007/177182 A | 7/2007 |
| JP | 2007/177185 A | 7/2007 |
| WO | 88/06599 A1 | 9/1988 |
| WO | 91/09617 A1 | 7/1991 |

(Continued)

OTHER PUBLICATIONS

Baudys, Miroslav et al., "Extending Insulin Action in Vivo by Conjugation to Carboxymethyl Dextran," Bioconjugate Chem. 1998, vol. 9, pp. 176-183.
Brange, Jens et al., "Insulin analogs with improved pharmacokinetic profiles," Advanced Drug Delivery Reviews, 1999, vol. 35, pp. 307-335.
Giger, Katie et al., "Suppression of Insulin Aggregation by Heparin," Biomacromolecules, 2008, vol. 9, pp. 2338-2344.
Lou, Xianwen et al., "Simulation of size exclusion chromatography for characterization of supramolecular complex: a theoretical study," Journal of Chromatography A, 2004, vol. 1029, pp. 67-75.
Tschantz, William R. et al., "Substrate Binding Is Required for Release of Product from Mammalian Protein Farnesyltransferase," The Journal of Biological Chemistry, 1997, vol. 272, No. 15, pp. 9989-9993.

(Continued)

*Primary Examiner* — Julie Ha
*Assistant Examiner* — Li Ni Komatsu
(74) *Attorney, Agent, or Firm* — Oliff PLC

(57) ABSTRACT

A composition in aqueous solution, including an insulin and at least one oligosaccharide whose average degree of polymerization is between 3 and 13 and whose polydispersity index PDI is above 1.0, the oligosaccharide having partially substituted carboxyl functional groups, the unsubstituted carboxyl functional groups being salifiable.

32 Claims, 28 Drawing Sheets

(56) References Cited

FOREIGN PATENT DOCUMENTS

| WO | 97/49386 A1 | 12/1997 |
|---|---|---|
| WO | 99/34821 A1 | 7/1999 |
| WO | 02/053190 A2 | 7/2002 |
| WO | 03/000202 A2 | 1/2003 |
| WO | 2004/093833 A2 | 11/2004 |
| WO | 2005/072803 A1 | 8/2005 |
| WO | 2005/089722 A1 | 9/2005 |
| WO | 2007/038773 A1 | 4/2007 |
| WO | 2007/041481 A1 | 4/2007 |
| WO | 2007/116143 A1 | 10/2007 |
| WO | 2007/121256 A2 | 10/2007 |
| WO | 2008/038111 A1 | 4/2008 |
| WO | 2008/084237 A2 | 7/2008 |
| WO | 2008/124522 A2 | 10/2008 |
| WO | 2008/152106 A1 | 12/2008 |
| WO | 2009/048945 A1 | 4/2009 |
| WO | 2009/048959 A1 | 4/2009 |
| WO | 2009/127940 A1 | 10/2009 |
| WO | 2010/018324 A1 | 2/2010 |
| WO | 2010/028055 A1 | 3/2010 |
| WO | 2010/041119 A1 | 4/2010 |
| WO | 2010/041138 A2 | 4/2010 |
| WO | 2010/053140 A1 | 5/2010 |
| WO | 2010/058106 A1 | 5/2010 |
| WO | 2010/102020 A1 | 9/2010 |
| WO | 2010/122385 A1 | 10/2010 |
| WO | 2010/149772 A1 | 12/2010 |
| WO | 2011/077405 A1 | 6/2011 |
| WO | 2011/098962 A2 | 8/2011 |
| WO | 2012/153070 A1 | 11/2012 |
| WO | 2012/153071 A2 | 11/2012 |
| WO | 2013/064787 A1 | 5/2013 |

OTHER PUBLICATIONS

Oct. 14, 2009 Search Report issued in French Patent Application No. 723351.
Jul. 12, 2010 Written Opinion issued in International Patent Application No. PCT/IB2010/000711 mailed.
Jul. 12, 2010 Search Report issued in International Patent Application No. PCT/IB2010/000711.
Sep. 19, 2012 Office Action issued in U.S. Appl. No. 12/662,036.
Arranz et al., "Water-insoluble dextrans by grafting, 3a) Reaction of dextran with butyl isocyanate. Chemical hydrolysis," Makromol. Chem., vol. 188, pp. 2831-2838, 1987.
Carpino et al., "Efficiency in Peptide Coupling: 1-Hydroxy-7-azabenzotriazole vs 3,4-Dihydro-3-hydroxy-4-oxo-1,2,3-benzotriazine," Journal of Organic Chemistry, vol. 60, pp. 3561-3564, 1995.
Caulfield et al., "The Permeability of Glomerular Capillaries to Graded Dextrans," The Journal of Cell Biology, vol. 63, pp. 883-903, 1974.
Chang et al., "Permselectivity of the glomerular capillary wall: III. Restricted transport of polyanions," Kidney International, vol. 8, pp. 212-218, 1975.
Demitras et al, Inorganic Chemistry, Prentice-Hall International Inc., 1972, enclosed pp. 1-5.
Engelmann et al., "Preparation of Starch Carbamates in Homogeneous Phase using Different Mixing Conditions," Starch/Stärke, 2001, pp. 560-569, vol. 53, WILEY-VCH Verlag GmbH.
Larsen, "Dextran prodrugs—structure and stability in relation to therapeutic activity," Advanced Drug Delivery Reviews, 1989, pp. 103-154, vol. 3, Elsevier.
Ouari et al., "Synthesis of a Glycolipidic Amphiphilic Nitrone as a New Spin Trap," J. Org. Chem., 1999, pp. 3554-3556, vol. 64, American Chemical Society (with 10 pages of supporting information).
Shen et al., "Synthesis and Characterization of Cellulose Carbamates Having α-Amino Acid Moieties," Polymer Bulletin, 2005, pp. 317-322, vol. 55.
Tsai et al., "Synthesis of Amino Acid Ester Isocyanates: Methyl (S)-2-Isocyanato-3-Phenylpropanoate [Benzenepropanoic acid, α-isocyanato-, methyl ester, (S)]," Organic Syntheses Coll., vol. 10, p. 544, 2004; vol. 78, p. 220, 2002.
Won, "Synthesis of heterobifunctional poly(ethylene glycol) containing an acryloyl group at one end and an isocyanate group at the other end," Polymer Bulletin, 2004, pp. 109-115, vol. 52.
Definition of Phenylalanine, from Croatian English Chemistry Dictionary & Glossary (http://glossary.periodni.com/glossary.php?en=phenylalanine, enclosed, pp. 1-2, Accessed Jan. 17, 2013.
May 3, 2012 French Search Report issued in French Patent Application No. 1158885.
Feb. 22, 2013 Office Action issued in U.S. Appl. No. 12/662,036.
Feb. 28, 2013 Office Action issued in U.S. Appl. No. 13/468,799.
U.S. Appl. No. 12/662,036 to Soula et al., filed Mar. 29, 2010.
U.S. Appl. No. 13/287,793 to Soula et al., filed Nov. 2, 2011.
U.S. Appl. No. 13/468,799 to Charvet et al., filed May 10, 2012.
U.S. Appl. No. 13/468,849 to Charvet et al., filed Jul. 11, 2012.
Heinze et al.; "Functional Polymers Based on Dextran;" Adv. Polym. Sci.; 2006; pp. 199-291; vol. 205; Springer-Verlag Berlin Heidelberg.
May 28, 2014 Office Action issued in U.S. Appl. No. 13/468,849.
Jul. 24, 2013 Office Action issued in U.S. Appl. No. 12/662,036.
R. Janowski, et al., "Two Polymorphs of a Covalent Complex Between Papain and a Diazomethylketone Inhibitor," J. Peptide Res. 64, 2004, pp. 141-150.
Apr. 2, 2013 International Search Report issued in PCR/FR2012/052543.
Jun. 25, 2014 Office Action issued in U.S. Appl. No. 13/668,000.
Definition of derivative and analog, from http://cancerweb.ncl.ac.uk/omd/about.html, pp. 1-5, accessed Jul. 7, 2005.
Polymer Molecular Weight Distribution and Definitions of MW Averages, from www.agilent.com/chem, pp. 1-4, Jun. 10, 2011.
Dec. 12, 2011 French Search Report issued in French Patent Application No. 1154039.
Rudd, Pauline M. et al., "Glycoforms modify the dynamic stability and functional activity of an enzyme." Biochemistry (1994) 33 p. 17-22.
Memo, Myriad-Mayo guidance, Mar. 2014.
Bovine ribonuclease b sequence (protein data bank, accession No. 1RBJ__, upload Oct. 10, 2012).
Solomons, T.W. Graham; Organic Chemistry, 4th editon, (1988) ISBN 0-471-83659-1, p. 751.
Heinze, Thomas et al.; "Functional Polymers based on dextran." Adv. Polym. Sci. (2006) 205 p. 199-291.
Roussel et al., "Monolayer lipid membrane-forming dissymmetrical bolaamphiphiles derived from alginate oligosaccharides;" Chem. Communication; 2006; pp. 3622-3624.
Watanabe et al., "Synthesis of lipid A type carboxymethyl derivatives with ether chains instead of ester chains and their LPS-antagonistic "activities;" Carbohydrate" Research; 2003; pp. 47-54; vol. 338.
Song et al., "6-o-Amino-2-o-carboxymethyl Glucopyranoside as Novel Glycoaminoxy Acid Building Block for the Construction of Oligosaccharide Mimetics;" Synthesis; 2011; pp. 2761-2766; No. 17.
Tareq et al., "Ieodoglucomides A and B from a Marine-Derived Bacterium Bacillus lichentiformis;" Organic Letters; 2012; pp. 1464-1467; vol. 14, No. 6.
Smoot et al., "Oligosaccharide Synthesis From Conventional Methods to Modern Expeditious Strategies;" Advances in Carbohydrate Chemistry and Biochemistry; 2009; pp. 161-251; vol. 62.
Lindhorst; "O-Glycoside Synthesis," Essentials of Carbohydrate Chemistry and Biochemistry; 2007; pp. 157-208.
Pal et al., "Molecular mechanism of physical gelation of hydrocarbons by fatty acid amides of natural amino acids," Tetrahedron; 2007; pp. 7334-7348; vol. 63.
Bhaskar et al., "The Selective Silylation of d-Mannitol Assisted by Phenylboronic Acid and the Solid State and Solution Structures of the Intermediate 1,6-bis(silyl) bis(phenylboronates);" Journal of Carbohydrate Chemistry; 2003; pp. 867-879; vol. 22, 9.
Edwards et al., "Dispiroketals in Synthesis (Part 18): Regioselective and Enantioselective Protection of Symmetric Polyol Substrates

(56) References Cited

OTHER PUBLICATIONS

Using an Enantiopure (2S,2S)-Dimethyl-bis-dihydropyran;" Synlett; 1995; pp. 898-900; vol. 9.
Ruiz-Pena et al., "Physico-chemical studies of molecular interactions between non-ionic surfactants and bovine serum albumin;" Colloids and Surfaces B: Biointerfaces: 2010: pp. 282-289; vol. 75.
Sawardeker, Jawahar S. et al., "Quantitative determination of monosaccharides as their alditol acetates by gas liquid chromatography." Anal. Chem. (1965) 37 (12) p. 1602-1604.
Class notes for physical chemistry form the Univesity of Washington http://www.ocean.washington.edu/courses/oc400/Lecture_Notes/CHPT6.pdf, Oct. 2004.
Granger, Elisabeth et al., "Simplified syntheses of complex multifunctional nanomaterials." Chem. Communication (2008) 4792-4794.
Oct. 15, 2014 Office Action issued in U.S. Appl. No. 14/079,437.
May 21, 2015 Office Action issued in U.S. Appl. No. 14/079,437.
Huus et al., "Thermal Dissociation and Unfolding of Insulin," Biochemistry: 2005; pp. 11171-11177; vol. 44.
Uversky et al., "Predication of the Association State of Insulin Using Spectral Parameters;" Journal of Pharmaceutical Sciences; Apr. 2003; pp. 847-858; vol. 92, No. 4.
U.S. Appl. No. 14/079,437, filed Nov. 13, 2013 in the name of Soula et al.
U.S. Appl. No. 14/079,516, filed Nov. 13, 2013 in the name of Soula et al.
Dec. 18, 2015 Office Action issued in U.S. Appl. No. 14/079,437.
Wagner, Herman L., "The Mark-Houwink-Sakurada equation for the viscosity of linear polyethylene." J. Phys. Chem. Ref. Data (1985) 14(2) p. 611-617.
Wayne, Richard P., Principles and applications of photochemistry (1988) ISBN 0-19-855234-3.
Shimadzu scientific publication SC-AP-GC-0138, downloaded Dec. 1, 2015.
Dec. 21, 2015 Office Action issued in U.S. Appl. No. 14/079,516.
Jun. 10, 2016 Office Action Issued in U.S. Appl. No. 14/079,516.

RAPID-ACTING INSULIN FORMULATION COMPRISING AN OLIGOSACCHARIDE

CROSS-REFERENCE TO RELATED APPLICATION

This application is a continuation application of application Ser. No. 13/668,000 filed Nov. 2, 2012, which in turn is a continuation-in-part application of application Ser. No. 13/287,793 filed Nov. 2, 2011. The disclosures of the prior applications are hereby incorporated by reference herein in their entireties.

BACKGROUND

The present invention relates to a rapid-acting insulin formulation.

Since the production of insulin by genetic engineering, at the beginning of the 1980s, diabetic patients have had the benefit of human insulin for their treatment. This product has greatly improved this therapy since the immunological risks associated with the use of nonhuman, in particular porcine, insulin are eliminated. However, human insulin injected subcutaneously only has a hypoglycemic effect after 60 minutes, which means that diabetic patients treated with human insulin must carry out the injection 30 minutes before a meal.

One of the problems that need to be solved for improving the health and comfort of diabetic patients is to make insulin formulations available that provide a hypoglycemic response more quickly than that of human insulin and if possible approaching the physiological response of a healthy individual. The endogenous insulin secretion in a healthy individual is triggered immediately by an increase in glycemia. The objective is to reduce as much as possible the delay between injection of insulin and the start of a meal.

It is now accepted that making such formulations available is useful so that management of the disease is optimal.

Genetic engineering has made it possible to provide a response with the development of rapid-acting insulin analogs. These insulins are modified on one or two amino acids so that they are absorbed more rapidly in the blood compartment after a subcutaneous injection. These insulins lispro (Humalog®, Lilly), aspart (Novolog®, Novo) and glulisine (Apidra®, SanofiAventis) are stable insulin solutions with a more rapid hypoglycemic response than that of human insulin. Therefore patients treated with these rapid-acting insulin analogs can proceed with insulin injection just 15 minutes before a meal.

The principle of the rapid-acting insulin analogs is to form hexamers with a concentration of 100 IU/mL for ensuring stability of the insulin in the commercial product while promoting very rapid dissociation of these hexamers into monomers after subcutaneous injection in order to obtain rapid action.

Human insulin as formulated in its commercial form does not allow a hypoglycemic response to be obtained that is close in terms of kinetics of the physiological response generated by the start of a meal (increase in glycemia), because at the concentration of use (100 IU/mL), in the presence of zinc and other excipients such as phenol or m-cresol, it assembles in the hexamer form whereas it is active in the form of monomer and of dimer. Human insulin is prepared in the form of hexamers so that it is stable for nearly 2 years at 4° C., since in the form of monomers it has a very strong tendency to aggregate and then to form fibrils, which causes it to lose its activity. Moreover, in this aggregated form, it presents an immunological risk for the patient.

Dissociation of the hexamers into dimers and of the dimers into monomers delays its action by nearly 20 minutes compared with a rapid-acting insulin analog (Brange J., et al., Advanced Drug Delivery Review, 35, 1999, 307-335).

The kinetics of passage of insulin analogs into the blood, and their kinetics of reduction of glycemia, are not optimal and there is a real need for a formulation having an even shorter time of action in order to approach the kinetics of endogenous insulin secretion in healthy persons.

The company Biodel has proposed a solution to this problem with a formulation of human insulin comprising EDTA and citric acid as described in patent application US200839365. EDTA, by its capacity for complexing zinc atoms, and citric acid, by its interactions with the cationic zones present on the surface of insulin, are described as destabilizing the hexameric form of insulin and thus reducing its time of action.

However, such a formulation notably has the drawback of dissociating the hexameric form of insulin, which is the only stable form able to meet the stability requirements of the pharmaceutical regulations.

PCT application WO2010/122385, in the name of the applicant, is also known; this describes formulations of human insulin or insulin analog for solving the various problems mentioned above by adding a substituted polysaccharide comprising carboxyl groups.

However, the requirements arising from chronic and intensive use or even pediatric use of such formulations lead a person skilled in the art to try to use excipients whose molecular weight and size are as small as possible to facilitate their elimination.

The aim of reducing the size of the polysaccharides has led a person skilled in the art to consider oligosaccharides, but owing to their reduced size these do not have the same properties as the polysaccharides, since there is loss of the polymer effect, as is demonstrated in the comparative examples in the experimental section, see notably the tests for insulin dissolution at the isoelectric point and the tests of interaction with a model protein such as albumin.

SUMMARY

Despite these discouraging results, the applicant has succeeded in developing formulations capable of accelerating insulin by using oligomers alone or in combination with a polyanionic compound.

Surprisingly, besides the fact that addition of this polyanionic compound makes it possible to improve the inadequate performance of the oligosaccharides, it makes it possible to obtain performance equal to that obtained with a polysaccharide, even when the oligosaccharide alone or the polyanionic compound alone has no effect.

Moreover, as in the case when polysaccharides are used, the hexameric nature of the insulin is not affected, therefore the stability of the formulations is not affected.

The present invention can solve the various problems described above since it notably makes it possible to produce a formulation of insulin, human or analog, capable after administration of accelerating the passage of human insulin or of insulin analogs into the blood and of reducing glycemia more rapidly compared with the corresponding commercial insulin products.

It also allows a significant reduction in the time for the start of action of a formulation of rapid-acting insulin analog.

The invention consists of a composition, in aqueous solution, comprising insulin and at least one oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

DETAILED DESCRIPTION

Figure 1:
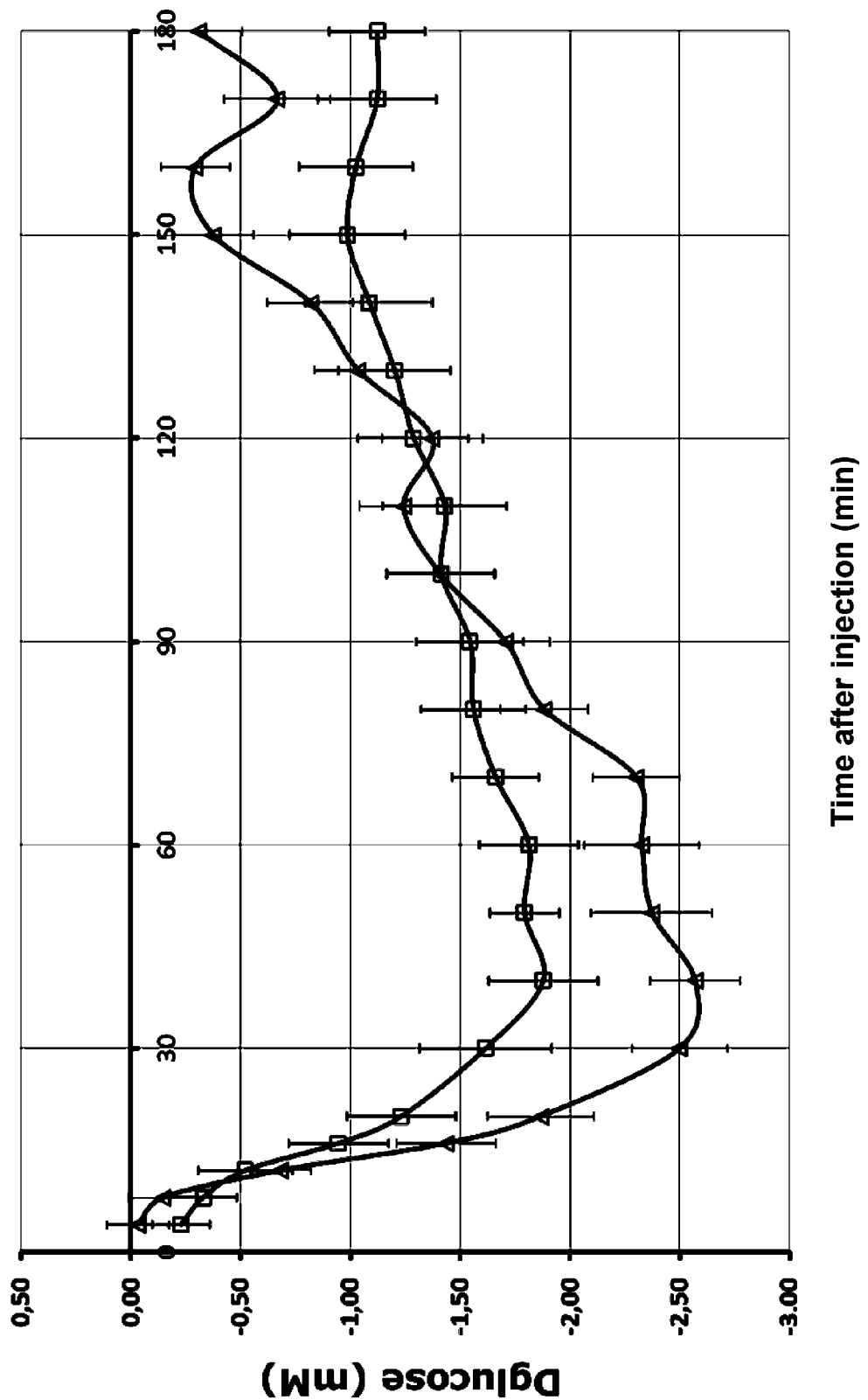
FIG. 1: the curves show that the formulation of human insulin (curve plotted with squares corresponding to example B3, Tmin glucose=61±31 min) has a slower action than the commercial formulation of insulin aspart (curve plotted with triangles corresponding to example B1, Tmin glucose=44±13 min).

In one embodiment, the average degree of polymerization is below 10.

In one embodiment, the polydispersity index PDI is between 1.1 and 2.0.

In one embodiment, the polydispersity index PDI is between 1.2 and 1.8.

The degree of polymerization DP means the average number of repeating units (monomers) per polymer chain. It is calculated by dividing the number-average molecular weight by the average molecular weight of the repeating unit.

The number-average molecular weight (Mn) means the arithmetic mean of the weights of each of the polymer chains. Thus, for a number ni of chains i of molecular weight Mi, we have Mn=(ΣiniMi)/(Σini).

The weight-average molecular weight (Mw) is obtained from Mw=(ΣiniMi2)/(ΣiniMi), ni being the number of polymer chains i of molecular weight Mi.

The polymers can also be characterized by the distribution of chain lengths, also called polydispersity index (PDI), and is equal to Mw divided by Mn.

In one embodiment, the composition further comprises a polyanionic compound.

In one embodiment, the insulin is human insulin.

Human insulin means an insulin obtained by synthesis or recombination whose peptide sequence is the sequence of human insulin, including the allelic variations and the homologs.

In one embodiment, the insulin is an insulin analog.

Insulin analog means a recombinant insulin whose primary sequence contains at least one modification relative to the primary sequence of human insulin.

In one embodiment the insulin analog is selected from the group comprising insulin lispro (Humalog®), insulin aspart (Novolog®, Novorapid®) and insulin glulisine (Apidra®).

In one embodiment, the insulin analog is insulin lispro (Humalog®).

In one embodiment, the insulin analog is insulin aspart (Novolog®, Novorapid®).

In one embodiment, the insulin analog is insulin glulisine (Apidra®).

The invention also relates to a pharmaceutical formulation of insulin comprising a composition according to the invention.

In one embodiment, it relates to a pharmaceutical formulation characterized in that the concentration of insulin is between 240 and 3000 µM (40 to 500 IU/mL).

In one embodiment, it relates to a pharmaceutical formulation characterized in that the concentration of insulin is between 600 and 1200 µM (100 to 200 IU/mL).

In one embodiment, it relates to a pharmaceutical formulation characterized in that the concentration of insulin is 600 µM (100 IU/mL).

In one embodiment, it relates to a pharmaceutical formulation characterized in that the concentration of insulin is 600 µM (100 IU/mL).

In one embodiment, it relates to a pharmaceutical formulation characterized in that the concentration of insulin is 1200 µM (200 IU/mL).

In one embodiment, the invention relates to a complex between human insulin and an oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

It also relates to the use of this complex for preparing formulations of human insulin that make it possible, after administration, to accelerate the passage of human insulin into the blood and reduce glycemia more rapidly relative to an oligosaccharide-free formulation alone or mixed with a polyanionic compound.

In one embodiment, the invention relates to a complex between an insulin analog and an oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

It also relates to the use of this complex for preparing formulations of insulin analog that make it possible, after administration, to accelerate the passage of the insulin analog into the blood and reduce glycemia more rapidly relative to an oligosaccharide-free formulation alone or mixed with a polyanionic compound.

In one embodiment, the invention relates to the use of at least one oligosaccharide whose average degree of polymerization is between 3 and 13 and whose polydispersity index PDI is above 1.0, alone or mixed with a polyanionic compound, for preparing a pharmaceutical formulation of insulin that makes it possible, after administration, to accelerate the passage of insulin into the blood and reduce glycemia more rapidly relative to an oligosaccharide-free formulation alone or mixed with a polyanionic compound.

In one embodiment, the invention relates to the use of at least one oligosaccharide whose average degree of polymerization is between 3 and 13 and whose polydispersity index PDI is above 1.0, alone or mixed with a polyanionic compound, for preparing a formulation of insulin analog that makes it possible, after administration, to accelerate the passage of the insulin analog into the blood and reduce glycemia more rapidly relative to an oligosaccharide-free formulation alone or mixed with a polyanionic compound.

It is known by a person skilled in the art that the onset of action of insulins is dependent upon the concentration of insulin. Only values for the onset of action of formulations at 100 IU/mL are documented.

The "regular" formulations of human insulin on the market at a concentration of 600 µM (100 IU/mL) have a onset of action between 50 and 90 minutes and an offset of action of about 360 to 420 minutes in humans. The time to reach the peak insulin concentration in the blood is between 90 and 180 minutes in humans.

The formulations of rapid-acting insulin analogs on the market at a concentration of 600 µM (100 IU/mL) have a onset of action between 30 and 60 minutes and an offset of action of about 240-300 minutes in humans. The time to reach the peak insulin concentration in the blood is between 50 and 90 minutes in humans.

The invention also relates to a method of preparing a formulation of human insulin having an insulin concentration between 240 and 3000 µM (40 and 500 IU/mL), whose onset of action in humans is less than that of the reference formulation at the same insulin concentration in the absence of oligosaccharide, characterized in that it comprises a step of adding, to said formulation, at least one oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

In one embodiment, said method further comprises a step of adding at least one polyanionic compound to said formulation.

The invention also relates to a method of preparing a formulation of human insulin having an insulin concentration between 600 and 1200 µM (100 and 200 IU/mL), whose onset of action in humans is less than 60 minutes, characterized in that it comprises a step of adding, to said formulation, at least one oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

In one embodiment, said method further comprises a step of adding at least one polyanionic compound to said formulation.

The invention also relates to a method of preparing a formulation of human insulin having an insulin concentration of 600 µM (100 IU/mL), whose onset of action in humans is less than 60 minutes, characterized in that it comprises a step of adding, to said formulation, at least one oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

In one embodiment, said method further comprises a step of adding at least one polyanionic compound to said formulation.

The invention also relates to a method of preparing a formulation of human insulin having an insulin concentration of 1200 µM (200 IU/mL), whose onset of action in humans is at least 10% lower than that of the formulation of human insulin in the absence of oligosaccharide, characterized in that it comprises a step of adding, to said formulation, at least one oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

In one embodiment, said method further comprises a step of adding at least one polyanionic compound to said formulation.

The invention consists of preparing a so-called rapid-acting formulation of human insulin, characterized in that it comprises a step of adding, to said formulation, at least one oligosaccharide whose average degree of polymerization is between 3 and 13 and whose polydispersity index PDI is above 1.0, having partially substituted carboxyl functional groups.

In one embodiment, said method further comprises a step of adding at least one polyanionic compound to said formulation.

The invention also relates to a method of preparing a formulation of human insulin at a concentration of 600 µM (100 IU/mL) whose onset of action in humans is less than 60 minutes, preferably less than 45 minutes, and more preferably less than 30 minutes, characterized in that it comprises a step of adding, to said formulation, at least one oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

In one embodiment, said method further comprises a step of adding at least one polyanionic compound to said formulation.

The invention also relates to a method of preparing a formulation of insulin analog having an insulin concentration between 240 and 3000 µM (40 and 500 IU/mL), whose onset of action in humans is less than that of the reference formulation at the same insulin concentration in the absence of oligosaccharide, characterized in that it comprises a step of adding, to said formulation, at least one oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

In one embodiment, said method further comprises a step of adding at least one polyanionic compound to said formulation The invention also relates to a method of preparing a formulation of insulin analog having an insulin concentration between 600 and 1200 µM (100 and 200 IU/mL), whose onset of action in humans is less than that of the reference formulation at the same concentration of insulin analog in the absence of oligosaccharide, characterized in that it comprises a step of adding, to said formulation, at least one oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

In one embodiment, said method further comprises a step of adding at least one polyanionic compound to said formulation.

The invention also relates to a method of preparing a formulation of insulin analog having an insulin concentration of 600 µmol/L (100 IU/mL), whose onset of action in humans is less than that of the reference formulation at the same concentration of insulin analog in the absence of oligosaccharide, characterized in that it comprises a step of adding, to said formulation, at least one oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

The invention also relates to a method of preparing a formulation of insulin analog having an insulin concentration of 1200 µM (200 IU/mL), whose onset of action in humans is at least 10% lower than that of the formulation of insulin analog in the absence of oligosaccharide, characterized in that it comprises a step of adding, to said formulation, at least one oligosaccharide whose average degree of polymerization is between 3 and 13, said oligosaccharide having partially substituted carboxyl functional groups, the unsubstituted carboxyl functional groups being salifiable.

In one embodiment, said method further comprises a step of adding at least one polyanionic compound to said formulation.

The invention also relates to a method of preparing a formulation of insulin analog having an insulin concentration of 1200 µmol/L (200 IU/mL), whose delay in action in humans is less than 30 minutes, characterized in that it comprises a step of adding, to said formulation, at least one oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

In one embodiment, said method further comprises a step of adding at least one polyanionic compound to said formulation.

The invention consists of preparing a so-called very-rapid-acting formulation of insulin analog, characterized in that it comprises a step of adding, to said formulation, at least one oligosaccharide whose average degree of polymerization is between 3 and 13 and whose polydispersity index PDI is above 1.0, said oligosaccharide having partially substituted carboxyl functional groups, the unsubstituted carboxyl functional groups being salifiable.

In one embodiment, said method further comprises a step of adding at least one polyanionic compound to said formulation.

In one embodiment, the insulin analog is selected from the group comprising insulin lispro (Humalog®), insulin aspart (Novolog®, Novorapid®) and insulin glulisine (Apidra®).

In one embodiment, the insulin analog is insulin lispro (Humalog®).

In one embodiment, the insulin analog is insulin aspart (Novolog®, Novorapid®).

In one embodiment, the insulin analog is insulin glulisine (Apidra®).

In one embodiment, the oligosaccharide is a functionalized oligosaccharide whose average degree of polymerization is between 3 and 13 and whose polydispersity index PDI is above 1.0 and which has carboxyl functional groups.

Said oligosaccharide is selected from the functionalized oligosaccharides whose degree of polymerization is between 3 and 13 and whose polydispersity index PDI is above 1.0, consisting for the most part of glycosidic bonds of the (1,6) type.

In one embodiment, the oligosaccharide consisting for the most part of glycosidic bonds of the (1,6) type is a functionalized dextran having carboxyl functional groups.

In one embodiment, the average degree of polymerization is below 10.

Said oligosaccharide is functionalized with at least one phenylalanine derivative, designated Phe:

said phenylalanine derivative being grafted or bonded to the oligosaccharide by coupling with an acid function, said acid function being an acid function borne by a linkage R bonded to the oligosaccharide by a function F, said function F resulting from coupling between the linker arm R and an —OH function of the oligosaccharide, F being either an ester function, carbamate or ether function, R being a chain comprising between 1 and 15 carbons, which is optionally branched and/or unsaturated, comprising one or more heteroatoms, such as O, N and/or S, and having at least one carboxyl function, Phe being a residue of a phenylalanine derivative, of absolute configuration L or D, the product of coupling between the amine function of phenylalanine and at least one acid function carried by the group R and/or an acid function carried by the oligosaccharide bearing carboxyl functional groups.

In one embodiment, the functionalized oligosaccharide is selected from the oligosaccharides whose average degree of polymerization is between 3 and 13 and whose polydispersity index PDI is above 1.0, of the following general formula I:

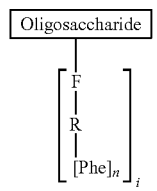

Formula I the oligosaccharide is a dextran,

F results from coupling between the linker arm R and an —OH function of the oligosaccharide and being either an ester, carbamate or ether function, R is a chain comprising between 1 and 15 carbons, optionally branched and/or unsaturated, comprising one or more heteroatoms, such as O, N and/or S, and having at least one carboxyl function, Phe is a residue of a phenylalanine derivative, of absolute configuration L or D, produced from coupling between the amine function of the phenylalanine derivative and at least one acid function carried by group R prior to attachment to Phe, n represents the mole fraction of the R substituted with Phe and is between 0.1 and 0.9, preferably between 0.2 and 0.8, more preferably between 0.3 and 0.7, more preferably between 0.3 and 0.5;

i represents the average mole fraction of the groups F—R-[Phe]$_n$ borne per saccharide unit and is between 0.5 and 3.0, preferably between 1.0 and 2.5, preferably between 1.2 and 2.2, preferably between 1.4 and 2.0;

when R is not substituted with Phe, the acid or acids of group R are carboxylates with an alkaline cation, preferably such as $Na^+$, $K^+$, $Ca^{2+}$ or $Mg^{2+}$.

In one embodiment, n, which represents the degree of substitution of the R substituted with Phe, is between 0.1 and 0.9, preferably between 0.2 and 0.8, preferably between 0.3 and 0.7, more preferably between 0.3 and 0.5.

In one embodiment, n, which represents the mole fraction of the R substituted with Phe, is between 0.2 and 0.9, preferably between 0.3 and 0.8, preferably between 0.3 and 0.6, more preferably between 0.3 and 0.5.

In one embodiment, F is an ether function.
In one embodiment, F is a carbamate function.
In one embodiment, F is an ester function.
In one embodiment R is a chain comprising 1 carbon.
In one embodiment, the oligosaccharide according to the invention is characterized in that the group R before optional attachment to Phe, is selected from the following groups:

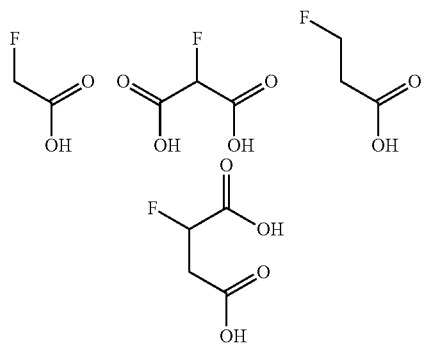

or their salts of alkaline cations selected from the group consisting of $Na^+$ or $K^+$.

In one embodiment, the oligosaccharide according to the invention is characterized in that the group R before optional attachment to Phe, is derived from citric acid.

In one embodiment, the oligosaccharide according to the invention is characterized in that the group R before optional attachment to Phe, is derived from malic acid.

In one embodiment, the oligosaccharide according to the invention is characterized in that the phenylalanine derivative is selected from the group consisting of phenylalanine, alpha-methyl-phenylalanine, 3,4-dihydroxyphenylalanine, tyrosine, alpha-methyl-tyrosine, O-methyl-tyrosine, alpha-phenylglycine, 4-hydroxyphenylglycine, 3,5-dihydroxyphenylglycine and their salts of alkaline cations and phenylalaninol, phenylalaninamide, ethyl benzyl amine, said derivatives being of absolute configuration L or D.

In one embodiment, the oligosaccharide according to the invention is characterized in that the phenylalanine derivative is selected from the group consisting of phenylalanine and its salts of alkaline cations, phenylalaninol, phenylalaninamide, ethyl benzyl amine, said derivatives being of absolute configuration L or D.

In one embodiment, the oligosaccharide according to the invention is characterized in that the phenylalanine derivative is selected from the group consisting of phenylalanine, alpha-methyl-phenylalanine, 3,4-dihydroxyphenylalanine tyrosine, alpha-methyl-tyrosine, O-methyl-tyrosine, alpha-phenylglycine, 4-hydroxyphenylglycine, 3,5-dihydroxyphenylglycine and their salts of alkaline cations, said derivatives being of absolute configuration L or D.

In one embodiment, the oligosaccharide according to the invention is characterized in that the derivative of phenylalanine is phenylalanine and its salts of alkaline cations, said derivative being of absolute configuration L or D.

In one embodiment, the oligosaccharide according to the invention is characterized in that the derivative of phenylalanine is alpha-methyl-phenylalanine and its salts of alkaline cations, said derivative being of absolute configuration L or D.

In one embodiment, the oligosaccharide according to the invention is characterized in that the derivative of phenylalanine is 3,4-dihydroxyphenylalanine and its salts of alkaline cations, said derivative being of absolute configuration L or D.

In one embodiment, the oligosaccharide according to the invention is characterized in that the derivative of phenylalanine is tyrosine and its salts of alkaline cations, said derivative being of absolute configuration L or D.

In one embodiment, the oligosaccharide according to the invention is characterized in that the derivative of phenylalanine is alpha-methyl-tyrosine and its salts of alkaline cations, said derivative being of absolute configuration L or D.

In one embodiment, the oligosaccharide according to the invention is characterized in that the derivative of phenylalanine is O-methyl-tyrosine and its salts of alkaline cations, said derivative being of absolute configuration L or D.

In one embodiment, the oligosaccharide according to the invention is characterized in that the derivative of phenylalanine is alpha-phenylglycine and its salts of alkaline cations, said derivative being of absolute configuration L or D.

In one embodiment, the oligosaccharide according to the invention is characterized in that the derivative of phenylalanine is 4-hydroxyphenylglycine and its salts of alkaline cations, said derivative being of absolute configuration L or D.

In one embodiment, the oligosaccharide according to the invention is characterized in that the derivative of phenylalanine is 3,5-dihydroxyphenylglycine and its salts of alkaline cations, said derivative being of absolute configuration L or D.

In one embodiment, the derivatives of phenylalanine are in the form of a racemic mixture.

In one embodiment, the derivatives of phenylalanine are in the form of isolated isomers of absolute configuration D.

In one embodiment, the derivatives of phenylalanine are in the form of isolated isomers of absolute configuration L.

In one embodiment, the oligosaccharide is selected from oligodextrans.

In one embodiment, the oligodextran has a number-average molecular weight below 3500 g/mol.

In one embodiment, the oligodextran has a number-average molecular weight below 2500 g/mol.

In one embodiment, the oligosaccharide has an average degree of polymerization between 3 and 13.

In one embodiment at least 50% of the population of oligosaccharide has an average degree of polymerization below 10.

In one embodiment, the oligosaccharide has an average degree of polymerization between 3 and 10.

In one embodiment, the oligosaccharide has an average degree of polymerization between 3 and 6.

In one embodiment, the polydispersity index PDI is between 1.1 and 2.0.

In one embodiment, the polydispersity index PDI is between 1.2 and 1.8.

In one embodiment, the polyanionic compound is an anionic molecule.

According to the invention, the anionic molecules are selected from the group consisting of citric acid, aspartic acid, glutamic acid, malic acid, tartaric acid, succinic acid, adipic acid, oxalic acid, triphosphate and their salts of $Na^+$, $K^+$, $Ca^{2+}$ or $Mg^{2+}$.

In one embodiment, the anionic molecule is citric acid and its salts of $Na^+$, $K^+$, $Ca^{2+}$ or $Mg^{2+}$.

In one embodiment, the polyanionic compound is an anionic polymer.

According to the invention, the anionic polymers are selected from the group consisting of dextranmethylcarboxylic acid, polyglutamic acid, polyaspartic acid, PAA (polyacrylic acid), alginate, hyaluronic acid, polymers based on glucuronic acid or based on galacturonic acid and their salts of $Na^+$, $K^+$, $Ca^{2+}$ or $Mg^{2+}$.

In one embodiment, the anionic polymer has a number-average molecular weight between 1 kg/mol and 15 kg/mol.

In one embodiment, the anionic polymer has a number-average molecular weight between 1 kg/mol and 10 kg/mol.

In one embodiment, the anionic polymer has a number-average molecular weight between 1 kg/mol and 8 kg/mol.

In one embodiment, the anionic polymer is a synthetic dextran bearing carboxyl functions.

In one embodiment, the synthetic dextran bearing carboxyl functions is selected from the group consisting of carboxymethyldextran, carboxyethyldextran, dextran succinic acid, dextran 2-butanedioic acid, dextran propanedioic acid.

In one embodiment, the anionic polymer is a carboxymethyldextran whose mole fraction with respect to carboxymethyl is between 0.5 and 3.

In one embodiment, the anionic polymer is a carboxymethyldextran whose mole fraction with respect to carboxymethyl is between 0.5 and 2.5.

In one embodiment, the anionic polymer is a carboxymethyldextran whose mole fraction with respect to carboxymethyl is between 1.0 and 2.0.

In one embodiment, the anionic polymer is a dextran succinic acid whose mole fraction of succinic acid is between 0.5 and 3.

In one embodiment, the anionic polymer is a dextran succinic acid whose mole fraction of succinic acid is between 0.5 and 2.5.

In one embodiment, the anionic polymer is a dextran succinic acid whose mole fraction of succinic acid is between 1.0 and 2.0.

In one embodiment, the anionic polymer is a dextran 2-butanedioic acid whose mole fraction of 2-butanedioic acid is between 0.2 and 3.

In one embodiment, the anionic polymer is a dextran 2-butanedioic acid whose mole fraction of 2-butanedioic acid is between 0.5 and 2.5.

In one embodiment, the anionic polymer is a dextran 2-butanedioic acid whose mole fraction of 2-butanedioic acid is between 0.7 and 2.0.

In one embodiment, the anionic polymer is a dextran propanedioic acid whose mole fraction of propanedioic acid is between 0.2 and 3.

In one embodiment, the anionic polymer is a dextran propanedioic acid whose mole fraction of propanedioic acid is between 0.5 and 2.5.

In one embodiment, the anionic polymer is a dextran propanedioic acid whose mole fraction of propanedioic acid is between 0.7 and 2.0.

In one embodiment, the polyanionic compound is selected from anionic compounds consisting of a skeleton formed from a discrete number p between 1 and 8 ($1 \leq p \leq 8$) of identical or different saccharide units, bonded by identical or different glycosidic bonds and naturally bearing carboxyl groups or substituted with carboxyl groups, and salts thereof.

In one embodiment, the polyanionic compound consisting of a skeleton formed from a discrete number of saccharide units is obtained from a disaccharide compound selected from the group comprising trehalose, maltose, lactose, sucrose, cellobiose, isomaltose, maltitol and isomaltitol.

In one embodiment, the polyanionic compound consisting of a skeleton formed from a discrete number of saccharide units is obtained from a compound consisting of a skeleton formed from a discrete number of saccharide units selected from the group comprising maltotriose, maltotetraose, maltopentaose, maltohexaose, maltoheptaose, maltooactose and isomaltotriose.

In one embodiment, the polyanionic compound consisting of a skeleton formed from a discrete number of saccharide units is selected from the group comprising carboxymethylmaltotriose, carboxymethylmaltotetraose, carboxymethylmaltopentaose, carboxymethylmaltohexaose, carboxymethylmaltoheptaose, carboxymethylmaltooctaose and carboxymethylisomaltotriose.

In one embodiment, the insulin is a recombinant human insulin as described in the European Pharmacopoeia and the United States Pharmacopeia.

In one embodiment, the insulin is an insulin analog selected from the group comprising insulin lispro (Humalog®), insulin aspart (Novolog®, Novorapid®) and insulin glulisine (Apidra®).

In one embodiment, the oligosaccharide/insulin molar ratios are between 0.2 and 7.

In one embodiment, the molar ratios are between 0.3 and 5.

In one embodiment, the molar ratios are between 0.6 and 4.

In one embodiment, the molar ratios are between 1 and 3.

In one embodiment, the molar ratios are between 1.2 and 3.

In one embodiment, the molar ratio is equal to 1.

In one embodiment, the molar ratio is equal to 2.

In one embodiment, the oligosaccharide/insulin weight ratios are between 0.4 and 10.

In one embodiment, the weight ratios are between 0.6 and 7.

In one embodiment, the weight ratios are between 1.2 and 5.

In one embodiment, the weight ratios are between 1.6 and 4.

In one embodiment, the weight ratios are between 2 and 4.

In one embodiment, the concentration of functionalized oligosaccharides is between 1.4 and 35 mg/mL.

In one embodiment, the concentration of functionalized oligosaccharides is between 2.1 and 25 mg/mL.

In one embodiment, the concentration of functionalized oligosaccharides is between 4.2 and 18 mg/mL.

In one embodiment, the concentration of functionalized oligosaccharides is between 5.6 and 14 mg/mL.

In one embodiment, the concentration of functionalized oligosaccharides is between 7 and 14 mg/mL.

In one embodiment, the concentration of anionic compound is between 5 and 150 mM. In one embodiment, the concentration of polyanionic compound is between 5 and 100 mM.

In one embodiment, the concentration of polyanionic compound is between 5 and 75 mM.

In one embodiment, the concentration of polyanionic compound is between 5 and 50 mM.

In one embodiment, the concentration of polyanionic compound is between 5 and 30 mM.

In one embodiment, the concentration of polyanionic compound is between 5 and 20 mM.

In one embodiment, the concentration of polyanionic compound is between 5 and 10 mM.

In one embodiment, the concentration of polyanionic compound is between 1 and 30 mg/mL.

In one embodiment, the concentration of polyanionic compound is between 1.5 and 25 mg/mL.

In one embodiment, the concentration of polyanionic compound is between 2 and 25 mg/mL.

In one embodiment, the concentration of polyanionic compound is between 2 and 10 mg/mL.

In one embodiment, the concentration of polyanionic compound is between 2 and 8 mg/mL.

In one embodiment, the oligosaccharide is sodium dextranmethylcarboxylate modified with sodium phenylalaninate, $q=4$, $i=1.1$, $n=0.45$.

In one embodiment, the oligosaccharide is sodium dextranmethylcarboxylate modified with sodium phenylalaninate, $q=4$, $i=1.65$, $n=0.39$.

In one embodiment, the oligosaccharide is sodium dextranmethylcarboxylate modified with sodium phenylalaninate, $q=4$, $i=2.0$, $n=0.5$.

In one embodiment, the oligosaccharide is sodium dextranmethylcarboxylate modified with sodium phenylalaninate, $q=4$, $i=0.7$, $n=0.57$.

In one embodiment, the oligosaccharide is sodium dextranmethylcarboxylate modified with sodium phenylalaninate, $q=4$, $i=1.72$, $n=0.42$.

In one embodiment, the oligosaccharide is sodium dextranmethylcarboxylate modified with sodium phenylalaninate, $q=4$, $i=2.1$, $n=0.6$.

In one embodiment, the polyanionic compound is sodium dextranmethylcarboxylate.

In one embodiment, the polyanionic compound is sodium citrate.

The composition can moreover be produced by simple mixing of an aqueous solution of human insulin or insulin analog and of an aqueous solution of oligosaccharide.

In one embodiment, the composition can be produced by simple mixing of an aqueous solution of human insulin or insulin analog, of an aqueous solution of oligosaccharide and of polyanionic compound in solution or in the form of lyophilizate.

In one embodiment, the composition can be produced by simple mixing of an aqueous solution of human insulin or insulin analog and of oligosaccharide in the form of lyophilizate.

In one embodiment, the composition can be produced by simple mixing of an aqueous solution of human insulin or insulin analog, of oligosaccharide in the form of lyophilizate and of polyanionic compound in solution or in the form of lyophilizate.

Preferably this composition is in the form of an injectable solution.

In one embodiment, the concentration of human insulin or insulin analog is between 240 and 3000 µM (40 to 500 IU/mL).

In one embodiment, the concentration of human insulin or insulin analog is between 600 and 1200 µM (100 to 200 IU/mL).

In one embodiment, the concentration of human insulin or insulin analog is 600 µM (100 IU/mL).

In one embodiment, the concentration of human insulin or insulin analog is 1200 µM (200 IU/mL).

In one embodiment, the insulin concentration of the solutions is 600 µM or 100 IU/mL.

In one embodiment, the concentration of human insulin or insulin analog of 600 μM can be reduced by simple dilution, in particular for pediatric applications.

The invention also relates to a pharmaceutical formulation according to the invention, characterized in that it is obtained by drying and/or lyophilization.

In the case of local and systemic release, the methods of administration envisaged are by the intravenous, subcutaneous, intradermal or intramuscular route.

The transdermal, oral, nasal, vaginal, ocular, buccal, and pulmonary routes of administration are also envisaged.

The invention also relates to the use of a composition according to the invention for the formulation of a solution of human insulin or insulin analog with a concentration of 100 IU/mL intended for implantable or portable insulin pumps.

The invention also relates to the use of a composition according to the invention for the formulation of a solution of human insulin or insulin analog with a concentration of 200 IU/mL intended for implantable or portable insulin pumps.

EXAMPLES

AA. Oligosaccharides According to the Invention

| OLIGO-SACCHARIDES | SUBSTITUENTS —F—R —F—R-Phe | USUAL NAME |
|---|---|---|
| Oligosaccharide 1 q: 4 i: 1.1 n: 0.45 | 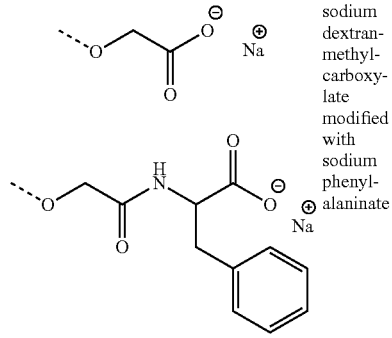 | sodium dextran-methyl-carboxy-late modified with sodium phenyl-alaninate |
| Oligosaccharide 2 q: 4 i: 1.65 n: 0.39 | | |
| Oligosaccharide 3 q: 4 i: 2.0 n: 0.5 | | |
| Oligosaccharide 4 q: 4 i: 0.7 n: 0.57 | | |
| Oligosaccharide 5 q: 4 i: 1.72 n: 0.42 | | |
| Oligosaccharide 6 q: 4 i: 2.1 n: 0.6 | | |

AA1. Oligosaccharide 1: Sodium Dextranmethylcarboxylate Functionalized with Sodium L-Phenylalaninate 40 g (0.74 mol of hydroxyl functions) of dextran with weight-average molecular weight 1 kg/mol (DP=4, Pharmacosmos) and 115 g (0.99 mol) of sodium chloroacetate are dissolved in water at 65° C. 123 mL of 10 N NaOH (1.23 mol) is added dropwise to this solution and then the mixture is heated to 65° C. The mixture is then diluted with water, neutralized with acetic acid and then purified by ultrafiltration on PES membrane of 1 kDa against water. The oligosaccharide concentration of the final solution is determined by dry extraction, then an acid/base assay in a water/acetone mixture 50/50 (v/v) is carried out to determine the average mole fraction of sodium methylcarboxylates.

According to dry extraction: [oligosaccharide]=37.6 mg/g

According to the acid base assay, the average mole fraction of sodium methylcarboxylates is 1.1.

The solution of sodium dextranmethylcarboxylate is acidified on a Purolite resin (anionic) to obtain dextranmethylcarboxylic acid, which is then lyophilized for 18 hours.

12 g of dextranmethylcarboxylic acid (61 mmol of methylcarboxylic acid functions) is dissolved in DMF and then cooled to 0° C. A mixture of ethyl phenylalaninate, hydrochloride salt (Bachem) (6 g, 26 mmol) in DMF is prepared. 2.6 g of triethylamine (26 mmol) is added to this mixture. A solution of NMM (6.1 g, 61 mmol) and of EtOCOCl (6.6 g, 61 mmol) is then added to the mixture at 0° C. The solution of ethyl phenylalaninate is then added and the mixture is stirred at 10° C. An aqueous solution of imidazole is added and then the mixture is heated to 30° C. The medium is diluted with water and then the solution obtained is purified by ultrafiltration on PES membrane of 1 kDa against 0.1 N NaOH, 0.9% NaCl and water. The oligosaccharide concentration of the final solution is determined by dry extraction. A sample of solution is lyophilized and analyzed by $^1$H NMR in $D_2O$ to determine the average mole fraction of sodium methylcarboxylates functionalized with sodium L-phenylalaninate.

According to dry extraction: [Oligosaccharide 1]=20.8 mg/g

According to $^1$H NMR: the average mole fraction of sodium methylcarboxylates functionalized with sodium L-phenylalaninate is 0.45.

AA2. Oligosaccharide 2: Sodium Dextranmethylcarboxylate Functionalized with Sodium L-Phenylalaninate 40 g (0.74 mol of hydroxyl functions) of dextran with weight-average molecular weight 1 kg/mol (DP=4, Pharmacosmos) and 144 g (1.23 mol) of sodium chloroacetate are dissolved in water at 65° C. 123 mL of 10 N NaOH (1.23 mol) is added dropwise to this solution and then the mixture is heated at 65° C. for 90 minutes. 86.3 g (0.74 mol) of sodium chloroacetate is then added to the reaction mixture as well as 74.1 mL of 10N NaOH (0.74 mol) dropwise and heating is continued at 65° C. The mixture is then diluted with water, neutralized with acetic acid and then purified by ultrafiltration on PES membrane of 1 kDa against water. The oligosaccharide concentration of the final solution is determined by dry extraction, then an acid/base assay in a water/acetone mixture 50/50 (v/v) is carried out to determine the average mole fraction of sodium methylcarboxylates.

According to dry extraction: [oligosaccharide]=34.4 mg/g

According to the acid/base assay, the average mole fraction of sodium methylcarboxylates is 1.65.

By a method similar to that used for preparing oligosaccharide 1, a sodium dextranmethylcarboxylate functionalized with sodium L-phenylalaninate is obtained.

According to dry extraction: [Oligosaccharide 2]=20.4 mg/g

According to $^1$H NMR: average mole fraction of sodium methylcarboxylates functionalized with sodium L-phenylalaninate is 0.39.

AA3. Oligosaccharide 3: Sodium Dextranmethylcarboxylate Functionalized with Sodium L-Phenylalaninate Oligosaccharide 3 is a sodium dextranmethylcarboxylate functionalized with sodium L-phenylalaninate obtained from a dextran of weight-average molecular weight 1 kg/mol (DP=4, Pharmacosmos) according to the method described in patent application FR 07/02316. The average mole fraction of sodium methylcarboxylates optionally functionalized with sodium L-phenylalaninate is 2.0. The average mole fraction of sodium methylcarboxylates functionalized with sodium L-phenylalaninate is 0.5.

This oligosaccharide is referenced polysaccharide 13 in the priority document.

AA4. Oligosaccharide 4: Sodium Dextranmethylcarboxylate Functionalized with Sodium L-Phenylalaninate 120 g (2.22 mol of hydroxyl functions) of dextran with weight-average molecular weight 1 kg/mol (DP=4, Pharmacosmos) and 151 g (1.3 mol) of sodium chloroacetate are dissolved in water at 65° C. 370 mL of 10 N NaOH (3.7 mol) is added dropwise to this solution and then the mixture is heated to 65° C. The mixture is then diluted with water, neutralized with acetic acid and then purified by ultrafiltration on PES membrane of 1 kDa against water. The oligosaccharide concentration of the final solution is determined by dry extraction, then an acid/base assay in a water/acetone mixture 50/50 (v/v) is carried out to determine the average mole fraction of sodium methylcarboxylates.

According to dry extraction: [oligosaccharide]=22.1 mg/g

According to the acid/base assay, the average mole fraction of sodium methylcarboxylates is 0.7.

By a method similar to that used for preparing oligosaccharide 1, a sodium dextranmethylcarboxylate functionalized with sodium L-phenylalaninate is obtained.

According to dry extraction: [Oligosaccharide 4]=20.4 mg/g

According to $^1$H NMR: the average mole fraction of sodium methylcarboxylates functionalized with sodium L-phenylalaninate is 0.57.

AA5. Oligosaccharide 5: Sodium Dextranmethylcarboxylate Functionalized with Sodium L-Phenylalaninate Oligosaccharide 5 is a sodium dextranmethylcarboxylate functionalized with sodium L-phenylalaninate obtained from a dextran of weight-average molecular weight 1 kg/mol (DP=4, Pharmacosmos) according to the method described in patent application FR 07/02316. The average mole fraction of sodium methylcarboxylates optionally functionalized with sodium L-phenylalaninate is 1.72. The average mole fraction of sodium methylcarboxylates functionalized with sodium L-phenylalaninate is 0.42.

This oligosaccharide is referenced polysaccharide 12 in the priority document.

AA6. Oligosaccharide 6: Sodium Dextranmethylcarboxylate Functionalized with Sodium L-Phenylalaninate Oligosaccharide 6 is a sodium dextranmethylcarboxylate functionalized with sodium L-phenylalaninate obtained from a dextran of weight-average molecular weight 1 kg/mol (DP=4, Pharmacosmos) according to the method described in patent application FR 07/02316. The average mole fraction of sodium methylcarboxylates optionally and functionalized with sodium L-phenylalaninate is 2.1. The average mole fraction of sodium methylcarboxylates functionalized with sodium L-phenylalaninate is 0.6.

AB Polysaccharides, Counterexamples

AB1. Polysaccharide 1: Sodium Dextranmethylcarboxylate Functionalized with Sodium L-Phenylalaninate Polysaccharide 1 is a sodium dextranmethylcarboxylate functionalized with sodium L-phenylalaninate obtained from a dextran of weight-average molecular weight 10 kg/mol (DP=39, Pharmacosmos) according to the method described in patent application FR 07/02316. The average mole fraction of sodium methylcarboxylates is 1.06. The average mole fraction of sodium methylcarboxylates functionalized with sodium L-phenylalaninate is 0.43.

This polysaccharide corresponds to polysaccharide 1 of application FR0901478.

AB2. Polysaccharide 2: Sodium Dextranmethylcarboxylate Functionalized with Sodium L-Phenylalaninate Polysaccharide 2 is a sodium dextranmethylcarboxylate functionalized with sodium L-phenylalaninate obtained from a dextran with weight-average molecular weight 5 kg/mol (DP=19, Pharmacosmos) according to the method described in patent application FR 07/02316. The average mole fraction of sodium methylcarboxylates is 1.65. The average mole fraction of sodium methylcarboxylates functionalized with sodium L-phenylalaninate is 0.39.

AB3. Polysaccharide 3: Sodium Dextranmethylcarboxylate Functionalized with Sodium L-Phenylalaninate Polysaccharide 3 is a sodium dextranmethylcarboxylate functionalized with sodium L-phenylalaninate obtained from a dextran with weight-average molecular weight 5 kg/mol (DP=19, Pharmacosmos) according to the method described in patent application FR 07/02316. The average mole fraction of sodium methylcarboxylates is 1.10. The average mole fraction of sodium methylcarboxylates functionalized with sodium L-phenylalaninate is 0.41.

AB4. Polysaccharide 4: Sodium Dextranmethylcarboxylate Functionalized with Sodium L-Phenylalaninate Polysaccharide 4 is a sodium dextranmethylcarboxylate functionalized with sodium L-phenylalaninate obtained from a dextran with weight-average molecular weight 10 kg/mol (DP=39, Pharmacosmos) according to the method described in patent application FR 07/02316. The average mole fraction of sodium methylcarboxylates is 1.65. The average mole fraction of sodium methylcarboxylates functionalized with sodium L-phenylalaninate is 0.39.

AB5. Polysaccharide 5: Sodium Dextranmethylcarboxylate Functionalized with Sodium L-Phenylalaninate Polysaccharide 5 is a sodium dextranmethylcarboxylate functionalized with sodium L-phenylalaninate obtained from a dextran with weight-average molecular weight 5 kg/mol (DP=19, Pharmacosmos) according to the method described in patent application FR 07/02316. The average mole fraction of sodium methylcarboxylates is 1.10. The average mole fraction of sodium methylcarboxylates functionalized with sodium L-phenylalaninate is 0.59.

AC Polyanionic Compounds

AC1. Polyanionic Compound 1: Sodium Dextranmethylcarboxylate 40 g (0.74 mol of hydroxyl functions) of dextran with weight-average molecular weight 1 kg/mol (DP=4, Pharmacosmos) and 144 g (1.23 mol) of sodium chloroacetate are dissolved in water at 60° C. 123 mL of 10 N NaOH (1.23 mol) is added dropwise to this solution and then the mixture is heated at 60° C. for 90 minutes. 86.3 g (0.74 mol) of sodium chloroacetate is then added to the reaction mixture as well as 74.1 mL of 10 N NaOH (0.74 mol) dropwise. After 1 h of heating, the mixture is diluted with water, neutralized with acetic acid and then purified by ultrafiltration on PES membrane of 1 kDa against water. The oligosaccharide concentration of the final solution is determined by dry extraction, then an acid/base assay in a water/acetone mixture 50/50 (v/v) is carried out to determine the average mole fraction of sodium methylcarboxylates.

According to dry extraction: [Polyanionic compound 1]=34.4 mg/g

According to the acid/base assay, the average mole fraction of sodium methylcarboxylates is 1.65.

AC2. Polyanionic Compound 2: Sodium Maltotriosemethylcarboxylate

Polyanionic compound 2 is a sodium maltotriosemethylcarboxylate obtained by a method similar to that used for preparing polyanionic compound 1. The average mole fraction of sodium methylcarboxylates is 1.65.

B. Preparation of the Solutions

B1. Solution of Rapid-Acting Insulin Analog Novolog® at 100 IU/mL.

This solution is a commercial solution of insulin aspart from Novo Nordisk sold under the name Novologe. This product is a rapid-acting insulin aspart analog.

B2. Solution of Rapid-Acting Insulin Analog Humalog® at 100 IU/mL.

This solution is a commercial solution of insulin lispro from Eli Lilly sold under the name Humalog®. This product is a rapid-acting insulin analog.

B3. Solution of Regular Human Insulin Actrapid® at 100 IU/mL.

This solution is a commercial solution of human insulin from Novo Nordisk sold under the name Actrapid®. This product is a regular human insulin.

B4. Preparation of the Solutions of Excipients

Preparation of a solution of sodium citrate at 1.188 M.

A solution of sodium citrate is obtained by dissolving 9.0811 g of sodium citrate (30.9 mmol) in 25 mL of water in a graduated flask. The pH is adjusted to exactly 7.4 by adding 1 mL of 1 M HCl. The solution is filtered on 0.22 µm.

Preparation of a Solution of m-Cresol 130 mM.

A solution of m-cresol is obtained by dissolving 14.114 g of m-cresol (130 mmol) in 986.4 mL of water in a 1 L graduated flask.

Preparation of a solution of m-cresol and glycerin (96.6 mM m-cresol and 566 mM glycerin).

73.3 g of the solution of m-cresol at 130 mM is added to 5.26 g of glycerin and then diluted by adding 22.25 g of water. The resultant solution of m-cresol and glycerin is homogenized for 30 minutes and then filtered on a 0.22 µm membrane.

Preparation of a Solution of Tween 20 at 32.7 mM.

A solution of Tween 20 is obtained by dissolving 2.0079 g of Tween 20 (1.636 mmol) in 50 mL of water in a graduated flask. The solution is filtered on a 0.22 µm membrane.

B5. Preparation of a Solution of Human Insulin at 500 IU/mL.

15 g of water is added to 563.6 mg of human insulin, then the pH is lowered to acid pH by adding 5.98 g of 0.1 N HCl. After complete dissolution of the insulin at acid pH, the solution is neutralized to pH 7.2 by adding 8.3 mL of 0.1 N NaOH. The concentration is then adjusted to 500 IU/mL by adding 0.76 g of water. The solution is finally filtered on a 0.22 µm membrane.

B6. Preparation of a Solution of Human Insulin at 100 IU/mL in the Presence of Oligosaccharide 2 and Polyanionic Compound 1.

For a final volume of 100 mL of formulation with a weight ratio [oligosaccharide 2]/[polyanionic compound 1]/[insulin] of 2/2/1, the various reagents are mixed in the quantities stated below:

| | |
|---|---|
| Human insulin at 500 IU/mL | 20 mL |
| Solution of polyanionic compound 1 at 34.74 mg/mL | 21.01 mL |
| Solution 96.6 mM m-cresol/566 mM glycerin | 30 mL |
| Water | 28.99 mL |
| Lyophilizate of oligosaccharide 2 | 730 mg |

The final pH is 7.4±0.4.

This clear solution is filtered on a 0.22 µm membrane and is then stored at +4° C.

B7. Preparation of a Solution of Human Insulin at 100 IU/mL in the Presence of Oligosaccharide 2 and 9.3 mM of Citrate.

For a final volume of 100 mL of formulation with a weight ratio [oligosaccharide 2]/[insulin] of 2, the various reagents are mixed in the quantities stated below:

| | |
|---|---|
| Human insulin at 500 IU/mL | 20 mL |
| Solution of oligosaccharide 2 at 36.01 mg/mL | 20.27 mL |
| Solution 96.6 mM m-cresol/566 mM glycerin | 30 mL |
| Water | 28.95 mL |
| Solution of sodium citrate at 1.188M | 785 µL |

The final pH is 7.4±0.4.

This clear solution is filtered on a 0.22 µm membrane and is then stored at +4° C.

B8. Preparation of a Solution of Insulin Lispro at 100 IU/mL in the Presence of Oligosaccharide 6.

For a final volume of 100 mL of formulation, with a weight ratio [oligosaccharide 6]/[insulin lispro] of 2.0, the various reagents are added in the quantities specified below:

| | |
|---|---|
| Oligosaccharide 6 in lyophilized form | 730 mg |
| Commercial solution of Humalog at 100 IU/ml | 100 mL |

The final pH is adjusted to 7.4±0.4.

The clear solution is filtered on a 0.22 µm membrane and stored at 4° C.

B9. Preparation of a Solution of Insulin Lispro at 100 IU/mL in the Presence of Oligosaccharide 2 and 9.3 mM of Citrate.

For a final volume of 100 mL of formulation, with a weight ratio [oligosaccharide 2]/[insulin lispro] of 2.0 and a concentration of 9.3 mM of citrate, the various reagents are added in the quantities specified below:

| | |
|---|---|
| Oligosaccharide 2 in lyophilized form | 730 mg |
| Commercial solution of Humalog at 100 IU/ml | 100 mL |
| Solution of sodium citrate at 1.188M | 785 µL |

The final pH is adjusted to 7.4±0.4. Optionally, 25 µL of solution of Tween 20 at 32.7 mM can be added to this solution (final concentration of Tween 20=8 µM).

The clear solution is filtered on a 0.22 µm membrane and stored at 4° C.

B10. Preparation of a Solution of Insulin Analog Lispro at 100 IU/mL in the Presence of Oligosaccharide 2 and 6 mM of Citrate.

For a final volume of 100 mL of formulation, with a weight ratio [oligosaccharide 2]/[insulin lispro] of 2.0 and a concentration of 6 mM of citrate, the various reagents are added in the quantities specified below:

| | |
|---|---|
| Oligosaccharide 2 in lyophilized form | 730 mg |
| Commercial solution Humalog ® 100 IU/ml | 100 mL |
| Solution of sodium citrate at 1.188M | 506 µL |

The final pH is adjusted to 7.4±0.4.

The clear solution is filtered on a 0.22 µm membrane and stored at 4° C.

B11. Preparation of a Solution of Insulin Analog Lispro at 100 IU/mL in the Presence of Oligosaccharide 1 and 9.3 mM of Citrate.

For a final volume of 100 mL of formulation, with a weight ratio [oligosaccharide 1]/[lispro] of 2.0 and a concentration of 9.3 mM of citrate, the various reagents are added in the quantities specified below:

| Oligosaccharide 1 in lyophilized form | 730 mg |
| Commercial solution Humalog ® 100 IU/ml | 100 mL |
| Solution of sodium citrate at 1.188M | 785 µL |

The final pH is adjusted to 7.4±0.4. The clear solution is filtered on a 0.22 µm membrane and stored at 4° C.

B12. Preparation of a Solution of Insulin Lispro at 100 IU/mL in the Presence of Oligosaccharide 1 and 18.6 mM of Citrate.

For a final volume of 100 mL of formulation, with a weight ratio [oligosaccharide 1]/[lispro] of 2.0 and a concentration of 18.6 mM of citrate, the various reagents are added in the quantities specified below:

| Oligosaccharide 1 in lyophilized form | 730 mg |
| Commercial solution Humalog ® 100 IU/ml | 100 mL |
| Solution of sodium citrate at 1.188M | 1570 µL |

The final pH is adjusted to 7.4±0.4. The clear solution is filtered on a 0.22 µm membrane and stored at 4° C.

B13. Preparation of a Solution of Insulin Lispro at 100 IU/mL in the Presence of Oligosaccharide 2 and 7.3 mg/mL of Polyanionic Compound 1.

For a final volume of 100 mL of formulation, with a weight ratio [oligosaccharide 2]/[polyanionic compound 1]/[lispro] of 2/2/1, the various reagents are added in the quantities specified below:

| Oligosaccharide 2 in lyophilized form | 730 mg |
| Polyanionic compound 1 in lyophilized form | 730 mg |
| Commercial solution Humalog ® 100 IU/ml | 100 mL |

The final pH is adjusted to 7.4±0.4. The clear solution is filtered on a 0.22 µm membrane and stored at 4° C.

B14. Preparation of a Solution of Insulin Lispro at 100 IU/mL in the Presence of Oligosaccharide 2 and 14.6 mg/mL of Polyanionic Compound 1.

For a final volume of 100 mL of formulation, with a weight ratio [oligosaccharide 2]/[polyanionic compound 1]/[lispro] of 2/4/1, the various reagents are added in the quantities specified below:

| Oligosaccharide 2 in lyophilized form | 730 mg |
| Polyanionic compound 1 in lyophilized form | 1460 mg |
| Commercial solution Humalog ® 100 IU/ml | 100 mL |

The final pH is adjusted to 7.4±0.4. The clear solution is filtered on a 0.22 µm membrane and stored at 4° C.

B15. Preparation of a Solution of Insulin Lispro at 100 IU/mL in the Presence of Oligosaccharide 2 at 14.6 mg/mL.

For a final volume of 100 mL of formulation, with a weight ratio [oligosaccharide 2]/[insulin lispro] of 4, the various reagents are added in the specified quantities:

| Oligosaccharide 2 in lyophilized form | 1460 mg |
| Commercial solution Humalog ® 100 IU/ml | 100 mL |

The final pH is adjusted to 7.4±0.4. The clear solution is filtered on a 0.22 µm membrane and stored at 4° C.

B16. Preparation of a Solution of Insulin Analog Lispro at 100 IU/mL in the Presence of Oligosaccharide 2 and 80 mM of Sodium Tartrate.

For a final volume of 100 mL of formulation, with a weight ratio [oligosaccharide 2]/[insulin lispro] of 2.0 and a concentration of 80 mM of sodium tartrate, the various reagents are added in the quantities specified below:

| Oligosaccharide 2 in lyophilized form | 730 mg |
| Commercial solution Humalog ® 100 IU/ml | 100 mL |
| Sodium tartrate | 1.552 g |

For the tartrate, it is possible to use the acid form or the basic form in the form of sodium salt, of potassium salt or of some other salt compatible with an injectable formulation.

The final pH is adjusted to 7.4±0.4.

The clear solution is filtered on a 0.22 µm membrane and stored at 4° C.

B17. Preparation of a Solution of Insulin Analog Lispro at 100 IU/mL in the Presence of Oligosaccharide 2 and 60 mM of Phosphate.

For a final volume of 100 mL of formulation, with a weight ratio [oligosaccharide 2]/[insulin lispro] of 2.0 and a concentration of 60 mM of phosphate, the various reagents are added in the quantities specified below:

| Oligosaccharide 2 in lyophilized form | 730 mg |
| Commercial solution Humalog ® 100 IU/ml | 100 mL |
| $Na_2HPO_4 \cdot 12H_2O$ | 2.148 g |

For the phosphate, it is possible to use the acid form or the basic form in the form of sodium salt, of potassium salt or of some other salt compatible with an injectable formulation.

The final pH is adjusted to 7.4±0.4.

The clear solution is filtered on a 0.22 µm membrane and stored at 4° C.

B18. Preparation of a Solution of Insulin Analog Lispro at 100 IU/mL in the Presence of Oligosaccharide 2 and 80 mM of Sodium Aspartate.

For a final volume of 100 mL of formulation, with a weight ratio [oligosaccharide 2]/[insulin lispro] of 2.0 and a concentration of 80 mM of sodium aspartate, the various reagents are added in the quantities specified below:

| Oligosaccharide 2 in lyophilized form | 730 mg |
| Commercial solution Humalog ® 100 IU/ml | 100 mL |
| Sodium aspartate | 1.416 g |

For the aspartate, it is possible to use the acid form or the basic form in the form of sodium salt, of potassium salt or of some other salt compatible with an injectable formulation.

The final pH is adjusted to 7.4±0.4.

The clear solution is filtered on a 0.22 µm membrane and stored at 4° C.

B19. Preparation of a Solution of Insulin Analog Lispro at 100 IU/mL in the Presence of Oligosaccharide 2 and 100 mM of Sodium Glutamate.

For a final volume of 100 mL of formulation, with a weight ratio [oligosaccharide 2]/[insulin lispro] of 2.0 and a concentration of 100 mM of sodium glutamate, the various reagents are added in the quantities specified below:

| Oligosaccharide 2 in lyophilized form | 730 mg |
|---|---|
| Commercial solution Humalog ® 100 IU/ml | 100 mL |
| Sodium glutamate | 1.691 g |

For the glutamate, it is possible to use the acid form or the basic form in the form of sodium salt, of potassium salt or of some other salt compatible with an injectable formulation.

The final pH is adjusted to 7.4±0.4.

The clear solution is filtered on a 0.22 μm membrane and stored at 4° C.

B20. Preparation of a Solution of Insulin Analog Lispro at 100 IU/mL in the Presence of Oligosaccharide 2 and 60 mM of Malic Acid.

For a final volume of 100 mL of formulation, with a weight ratio [oligosaccharide 2]/[insulin lispro] of 2.0 and a concentration of 60 mM of malic acid, the various reagents are added in the quantities specified below:

| Oligosaccharide 2 in lyophilized form | 730 mg |
|---|---|
| Commercial solution Humalog ® 100 IU/ml | 100 mL |
| Malic acid | 0.805 g |

For the malic acid, it is possible to use the acid form or the basic form in the form of sodium salt, of potassium salt or of some other salt compatible with an injectable formulation.

The final pH is adjusted to 7.4±0.4.

The clear solution is filtered on a 0.22 μm membrane and stored at 4° C.

B21. Preparation of a Solution of Insulin Analog Lispro at 100 IU/mL in the Presence of Oligosaccharide 2 and 80 mM of Sodium Succinate.

For a final volume of 100 mL of formulation, with a weight ratio [oligosaccharide 2]/[insulin lispro] of 2.0 and a concentration of 80 mM of sodium succinate, the various reagents are added in the quantities specified below:

| Oligosaccharide 2 in lyophilized form | 730 mg |
|---|---|
| Commercial solution Humalog ® 100 IU/ml | 100 mL |
| Sodium succinate | 1.296 g |

For the succinate, it is possible to use the acid form or the basic form in the form of sodium salt, of potassium salt or of some other salt compatible with an injectable formulation.

The final pH is adjusted to 7.4±0.4.

The clear solution is filtered on a 0.22 g±m membrane and stored at 4° C.

B22. Preparation of a Solution of Insulin Analog Lispro at 100 IU/mL in the Presence of Oligosaccharide 2 and 50 mM of Sodium Adipate.

For a final volume of 100 mL of formulation, with a weight ratio [oligosaccharide 2]/[insulin lispro] of 2.0 and a concentration of 50 mM of sodium adipate, the various reagents are added in the quantities specified below:

| Oligosaccharide 2 in lyophilized form | 730 mg |
|---|---|
| Commercial solution Humalog ® 100 IU/ml | 100 mL |
| Sodium adipate | 0.951 g |

For the adipate, it is possible to use the acid form or the basic form in the form of sodium salt, of potassium salt or of some other salt compatible with an injectable formulation.

The final pH is adjusted to 7.4±0.4.

The clear solution is filtered on a 0.22 μm membrane and stored at 4° C.

B23. Preparation of a Solution of Insulin Analog Lispro at 100 IU/mL in the Presence of Oligosaccharide 2 and 80 mM of Sodium Ascorbate.

For a final volume of 100 mL of formulation, with a weight ratio [oligosaccharide 2]/[insulin lispro] of 2.0 and a concentration of 80 mM of sodium ascorbate, the various reagents are added in the quantities specified below:

| Oligosaccharide 2 in lyophilized form | 730 mg |
|---|---|
| Commercial solution Humalog ® 100 IU/ml | 100 mL |
| Sodium ascorbate | 1.585 g |

For the ascorbate, it is possible to use the acid form or the basic form in the form of sodium salt, of potassium salt or of some other salt compatible with an injectable formulation.

The final pH is adjusted to 7.4±0.4.

The clear solution is filtered on a 0.22 μm membrane and stored at 4° C.

B24. Preparation of a Solution of Insulin Analog Lispro at 100 IU/mL in the Presence of Oligosaccharide 2 and 10 mM of Sodium Oxalate.

For a final volume of 100 mL of formulation, with a weight ratio [oligosaccharide 2]/[insulin lispro] of 2.0 and a concentration of 10 mM of sodium oxalate, the various reagents are added in the quantities specified below:

| Oligosaccharide 2 in lyophilized form | 730 mg |
|---|---|
| Commercial solution Humalog ® 100 IU/ml | 100 mL |
| Sodium oxalate | 134 mg |

For the oxalate, it is possible to use the acid form or the basic form in the form of sodium salt, of potassium salt or of some other salt compatible with an injectable formulation.

The final pH is adjusted to 7.4±0.4.

The clear solution is filtered on a 0.22 μm membrane and stored at 4° C.

B25. Preparation of a Solution of Insulin Lispro at 100 IU/mL in the Presence of Oligosaccharide 2 and 14.6 mg/mL of Polyglutamic Acid.

For a final volume of 100 mL of formulation, with a weight ratio [oligosaccharide 2]/[polyglutamic acid]/[insulin lispro] of 2/4/1, the various reagents are added in the quantities specified below:

| Oligosaccharide 2 in lyophilized form | 730 mg |
|---|---|
| Polyglutamic acid in lyophilized form | 1460 mg |
| Commercial solution Humalog ® 100 IU/ml | 100 mL |

For the polyglutamic acid, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B26. Preparation of a Solution of Insulin Lispro at 100 IU/mL in the Presence of Oligosaccharide 2 and 14.6 mg/mL of Polyaspartic Acid.

For a final volume of 100 mL of formulation, with a weight ratio [oligosaccharide 2]/[polyaspartic acid]/[insulin lispro] of 2/4/1, the various reagents are added in the quantities specified below:

| | |
|---|---|
| Oligosaccharide 2 in lyophilized form | 730 mg |
| Polyaspartic acid in lyophilized form | 1460 mg |
| Commercial solution Humalog ® 100 IU/ml | 100 mL |

For the polyaspartic acid, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B27. Preparation of a Solution of Insulin Lispro at 100 IU/mL in the Presence of Oligosaccharide 2 and 14.6 mg/mL of Polyanionic Compound 2.

For a final volume of 100 mL of formulation, with a weight ratio [oligosaccharide 2]/[polyanionic compound 2]/[insulin lispro] of 2/4/1, the various reagents are added in the quantities specified below:

| | |
|---|---|
| Oligosaccharide 2 in lyophilized form | 730 mg |
| Polyanionic compound 2 in lyophilized form | 1460 mg |
| Commercial solution Humalog ® 100 IU/ml | 100 mL |

The polyanionic compound 2 can be used in the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B28. Preparation of a Solution of Insulin Lispro at 100 IU/mL in the Presence of Oligosaccharide 2 and 7.3 mg/mL of Sodium Triphosphate.

For a final volume of 100 mL of formulation, with a weight ratio [oligosaccharide 2]/[triphosphate]/[insulin lispro] of 2/2/1, the various reagents are added in the quantities specified below:

| | |
|---|---|
| Oligosaccharide 2 in lyophilized form | 730 mg |
| Sodium triphosphate or polyphosphate | 730 mg |
| Commercial solution Humalog ® 100 IU/ml | 100 mL |

For the triphosphate or polyphosphate, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B29. Preparation of a Solution of Insulin Lispro at 100 IU/mL in the Presence of Oligosaccharide 2 and 14.6 mg/mL of Poly(Acrylic Acid).

For a final volume of 100 mL of formulation, with a weight ratio [oligosaccharide 2]/[poly(acrylic acid)]/[insulin lispro] of 2/4/1, the various reagents are added in the quantities specified below:

| | |
|---|---|
| Oligosaccharide 2 in lyophilized form | 730 mg |
| Poly(acrylic acid) in lyophilized form | 1460 mg |
| Commercial solution Humalog ® 100 IU/ml | 100 mL |

For the poly(acrylic acid), it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B30. Preparation of a Solution of Insulin Lispro at 100 IU/mL in the Presence of Oligosaccharide 2 and 14.6 mg/mL of (Low Molecular Weight) Sodium Alginate.

For a final volume of 100 mL of formulation, with a weight ratio [oligosaccharide 2]/[sodium alginate]/[insulin lispro] of 2/4/1, the various reagents are added in the quantities specified below:

| | |
|---|---|
| Oligosaccharide 2 in lyophilized form | 730 mg |
| Sodium alginate | 1460 mg |
| Commercial solution Humalog ® 100 IU/ml | 100 mL |

For the alginate, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B31. Preparation of a Solution of Insulin Lispro at 100 IU/mL in the Presence of Oligosaccharide 2 and 21.9 mg/mL of Polymer Based on Glucuronic Acid.

For a final volume of 100 mL of formulation, with a weight ratio [oligosaccharide 2]/[polymer based on glucuronic acid]/[insulin lispro] of 2/6/1, the various reagents are added in the quantities specified below:

| | |
|---|---|
| Oligosaccharide 2 in lyophilized form | 730 mg |
| Polymer based on glucuronic acid | 2190 mg |
| Commercial solution Humalog ® 100 IU/ml | 100 mL |

For the polymers based on glucuronic acid, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B32. Preparation of a Solution of Insulin Lispro at 100 IU/mL in the Presence of Oligosaccharide 2 and 21.9 mg/mL of Polymer Based on Galacturonic Acid.

For a final volume of 100 mL of formulation, with a weight ratio [oligosaccharide 2]/[polymer based on galacturonic acid]/[insulin lispro] of 2/6/1, the various reagents are added in the quantities specified below:

| | |
|---|---|
| Oligosaccharide 2 in lyophilized form | 730 mg |
| Polymer based on galacturonic acid | 2190 mg |
| Commercial solution Humalog ® 100 IU/ml | 100 mL |

For the polymers based on galacturonic acid, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B33. Preparation of a Solution of Insulin Lispro at 100 IU/mL in the Presence of Oligosaccharide 2 and 21.9 mg/mL of Polymer Based on Hyaluronic Acid.

For a final volume of 100 mL of formulation, with a weight ratio [oligosaccharide 2]/[polymer based on hyaluronic acid]/[insulin lispro] of 2/6/1, the various reagents are added in the quantities specified below:

| | |
|---|---|
| Oligosaccharide 2 in lyophilized form | 730 mg |
| Polymer based on hyaluronic acid | 2190 mg |
| Commercial solution Humalog ® 100 IU/ml | 100 mL |

For the polymers based on hyaluronic acid, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B34. Preparation of a Solution of Insulin Analog Lispro at 100 IU/mL in the Presence of Oligosaccharide 1 and 80 mM of Tartrate.

For a final volume of 100 mL of formulation, with a weight ratio [oligosaccharide 1]/[insulin lispro] of 2.0 and a concentration of 80 mM of tartrate, the various reagents are added in the quantities specified below:

| | |
|---|---|
| Oligosaccharide 1 in lyophilized form | 730 mg |
| Commercial solution Humalog ® 100 IU/ml | 100 mL |
| Sodium tartrate | 1.552 g |

For the tartrate, it is possible to use the acid form or the basic form in the form of sodium salt, of potassium salt or of some other salt compatible with an injectable formulation.

The final pH is adjusted to 7.4±0.4.

The clear solution is filtered on a 0.22 μm membrane and stored at 4° C.

B35. Preparation of a Solution of Insulin Analog Lispro at 100 IU/mL in the Presence of Oligosaccharide 1 and 60 mM of Phosphate.

For a final volume of 100 mL of formulation, with a weight ratio [oligosaccharide 1]/[insulin lispro] of 2.0 and a concentration of 60 mM of phosphate, the various reagents are added in the quantities specified below:

| | |
|---|---|
| Oligosaccharide 1 in lyophilized form | 730 mg |
| Commercial solution Humalog ® 100 IU/ml | 100 mL |
| $Na_2HPO_4 \cdot 12H_2O$ | 2.148 g |

For the phosphate, it is possible to use the acid form or the basic form in the form of sodium salt, of potassium salt or of some other salt compatible with an injectable formulation.

The final pH is adjusted to 7.4±0.4.

The clear solution is filtered on a 0.22 μm membrane and stored at 4° C.

B36. Preparation of a Solution of Insulin Analog Lispro at 100 IU/mL in the Presence of Oligosaccharide 1 and 80 mM of Sodium Aspartate.

For a final volume of 100 mL of formulation, with a weight ratio [oligosaccharide 1]/[insulin lispro] of 2.0 and a concentration of 80 mM of sodium aspartate, the various reagents are added in the quantities specified below:

| | |
|---|---|
| Oligosaccharide 1 in lyophilized form | 730 mg |
| Commercial solution Humalog ® 100 IU/ml | 100 mL |
| Sodium aspartate | 1.416 g |

For the aspartate, it is possible to use the acid form or the basic form in the form of sodium salt, of potassium salt or of some other salt compatible with an injectable formulation.

The final pH is adjusted to 7.4±0.4.

The clear solution is filtered on a 0.22 μm membrane and stored at 4° C.

B37. Preparation of a Solution of Insulin Analog Lispro at 100 IU/mL in the Presence of Oligosaccharide 1 and 100 mM of Sodium Glutamate.

For a final volume of 100 mL of formulation, with a weight ratio [oligosaccharide 1]/[insulin lispro] of 2.0 and a concentration of 100 mM of sodium glutamate, the various reagents are added in the quantities specified below:

| | |
|---|---|
| Oligosaccharide 1 in lyophilized form | 730 mg |
| Commercial solution Humalog ® 100 IU/ml | 100 mL |
| Sodium glutamate | 1.691 g |

For the glutamate, it is possible to use the acid form or the basic form in the form of sodium salt, of potassium salt or of some other salt compatible with an injectable formulation.

The final pH is adjusted to 7.4±0.4.

The clear solution is filtered on a 0.22 μm membrane and stored at 4° C.

B38. Preparation of a Solution of Insulin Analog Lispro at 100 IU/mL in the Presence of Oligosaccharide 1 and 60 mM of Malic Acid.

For a final volume of 100 mL of formulation, with a weight ratio [oligosaccharide 1]/[insulin lispro] of 2.0 and a concentration of 60 mM of malic acid, the various reagents are added in the quantities specified below:

| | |
|---|---|
| Oligosaccharide 1 in lyophilized form | 730 mg |
| Commercial solution Humalog ® 100 IU/ml | 100 mL |
| Malic acid | 0.805 g |

For the malic acid, it is possible to use the acid form or the basic form in the form of sodium salt, of potassium salt or of some other salt compatible with an injectable formulation.

The final pH is adjusted to 7.4±0.4.

The clear solution is filtered on a 0.22 μm membrane and stored at 4° C.

B39. Preparation of a Solution of Insulin Analog Lispro at 100 IU/mL in the Presence of Oligosaccharide 1 and 80 mM of Sodium Succinate.

For a final volume of 100 mL of formulation, with a weight ratio [oligosaccharide 1]/[insulin lispro] of 2.0 and a concentration of 80 mM of sodium succinate, the various reagents are added in the quantities specified below:

| | |
|---|---|
| Oligosaccharide 1 in lyophilized form | 730 mg |
| Commercial solution Humalog ® 100 IU/ml | 100 mL |
| Sodium succinate | 1.296 g |

For the succinate, it is possible to use the acid form or the basic form in the form of sodium salt, of potassium salt or of some other salt compatible with an injectable formulation.

The final pH is adjusted to 7.4±0.4.

The clear solution is filtered on a 0.22 µm membrane and stored at 4° C.

B40. Preparation of a Solution of Insulin Analog Lispro at 100 IU/mL in the Presence of Oligosaccharide 1 and 50 mM of Sodium Adipate.

For a final volume of 100 mL of formulation, with a weight ratio [oligosaccharide 1]/[insulin lispro] of 2.0 and a concentration of 50 mM of sodium adipate, the various reagents are added in the quantities specified below:

| | |
|---|---|
| Oligosaccharide 1 in lyophilized form | 730 mg |
| Commercial solution Humalog ® 100 IU/ml | 100 mL |
| Sodium adipate | 0.951 g |

For the adipate, it is possible to use the acid form or the basic form in the form of sodium salt, of potassium salt or of some other salt compatible with an injectable formulation.

The final pH is adjusted to 7.4±0.4.

The clear solution is filtered on a 0.22 µm membrane and stored at 4° C.

B41. Preparation of a Solution of Insulin Analog Lispro at 100 IU/mL in the Presence of Oligosaccharide 1 and 80 mM of Sodium Ascorbate.

For a final volume of 100 mL of formulation, with a weight ratio [oligosaccharide 1]/[insulin lispro] of 2.0 and a concentration of 80 mM of sodium ascorbate, the various reagents are added in the quantities specified below:

| | |
|---|---|
| Oligosaccharide 1 in lyophilized form | 730 mg |
| Commercial solution Humalog ® 100 IU/ml | 100 mL |
| Sodium ascorbate | 1.585 g |

For the ascorbate, it is possible to use the acid form or the basic form in the form of sodium salt, of potassium salt or of some other salt compatible with an injectable formulation.

The final pH is adjusted to 7.4±0.4.

The clear solution is filtered on a 0.22 pin membrane and stored at 4° C.

B42. Preparation of a Solution of Insulin Analog Lispro at 100 IU/mL in the Presence of Oligosaccharide 1 and 10 mM of Sodium Oxalate.

For a final volume of 100 mL of formulation, with a weight ratio [oligosaccharide 1]/[insulin lispro] of 2.0 and a concentration of 10 mM of sodium oxalate, the various reagents are added in the quantities specified below:

| | |
|---|---|
| Oligosaccharide 1 in lyophilized form | 730 mg |
| Commercial solution Humalog ® 100 IU/ml | 100 mL |
| Sodium oxalate | 134 mg |

For the oxalate, it is possible to use the acid form or the basic form in the form of sodium salt, of potassium salt or of some other salt compatible with an injectable formulation.

The final pH is adjusted to 7.4±0.4.

The clear solution is filtered on a 0.22 µm membrane and stored at 4° C.

B43. Preparation of a Solution of Insulin Lispro at 100 IU/mL in the Presence of Oligosaccharide 1 and 14.6 mg/mL of Polyglutamic Acid.

For a final volume of 100 mL of formulation, with a weight ratio [oligosaccharide 1]/[polyglutamic acid]/[insulin lispro] of 2/4/1, the various reagents are added in the quantities specified below:

| | |
|---|---|
| Oligosaccharide 1 in lyophilized form | 730 mg |
| Polyglutamic acid in lyophilized form | 1460 mg |
| Commercial solution Humalog ® 100 IU/ml | 100 mL |

For the polyglutamic acid, it is possible to use the acid form or the basic form in the form of sodium salt, of potassium salt or of some other salt compatible with an injectable formulation.

The final pH is adjusted to 7.4±0.4. The clear solution is filtered on a 0.22 µm membrane and stored at 4° C.

B44. Preparation of a Solution of Insulin Lispro at 100 IU/mL in the Presence of Oligosaccharide 1 and 14.6 mg/mL of Polyaspartic Acid.

For a final volume of 100 mL of formulation, with a weight ratio [oligosaccharide 1]/[polyaspartic acid]/[insulin lispro] of 2/4/1, the various reagents are added in the quantities specified below:

| | |
|---|---|
| Oligosaccharide 1 in lyophilized form | 730 mg |
| Polyaspartic acid in lyophilized form | 1460 mg |
| Commercial solution Humalog ® 100 IU/ml | 100 mL |

For the polyaspartic acid, it is possible to use the acid form or the basic form in the form of sodium salt, of potassium salt or of some other salt compatible with an injectable formulation.

The final pH is adjusted to 7.4±0.4. The clear solution is filtered on a 0.22 µm membrane and stored at 4° C.

B45. Preparation of a Solution of Insulin Lispro at 100 IU/mL in the Presence of Oligosaccharide 1 and 14.6 mg/mL of Polyanionic Compound 2.

For a final volume of 100 mL of formulation, with a weight ratio [oligosaccharide 1]/[polyanionic compound 2]/[insulin lispro] of 2/4/1, the various reagents are added in the quantities specified below:

| | |
|---|---|
| Oligosaccharide 1 in lyophilized form | 730 mg |
| Polyanionic compound 2 in lyophilized form | 1460 mg |
| Commercial solution Humalog ® 100 IU/ml | 100 mL |

The polyanionic compound 2 can be used in the acid form or the basic form in the form of sodium salt, of potassium salt or of some other salt compatible with an injectable formulation.

The final pH is adjusted to 7.4±0.4. The clear solution is filtered on a 0.22 µm membrane and stored at 4° C.

B46. Preparation of a Solution of Insulin Lispro at 100 IU/mL in the Presence of Oligosaccharide 1 and 7.3 mg/mL of Sodium Triphosphate.

For a final volume of 100 mL of formulation, with a weight ratio [oligosaccharide 1]/[triphosphate]/[insulin lispro] of 2/2/1, the various reagents are added in the quantities specified below:

| | |
|---|---|
| Oligosaccharide 1 in lyophilized form | 730 mg |
| Sodium triphosphate or polyphosphate | 730 mg |
| Commercial solution Humalog® 100 IU/ml | 100 mL |

For the triphosphate, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B47. Preparation of a Solution of Insulin Lispro at 100 IU/mL in the Presence of Oligosaccharide 1 and 14.6 mg/mL of Poly(Acrylic Acid).

For a final volume of 100 mL of formulation, with a weight ratio [oligosaccharide 1]/[poly(acrylic acid)]/[insulin lispro] of 2/4/1, the various reagents are added in the quantities specified below:

| | |
|---|---|
| Oligosaccharide 1 in lyophilized form | 730 mg |
| Poly(acrylic acid) in lyophilized form | 1460 mg |
| Commercial solution Humalog® 100 IU/ml | 100 mL |

For the poly(acrylic acid), it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B48. Preparation of a Solution of Insulin Lispro at 100 IU/mL in the Presence of Oligosaccharide 1 and 14.6 mg/mL of (Low Molecular Weight) Sodium Alginate.

For a final volume of 100 mL of formulation, with a weight ratio [oligosaccharide 1]/[sodium alginate]/[insulin lispro] of 2/4/1, the various reagents are added in the quantities specified below:

| | |
|---|---|
| Oligosaccharide 1 in lyophilized form | 730 mg |
| Sodium alginate | 1460 mg |
| Commercial solution Humalog® 100 IU/ml | 100 mL |

For the alginate, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B49. Preparation of a Solution of Insulin Lispro at 100 IU/mL in the Presence of Oligosaccharide 1 and 21.9 mg/mL of Polymer Based on Glucuronic Acid.

For a final volume of 100 mL of formulation, with a weight ratio [oligosaccharide 1]/[polymer based on glucuronic acid]/[insulin lispro] of 2/6/1, the various reagents are added in the quantities specified below:

| | |
|---|---|
| Oligosaccharide 1 in lyophilized form | 730 mg |
| Polymer based on glucuronic acid | 2190 mg |
| Commercial solution Humalog® 100 IU/ml | 100 mL |

For the polymers based on glucuronic acid, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B50. Preparation of a Solution of Insulin Lispro at 100 IU/mL in the Presence of Oligosaccharide 1 and 21.9 mg/mL of Polymer Based on Galacturonic Acid.

For a final volume of 100 mL of formulation, with a weight ratio [oligosaccharide 1]/[polymer based on galacturonic acid]/[insulin lispro] of 2/6/1, the various reagents are added in the quantities specified below:

| | |
|---|---|
| Oligosaccharide 1 in lyophilized form | 730 mg |
| Polymer based on galacturonic acid | 2190 mg |
| Commercial solution Humalog® 100 IU/ml | 100 mL |

For the polymers based on galacturonic acid, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B51. Preparation of a Solution of Insulin Lispro at 100 IU/mL in the Presence of Oligosaccharide 1 and 21.9 mg/mL of Polymer Based on Hyaluronic Acid.

For a final volume of 100 mL of formulation, with a weight ratio [oligosaccharide 1]/[polymer based on hyaluronic acid]/[insulin lispro] of 2/6/1, the various reagents are added in the quantities specified below:

| | |
|---|---|
| Oligosaccharide 1 in lyophilized form | 730 mg |
| Polymer based on hyaluronic acid | 2190 mg |
| Commercial solution Humalog® 100 IU/ml | 100 mL |

For the polymers based on hyaluronic acid, it is possible to use the acid form or the basic form in the form of sodium salt, of potassium salt or of some other salt compatible with an injectable formulation.

The final pH is adjusted to 7.4±0.4. The clear solution is filtered on a 0.22 μm membrane and stored at 4° C.

B52. Preparation of a Solution of Insulin Analog (Insulin Lispro) at 200 IU/mL.

The commercial formulation of insulin lispro (Humalog®) was concentrated using AMICON Ultra-15 centrifugation tubes with a cutoff at 3 kDa. The Amicon tubes were first rinsed with 12 mL of deionized water. 12 mL of the commercial formulation was centrifuged for 35 minutes at 4000 g at 20° C. The volume of retentate was measured and the concentration was estimated from the volume of retentate. All retentates were combined and the total concentration was estimated (>200 IU/mL).

The concentration of this concentrated solution of lispro was adjusted to 200 IU/mL by adding the commercial formulation of insulin lispro (Humalog®). The concentrated formulation of concentrated insulin lispro has the same concentrations of excipients (m-cresol, glycerin, phosphate) as the commercial formulation at 100 IU/mL.

The final pH is adjusted to 7.4±0.4. The clear solution is filtered on a 0.22 μm membrane and stored at 4° C.

B53. Preparation of a Solution of Insulin Lispro at 200 IU/mL in the Presence of Oligosaccharide 2 at 14.6 mg/mL and 9.3 mM of Citrate.

For a final volume of 100 mL of formulation with a weight ratio [oligosaccharide 2/Lispro] of 2, the various reagents are mixed in the quantities stated below

| Insulin lispro at 200 IU/mL | 100 mL |
| --- | --- |
| Lyophilizate of oligosaccharide 2 | 1460 mg |
| Solution of sodium citrate at 1.188M | 1570 μL |

The final pH is adjusted to 7.4±0.4.

The clear solution is filtered on a 0.22 μm membrane and stored at 4° C.

B54. Preparation of a Solution of Insulin Lispro at 200 IU/mL in the Presence of Oligosaccharide 2 at 14.6 mg/mL and of Polyanionic Compound 1 at 14.6 mg/mL.

For a final volume of 100 mL of formulation with a weight ratio [(oligosaccharide 2/polyanionic compound 1/lispro] of 2/2/1, the various reagents are mixed in the quantities stated below.

| Insulin lispro at 200 IU/mL | 100 mL |
| --- | --- |
| Lyophilizate of oligosaccharide 2 | 1460 mg |
| Lyophilizate of polyanionic compound 1 | 1460 mg |

The final pH is adjusted to 7.4±0.4.

The clear solution is filtered on a 0.22 μm membrane and stored at 4° C.

B55. Preparation of a Solution of Insulin Lispro at 200 IU/mL in the Presence of Oligosaccharide 2 at 14.6 mg/mL and of Polyanionic Compound 1 at 29.2 mg/mL.

For a final volume of 100 mL of formulation with a weight ratio [oligosaccharide 2/polyanionic compound 1/lispro] of 2/4/1, the various reagents are mixed in the quantities stated below.

| Insulin lispro at 200 IU/mL | 100 mL |
| --- | --- |
| Lyophilizate of oligosaccharide 2 | 1460 mg |
| Lyophilizate of polyanionic compound 1 | 2920 mg |

The final pH is adjusted to 7.4±0.4.

The clear solution is filtered on a 0.22 μm membrane and stored at 4° C.

B56: Preparation of a Solution of Human Insulin at 100 IU/mL in the Presence of Oligosaccharide 2 and 80 mM of Tartrate.

For a final volume of 100 mL of formulation with a weight ratio [oligosaccharide 2]/[insulin] of 2 and 80 mM of tartrate, the various reagents are mixed in the quantities stated below:

| Human insulin at 500 IU/mL | 20 mL |
| --- | --- |
| Solution of oligosaccharide 2 at 36.01 mg/mL | 20.27 mL |
| Solution 96.6 mM m-cresol/566 mM glycerin | 30 mL |
| Water | 28.95 mL |
| Sodium tartrate | 1.552 g |

For the tartrate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B57. Preparation of a Solution of Human Insulin at 100 IU/mL in the Presence of Oligosaccharide 2 and 80 mM of Phosphate.

For a final volume of 100 mL of formulation with a weight ratio [oligosaccharide 2]/[insulin] of 2 and 80 mM of phosphate, the various reagents are mixed in the quantities stated below:

| Human insulin at 500 IU/mL | 20 mL |
| --- | --- |
| Solution of oligosaccharide 2 at 36.01 mg/mL | 20.27 mL |
| Solution 96.6 mM m-cresol/566 mM glycerin | 30 mL |
| Water | 28.95 mL |
| $Na_2HPO_4 \cdot 12H_2O$ | 2.864 g |

For the phosphate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B58 Preparation of a Solution of Human Insulin at 100 IU/mL in the Presence of Oligosaccharide 2 and 80 mM of Aspartate.

For a final volume of 100 mL of formulation with a weight ratio [oligosaccharide 2]/[insulin] of 2 and 80 mM of aspartate, the various reagents are mixed in the quantities stated below:

| Human insulin at 500 IU/mL | 20 mL |
| --- | --- |
| Solution of oligosaccharide 2 at 36.01 mg/mL | 20.27 mL |
| Solution 96.6 mM m-cresol/566 mM glycerin | 30 mL |
| Water | 28.95 mL |
| Sodium aspartate | 1.416 g |

For the aspartate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B59. Preparation of a Solution of Human Insulin at 100 IU/mL in the Presence of Oligosaccharide 2 and 100 mM of Glutamate.

For a final volume of 100 mL of formulation with a weight ratio [oligosaccharide 2]/[insulin] of 2 and 100 mM of glutamate, the various reagents are mixed in the quantities stated below:

| Human insulin at 500 IU/mL | 20 mL |
| --- | --- |
| Solution of oligosaccharide 2 at 36.01 mg/mL | 20.27 mL |
| Solution 96.6 mM m-cresol/566 mM glycerin | 30 mL |
| Water | 28.95 mL |
| Sodium glutamate | 1.691 g |

For the glutamate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B60. Preparation of a Solution of Human Insulin at 100 IU/mL in the Presence of Oligosaccharide 2 and 60 mM of Malic Acid.

For a final volume of 100 mL of formulation with a weight ratio [oligosaccharide 2]/[insulin] of 2 and 60 mM of malic acid, the various reagents are mixed in the quantities stated below:

| | |
|---|---:|
| Human insulin at 500 IU/mL | 20 mL |
| Solution of oligosaccharide 2 at 36.01 mg/mL | 20.27 mL |
| Solution 96.6 mM m-cresol/566 mM glycerin | 30 mL |
| Water | 28.95 mL |
| Malic acid | 0.805 g |

For the malic acid, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B61. Preparation of a Solution of Human Insulin at 100 IU/mL in the Presence of Oligosaccharide 2 and 80 mM of Succinate.

For a final volume of 100 mL of formulation with a weight ratio [oligosaccharide 2]/[insulin] of 2 and 80 mM of succinate, the various reagents are mixed in the quantities stated below:

| | |
|---|---:|
| Human insulin at 500 IU/mL | 20 mL |
| Solution of oligosaccharide 2 at 36.01 mg/mL | 20.27 mL |
| Solution 96.6 mM m-cresol/566 mM glycerin | 30 mL |
| Water | 28.95 mL |
| Sodium succinate | 1.296 g |

For the succinate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B62. Preparation of a Solution of Human Insulin at 100 IU/mL in the Presence of Oligosaccharide 2 and 50 mM of Adipate.

For a final volume of 100 mL of formulation with a weight ratio [oligosaccharide 2]/[insulin] of 2 and 50 mM of adipate, the various reagents are mixed in the quantities stated below:

| | |
|---|---:|
| Human insulin at 500 IU/mL | 20 mL |
| Solution of oligosaccharide 2 at 36.01 mg/mL | 20.27 mL |
| Solution 96.6 mM m-cresol/566 mM glycerin | 30 mL |
| Water | 28.95 mL |
| Sodium adipate | 0.951 g |

For the adipate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B63: Preparation of a Solution of Human Insulin at 100 IU/mL in the Presence of Oligosaccharide 2 and 80 mM of Ascorbate.

For a final volume of 100 mL of formulation with a weight ratio [oligosaccharide 2]/[insulin] of 2 and 80 mM of ascorbate, the various reagents are mixed in the quantities stated below.

| | |
|---|---:|
| Human insulin at 500 IU/mL | 20 mL |
| Solution of oligosaccharide 2 at 36.01 mg/mL | 20.27 mL |
| Solution 96.6 mM m-cresol/566 mM glycerin | 30 mL |
| Water | 28.95 mL |
| Sodium ascorbate | 1.585 g |

For the ascorbate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B64: Preparation of a Solution of Human Insulin at 100 IU/mL in the Presence of Oligosaccharide 2 and 10 mM of Oxalate.

For a final volume of 100 mL of formulation with a weight ratio [oligosaccharide 2]/[insulin] of 2 and 10 mM of oxalate, the various reagents are mixed in the quantities stated below:

| | |
|---|---:|
| Human insulin at 500 IU/mL | 20 mL |
| Solution of oligosaccharide 2 at 36.01 mg/mL | 20.27 mL |
| Solution 96.6 mM m-cresol/566 mM glycerin | 30 mL |
| Water | 28.95 mL |
| Sodium oxalate | 134 mg |

For the oxalate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B65: Preparation of a Solution of Human Insulin at 100 IU/mL in the Presence of Oligosaccharide 2 and 14.6 mg/mL of Polyglutamic Acid.

For a final volume of 100 mL of formulation with a weight ratio [oligosaccharide 2]/[polyglutamic acid]/[insulin] of 2/4/1, the various reagents are mixed in the quantities stated below:

| | |
|---|---:|
| Human insulin at 500 IU/mL | 20 mL |
| Solution of oligosaccharide 2 at 36.01 mg/mL | 20.27 mL |
| Solution 96.6 mM m-cresol/566 mM glycerin | 30 mL |
| Water | 28.95 mL |
| Polyglutamic acid | 1460 mg |

For the polyglutamic acid, it is possible to use the acid form or the basic form in the form of sodium salt, of potassium salt or of some other salt compatible with an injectable formulation.

The final pH is 7.4±0.4.

This clear solution is filtered on a 0.22 min membrane and is then stored at +4° C.

B66: Preparation of a Solution of Human Insulin at 100 IU/mL in the Presence of Oligosaccharide 2 and 14.6 mg/mL of Polyaspartic Acid.

For a final volume of 100 mL of formulation with a weight ratio [oligosaccharide 2]/[polyaspartic acid]/[insulin] of 2/4/1, the various reagents are mixed in the quantities stated below:

| Human insulin at 500 IU/mL | 20 mL |
|---|---|
| Solution of oligosaccharide 2 at 36.01 mg/mL | 20.27 mL |
| Solution 96.6 mM m-cresol/566 mM glycerin | 30 mL |
| Water | 28.95 mL |
| Polyaspartic acid | 1460 mg |

For the polyaspartic acid, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B67: Preparation of a Solution of Human Insulin at 100 IU/mL in the Presence of Oligosaccharide 2 and 14.6 mg/mL of Polyanionic Compound 2.

For a final volume of 100 mL of formulation with a weight ratio [oligosaccharide 2]/[polyanionic compound 2]/[insulin] of 2/4/1, the various reagents are mixed in the quantities stated below:

| Human insulin at 500 IU/mL | 20 mL |
|---|---|
| Solution of oligosaccharide 2 at 36.01 mg/mL | 20.27 mL |
| Solution 96.6 mM m-cresol/566 mM glycerin | 30 mL |
| Water | 28.95 mL |
| Polyanionic compound 2 | 1460 mg |

The polyanionic compound 2 can be used in the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B68. Preparation of a Solution of Human Insulin at 100 IU/mL in the Presence of Oligosaccharide 2 and 7.3 mg/mL of Triphosphate.

For a final volume of 100 mL of formulation with a weight ratio [oligosaccharide 2]/[triphosphate]/[insulin] of 2/2/1, the various reagents are mixed in the quantities stated below:

| Human insulin at 500 IU/mL | 20 mL |
|---|---|
| Solution of oligosaccharide 2 at 36.01 mg/mL | 20.27 mL |
| Solution 96.6 mM m-cresol/566 mM glycerin | 30 mL |
| Water | 28.95 mL |
| Sodium triphosphate or polyphosphate | 730 mg |

For the triphosphate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B69. Preparation of a Solution of Human Insulin at 100 IU/mL in the Presence of Oligosaccharide 2 and 14.6 mg/mL of Poly(Acrylic Acid).

For a final volume of 100 mL of formulation with a weight ratio [oligosaccharide 2]/[poly(acrylic acid)]/[insulin] of 2/4/1, the various reagents are mixed in the quantities stated below:

| Human insulin at 500 IU/mL | 20 mL |
|---|---|
| Solution of oligosaccharide 2 at 36.01 mg/mL | 20.27 mL |
| Solution 96.6 mM m-cresol/566 mM glycerin | 30 mL |
| Water | 28.95 mL |
| Poly(acrylic acid) | 1460 mg |

For the poly(acrylic acid), it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B70. Preparation of a Solution of Human Insulin at 100 IU/mL in the Presence of Oligosaccharide 2 and 14.6 mg/mL of (Low Molecular Weight) Sodium Alginate.

For a final volume of 100 mL of formulation with a weight ratio [oligosaccharide 2]/[alginate]/[insulin] of 2/4/1, the various reagents are mixed in the quantities stated below:

| Human insulin at 500 IU/mL | 20 mL |
|---|---|
| Solution of oligosaccharide 2 at 36.01 mg/mL | 20.27 mL |
| Solution 96.6 mM m-cresol/566 mM glycerin | 30 mL |
| Water | 28.95 mL |
| Alginate | 1460 mg |

For the alginate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B71. Preparation of a Solution of Human Insulin at 100 IU/mL in the Presence of Oligosaccharide 2 and 21.9 mg/mL of Polymer Based on Glucuronic Acid.

For a final volume of 100 mL of formulation with a weight ratio [oligosaccharide 2]/[polymer based on glucuronic acid]/[insulin] of 2/6/1, the various reagents are mixed in the quantities stated below:

| Human insulin at 500 IU/mL | 20 mL |
|---|---|
| Solution of oligosaccharide 2 at 36.01 mg/mL | 20.27 mL |
| Solution 96.6 mM m-cresol/566 mM glycerin | 30 mL |
| Water | 28.95 mL |
| Polymer based on glucuronic acid | 2190 mg |

For the polymer based on glucuronic acid, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B72. Preparation of a Solution of Human Insulin at 100 IU/mL in the Presence of Oligosaccharide 2 and 21.9 mg/mL of Polymer Based on Galacturonic Acid.

For a final volume of 100 mL of formulation with a weight ratio [oligosaccharide 2]/[polymer based on galacturonic acid]/[insulin] of 2/6/1, the various reagents are mixed in the quantities stated below:

| Human insulin at 500 IU/mL | 20 mL |
|---|---|
| Solution of oligosaccharide 2 at 36.01 mg/mL | 20.27 mL |

-continued

| | |
|---|---|
| Solution 96.6 mM m-cresol/566 mM glycerin | 30 mL |
| Water | 28.95 mL |
| Polymer based on galacturonic acid | 2190 mg |

For the polymer based on galacturonic acid, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B73. Preparation of a Solution of Human Insulin at 100 IU/mL in the Presence of Oligosaccharide 2 and 21.9 mg/mL of Polymer Based on Hyaluronic Acid.

For a final volume of 100 mL of formulation with a weight ratio [oligosaccharide 2]/[polymer based on hyaluronic acid]/[insulin] of 2/6/1, the various reagents are mixed in the quantities stated below:

| | |
|---|---|
| Human insulin at 500 IU/mL | 20 mL |
| Solution of oligosaccharide 2 at 36.01 mg/mL | 20.27 mL |
| Solution 96.6 mM m-cresol/566 mM glycerin | 30 mL |
| Water | 28.95 mL |
| Polymer based on hyaluronic acid | 2190 mg |

For the polymer based on hyaluronic acid, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B74. Preparation of a Solution of Human Insulin at 100 IU/mL in the Presence of Oligosaccharide 1 and 80 mM of Tartrate.

For a final volume of 100 mL of formulation with a weight ratio [oligosaccharide 1]/[insulin] of 2 and 80 mM of tartrate, the various reagents are mixed in the quantities stated below:

| | |
|---|---|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Sodium tartrate | 1.552 g |

For the tartrate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B75. Preparation of a Solution of Human Insulin at 100 IU/mL in the Presence of Oligosaccharide 1 and 80 mM of Phosphate.

For a final volume of 100 mL of formulation with a weight ratio [oligosaccharide 1]/[insulin] of 2 and 80 mM of phosphate, the various reagents are mixed in the quantities stated below:

| | |
|---|---|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| $Na_2HPO_4 \cdot 12H_2O$ | 2.864 g |

For the phosphate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B76: Preparation of a Solution of Human Insulin at 100 IU/mL in the Presence of Oligosaccharide 1 and 80 mM of Aspartate.

For a final volume of 100 mL of formulation with a weight ratio [oligosaccharide 1]/[insulin] of 2 and 80 mM of aspartate, the various reagents are mixed in the quantities stated below:

| | |
|---|---|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Sodium aspartate | 1.416 g |

For the aspartate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B77. Preparation of a Solution of Human Insulin at 100 IU/mL in the Presence of Oligosaccharide 1 and 100 mM of Glutamate.

For a final volume of 100 mL of formulation with a weight ratio [oligosaccharide 1]/[insulin] of 2 and 100 mM of glutamate, the various reagents are mixed in the quantities stated below:

| | |
|---|---|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Sodium glutamate | 1.691 g |

For the glutamate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B78. Preparation of a Solution of Human Insulin at 100 IU/mL in the Presence of Oligosaccharide 1 and 60 mM of Malic Acid.

For a final volume of 100 mL of formulation with a weight ratio [oligosaccharide 2]/[insulin] of 1 and 60 mM of malic acid, the various reagents are mixed in the quantities stated below:

| | |
|---|---:|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Malic acid | 0.805 g |

For the malic acid, it is possible to use the acid form or the basic form in the form of sodium salt, of potassium salt or of some other salt compatible with an injectable formulation.

The final pH is 7.4±0.4.

This clear solution is filtered on a 0.22 µm membrane and is then stored at +4° C.

B79. Preparation of a Solution of Human Insulin at 100 IU/mL in the Presence of Oligosaccharide 1 and 80 mM of Succinate.

For a final volume of 100 mL of formulation with a weight ratio [oligosaccharide 1]/[insulin] of 2 and 80 mM of succinate, the various reagents are mixed in the quantities stated below:

| | |
|---|---:|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Sodium succinate | 1.296 g |

For the succinate, it is possible to use the acid form or the basic form in the form of sodium salt, of potassium salt or of some other salt compatible with an injectable formulation.

The final pH is 7.4±0.4.

This clear solution is filtered on a 0.22 µm membrane and is then stored at +4° C.

B80. Preparation of a Solution of Human Insulin at 100 IU/mL in the Presence of Oligosaccharide 1 and 50 mM of Adipate.

For a final volume of 100 mL of formulation with a weight ratio [oligosaccharide 1]/[insulin] of 2 and 50 mM of adipate, the various reagents are mixed in the quantities stated below:

| | |
|---|---:|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Sodium adipate | 0.951 g |

For the adipate, it is possible to use the acid form or the basic form in the form of sodium salt, of potassium salt or of some other salt compatible with an injectable formulation.

The final pH is 7.4±0.4.

This clear solution is filtered on a 0.22 µm membrane and is then stored at +4° C.

B81. Preparation of a Solution of Human Insulin at 100 IU/mL in the Presence of Oligosaccharide 1 and 80 mM of Ascorbate.

For a final volume of 100 mL of formulation with a weight ratio [oligosaccharide 1]/[insulin] of 2 and 80 mM of ascorbate, the various reagents are mixed in the quantities stated below:

| | |
|---|---:|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Sodium ascorbate | 1.585 g |

For the ascorbate, it is possible to use the acid form or the basic form in the form of sodium salt, of potassium salt or of some other salt compatible with an injectable formulation.

The final pH is 7.4±0.4.

This clear solution is filtered on a 0.22 µm membrane and is then stored at +4° C.

B82. Preparation of a Solution of Human Insulin at 100 IU/mL in the Presence of Oligosaccharide 1 and 10 mM of Oxalate For a final volume of 100 mL of formulation with a weight ratio [oligosaccharide 1]/[insulin] of 2 and 10 mM of oxalate, the various reagents are mixed in the quantities stated below:

| | |
|---|---:|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Sodium oxalate | 134 mg |

For the oxalate, it is possible to use the acid form or the basic form in the form of sodium salt, of potassium salt or of some other salt compatible with an injectable formulation.

The final pH is 7.4±0.4.

This clear solution is filtered on a 0.22 µm membrane and is then stored at +4° C.

B83. Preparation of a Solution of Human Insulin at 100 IU/mL in the Presence of Oligosaccharide 1 and 14.6 mg/mL of Polyglutamic Acid.

For a final volume of 100 mL of formulation with a weight ratio [oligosaccharide 1]/[polyglutamic acid]/[insulin] of 2/4/1, the various reagents are mixed in the quantities stated below:

| | |
|---|---:|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Polyglutamic acid | 1460 mg |

For the polyglutamic acid, it is possible to use the acid form or the basic form in the form of sodium salt, of potassium salt or of some other salt compatible with an injectable formulation.

The final pH is 7.4±0.4.

This clear solution is filtered on a 0.22 µm membrane and is then stored at +4° C.

B84. Preparation of a Solution of Human Insulin at 100 IU/mL in the Presence of Oligosaccharide 1 and 14.6 mg/mL of Polyaspartic Acid.

For a final volume of 100 mL of formulation with a weight ratio [oligosaccharide 1]/[polyaspartic acid]/[insulin] of 2/4/1, the various reagents are mixed in the quantities stated below:

| | |
|---|---|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Polyaspartic acid | 1460 mg |

For the polyaspartic acid, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B85. Preparation of a Solution of Human Insulin at 100 IU/mL in the Presence of Oligosaccharide 1 and 14.6 mg/mL of Polyanionic Compound 2.

For a final volume of 100 mL of formulation with a weight ratio [oligosaccharide 1]/[polyanionic compound 2]/[insulin] of 2/4/1, the various reagents are mixed in the quantities stated below:

| | |
|---|---|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Polyanionic compound 2 | 1460 mg |

The polyanionic compound 2 can be used in the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B86. Preparation of a Solution of Human Insulin at 100 IU/mL in the Presence of Oligosaccharide 1 and 7.3 mg/mL of Triphosphate.

For a final volume of 100 mL of formulation with a weight ratio [oligosaccharide 1]/[triphosphate]/[insulin] of 2/2/1, the various reagents are mixed in the quantities stated below:

| | |
|---|---|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Sodium triphosphate or polyphosphate | 730 mg |

For the triphosphate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B87. Preparation of a Solution of Human Insulin at 100 IU/mL in the Presence of Oligosaccharide 1 and 14.6 mg/mL of Poly(Acrylic Acid).

For a final volume of 100 mL of formulation with a weight ratio [oligosaccharide 1]/[poly(acrylic acid)]/[insulin] of 2/4/1, the various reagents are mixed in the quantities stated below:

| | |
|---|---|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Poly(acrylic acid) | 1460 mg |

For the poly(acrylic acid), it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B88. Preparation of a Solution of Human Insulin at 100 IU/mL in the Presence of Oligosaccharide 1 and 14.6 mg/mL of (Low Molecular Weight) Sodium Alginate.

For a final volume of 100 mL of formulation with a weight ratio [oligosaccharide 1]/[alginate]/[insulin] of 2/4/1, the various reagents are mixed in the quantities stated below:

| | |
|---|---|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Alginate | 1460 mg |

For the alginate, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B89. Preparation of a Solution of Human Insulin at 100 IU/mL in the Presence of Oligosaccharide 1 and 21.9 mg/mL of Polymer Based on Glucuronic Acid.

For a final volume of 100 mL of formulation with a weight ratio [oligosaccharide 1]/[polymer based on glucuronic acid]/[insulin] of 2/6/1, the various reagents are mixed in the quantities stated below:

| | |
|---|---|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Polymer based on glucuronic acid | 2190 mg |

For the polymer based on glucuronic acid, it is possible to use the acid form or the basic form in the form of sodium salt, of potassium salt or of some other salt compatible with an injectable formulation.

The final pH is 7.4±0.4.

This clear solution is filtered on a 0.22 μm membrane and is then stored at +4° C.

B90. Preparation of a Solution of Human Insulin at 100 IU/mL in the Presence of Oligosaccharide 1 and 21.9 mg/mL of Polymer Based on Galacturonic Acid.

For a final volume of 100 mL of formulation with a weight ratio [oligosaccharide 1]/[polymer based on galacturonic acid]/[insulin] of 2/6/1, the various reagents are mixed in the quantities stated below:

| | |
|---|---|
| Human insulin at 500 IU/mL | 20 mL |
| Solution of oligosaccharide 1 at 36.01 mg/mL | 20.27 mL |

-continued

| | |
|---|---|
| Solution 96.6 mM m-cresol/566 mM glycerin | 30 mL |
| Water | 28.95 mL |
| Polymer based on galacturonic acid | 2190 mg |

For the polymer based on galacturonic acid, it is possible to use the acid form or the basic form in the form of sodium salt, of potassium salt or of some other salt compatible with an injectable formulation.

The final pH is 7.4±0.4.

This clear solution is filtered on a 0.22 µm membrane and is then stored at +4° C.

B91. Preparation of a Solution of Human Insulin at 100 IU/mL in the Presence of Oligosaccharide 1 and 21.9 mg/mL of Polymer Based on Hyaluronic Acid.

For a final volume of 100 mL of formulation with a weight ratio [oligosaccharide 1]/[polymer based on hyaluronic acid]/[insulin] of 2/6/1, the various reagents are mixed in the quantities stated below:

| | |
|---|---|
| Human insulin at 500 IU/mL | 20 mL |
| Solution of oligosaccharide 1 at 36.01 mg/mL | 20.27 mL |
| Solution 96.6 mM m-cresol/566 mM glycerin | 30 mL |
| Water | 28.95 mL |
| Polymer based on hyaluronic acid | 2190 mg |

For the polymer based on hyaluronic acid, it is possible to use the acid form or the basic form in the form of sodium salt, of potassium salt or of some other salt compatible with an injectable formulation.

The final pH is 7.4±0.4.

This clear solution is filtered on a 0.22 µm membrane and is then stored at +4° C.

B92. Preparation of a Solution of Human Insulin at 200 IU/mL.

60.4 g of water is added to 884.7 mg of human insulin comprising 2 $Zn^{2+}$ ions per hexamer, and the pH is then adjusted from 5.7 to 3 by adding 8 mL of 0.1 N solution of HCl. The solution is neutralized to pH 7 by adding 10 mL of 0.1 N solution of NaOH. The concentration is then adjusted to 200 IU/mL with 43.08 mL of water. The final pH of this solution is 7.02. The solution is finally filtered on a 0.22 µm membrane.

B93. Preparation of a Solution of Human Insulin at 200 IU/mL in the Presence of Oligosaccharide 2 at 14.6 mg/mL and 9.3 mM of Citrate.

For a final volume of 100 mL of formulation with a weight ratio (oligosaccharide 2/human insulin) of 2, the various reagents are mixed in the quantities stated below

| | |
|---|---|
| Human insulin at 200 IU/mL | 100 mL |
| Lyophilizate of oligosaccharide 2 | 1460 mg |
| Solution of sodium citrate at 1.188M | 1570 µL |

The final pH is adjusted to 7.4±0.4.

The clear solution is filtered on a 0.22 µm membrane and stored at 4° C.

B94. Preparation of a Solution of Human Insulin at 200 IU/mL in the Presence of Oligosaccharide 2 at 14.6 mg/mL and of Polyanionic Compound 1 at 14.6 mg/mL.

For a final volume of 100 mL of formulation with a weight ratio (oligosaccharide 2/polyanionic compound 1/human insulin) of 2/2/1, the various reagents are mixed in the quantities stated below

| | |
|---|---|
| Human insulin at 200 IU/mL | 100 mL |
| Lyophilizate of oligosaccharide 2 | 1460 mg |
| Lyophilizate of polyanionic compound 1 | 1460 mg |

The final pH is adjusted to 7.4±0.4.

The clear solution is filtered on a 0.22 µm membrane and stored at 4° C.

B95. Preparation of a Solution of Human Insulin at 200 IU/mL in the Presence of Oligosaccharide 2 at 14.6 mg/mL and of Polyanionic Compound 1 at 29.2 mg/mL.

For a final volume of 100 mL of formulation with a weight ratio [oligosaccharide 2/polyanionic compound 1/human insulin] of 2/4/1, the various reagents are mixed in the quantities stated below

| | |
|---|---|
| Human insulin at 200 IU/mL | 100 mL |
| Lyophilizate of oligosaccharide 2 | 1460 mg |
| Lyophilizate of polyanionic compound 1 | 2920 mg |

The final pH is adjusted to 7.4±0.4.

The clear solution is filtered on a 0.22 µm membrane and stored at 4° C.

B96. Preparation of a Solution of Human Insulin at 100 IU/mL in the Presence of Oligosaccharide 3 at 7.3 mg/mL.

For a final volume of 100 mL of formulation with a weight ratio [oligosaccharide 3/human insulin] of 2/1, the various reagents are mixed in the quantities stated below

| | |
|---|---|
| Human insulin at 500 IU/mL | 20 mL |
| Oligosaccharide 3 at 27.71 mg/mL | 28.4 mL |
| 96.6 mM m-cresol/566 mM glycerol | 30 mL |
| Water (volume for dilution − volume of sodium hydroxide) | 21.6 mL |

The final pH is adjusted to 7.0±0.3.

The clear solution is filtered on a 0.22 µm membrane and stored at 4° C.

This formulation is referenced example 18 in the priority document.

C. Pharmacodynamics and Pharmacokinetics

C1. Protocol for Measuring the Pharmacodynamics of the Insulin Solutions.

12 domestic pigs of about 50 kg, previously catheterized in the jugular, are fasted for 2.5 hours before the start of the experiment. In the hour preceding the injection of insulin, 3 blood samples are taken for determining the baseline glucose level.

Human insulin at a dose of 0.125 IU/kg (or 0.09 IU/kg for the insulin analog) is injected subcutaneously in the neck, under the animal's ear using a Novopen insulin pen fitted with a 31 G needle.

Blood samples are then taken every 4 minutes for 20 min and then every 10 minutes up to 3 hours. After each sampling, the catheter is rinsed with a dilute heparin solution.

A drop of blood is taken for determining glycemia using a glucometer.

The curves of glucose pharmacodynamics are then plotted and the time taken to reach the minimum blood glucose level for each pig is determined and reported as Tmin glucose. The mean value of the Tmin glucose values is then calculated.

The remaining blood is collected in a dry tube and centrifuged to isolate the serum. The insulin levels in the serum samples are measured by Elisa Sandwich immunoassay for each pig.

The pharmacokinetic curves are then plotted. The time taken to reach the peak insulin concentration in the serum for each pig is determined and reported as Tmax insulin. The mean value of the Tmax insulin values is then calculated.

C2. Results for Pharmacodynamics and Pharmacokinetics of the Insulin Solutions from Examples B1 and B3.

| Example | Insulin | Oligosaccharide | Excipient | Dose (IU/kg) | Number of pigs |
|---------|---------|-----------------|-----------|--------------|----------------|
| B1 | Aspart | — | — | 0.125 | 11 |
| B3 | Human | — | — | 0.125 | 11 | described in examples B1 and B3 are presented in FIG. 1. Analysis of these curves shows that the formulation of human insulin (curve plotted with squares corresponding to example B3, Tmin glucose=61±31 min) does indeed have a slower action than the commercial formulation of insulin aspart (curve plotted with triangles corresponding to example B1, Tmin glucose=44±13 min).

Figure 2:
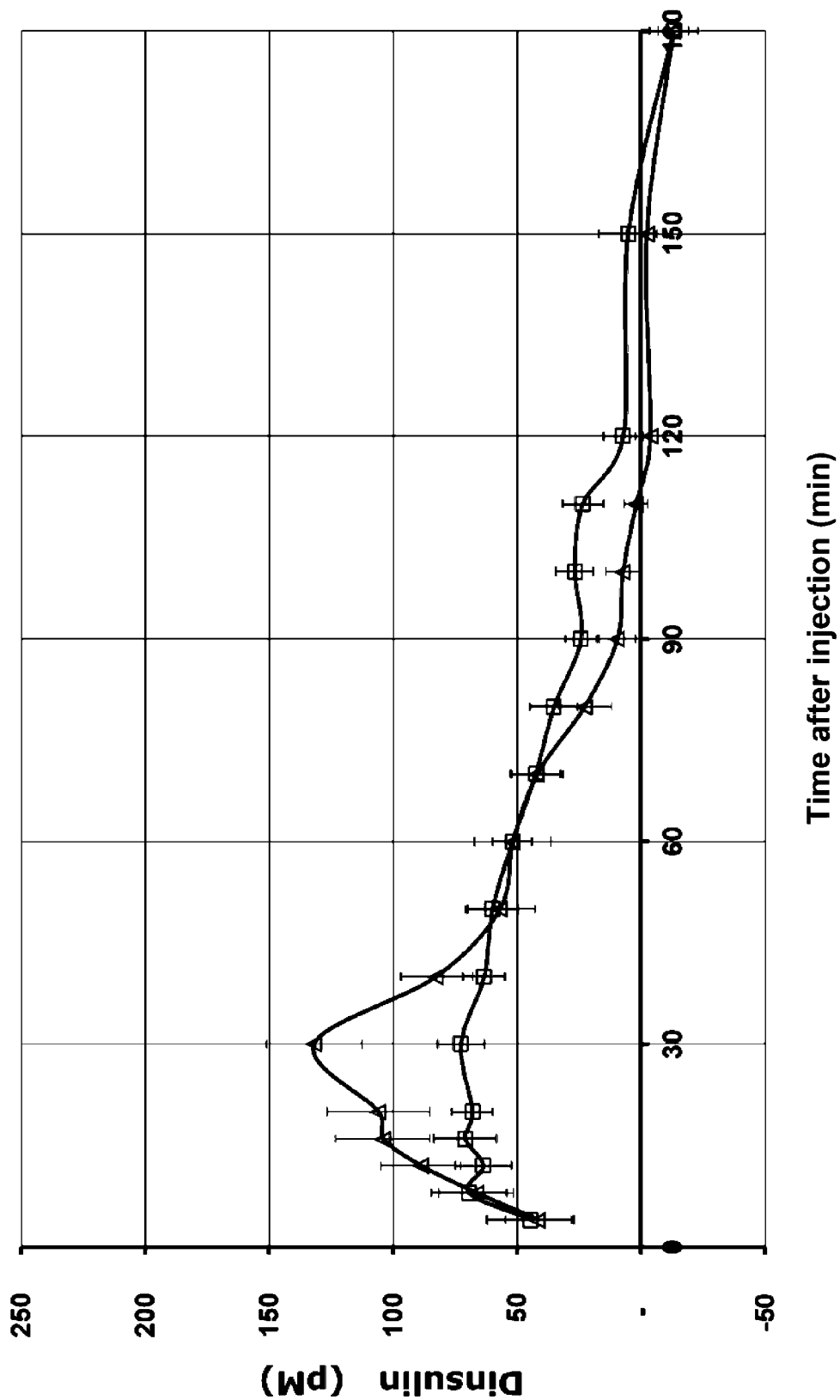
FIG. 2: the curves show that the formulation of human insulin alone (curve plotted with squares corresponding to example B3, Tmax insulin=36±33 min) induces slower absorption than the commercial formulation of insulin aspart (Novolog®) (curve plotted with triangles corresponding to example B1, Tmax insulin=28±13 min).

The results for pharmacokinetics obtained with the formulations described in examples B1 and B3 are presented in FIG. 2. Analysis of these curves shows that the formulation of human insulin alone (curve plotted with squares corresponding to example B3, Tmax insulin=36±33 min) does indeed induce slower absorption than the commercial formulation of insulin aspart (Novolog®) (curve plotted with triangles corresponding to example B1, Tmax insulin=28±13 min). These results are in agreement with those in the literature with an acceleration of a rapid-acting insulin analog relative to a human insulin and therefore validate the suitability of the model for the problem of measuring the acceleration of an insulin.

C3. Results for Pharmacodynamics and Pharmacokinetics of the Insulin Solutions from Examples B1 and B6.

| Example | Insulin | Oligosaccharide | Excipient | Dose IU/kg | Number of pigs |
|---------|---------|-----------------|-----------|------------|----------------|
| B1 | Aspart | — | — | 0.125 | 16 |
| B6 | Human | 2 | Polyanionic compound 1 7.3 mg/mL | 0.125 | 8 |

Figure 3:
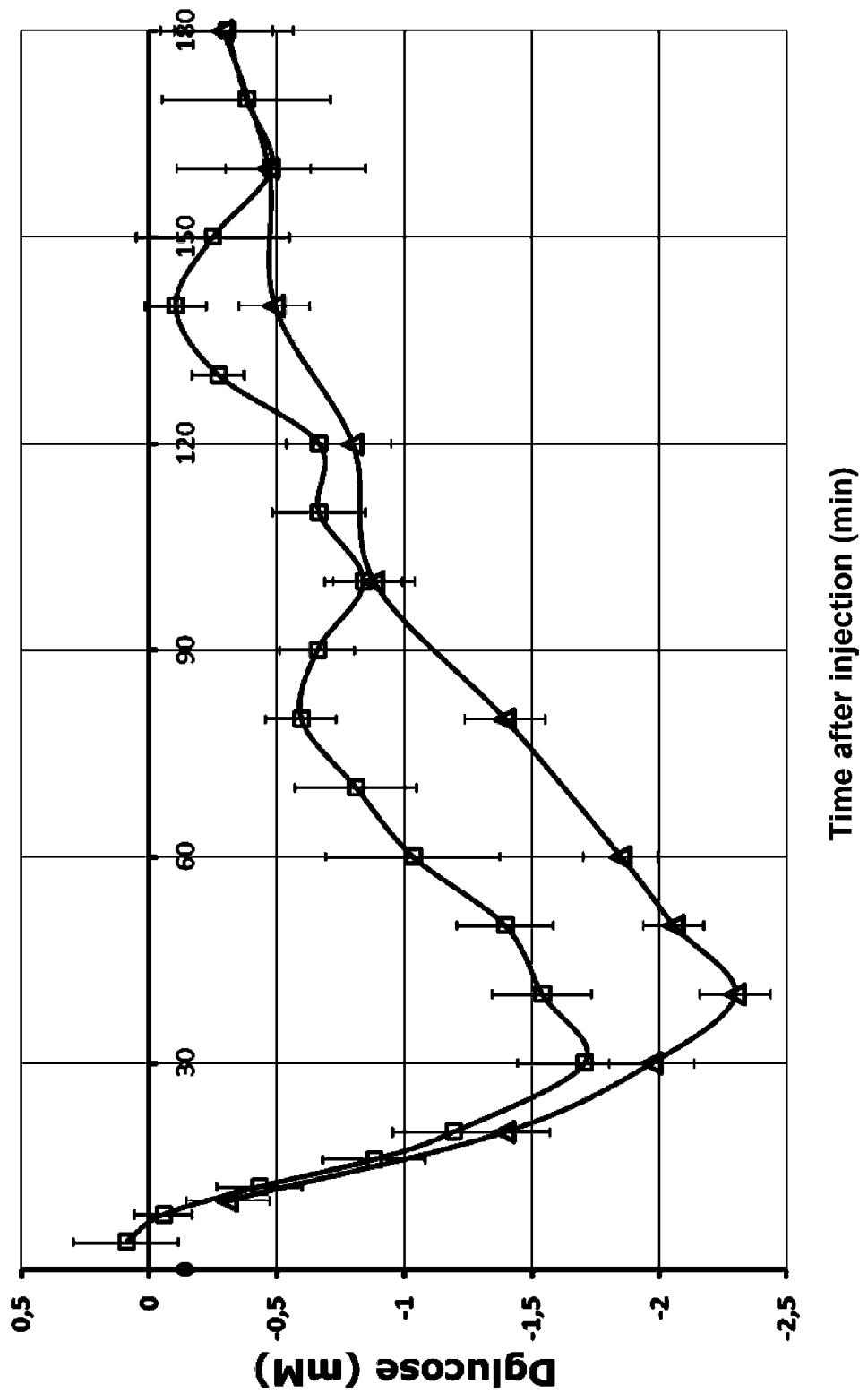
FIG. 3: the curves show that the formulation based on human insulin comprising oligosaccharide 2 and polyanionic compound 1 as excipient at 7.3 mg/mL (curve plotted with squares corresponding to example B6, Tmin glucose=39±11 min) has an action as rapid as that of the commercial formulation of insulin aspart (Novolog®) (curve plotted with triangles corresponding to example B1, Tmin glucose=41±9 min).

The results for pharmacodynamics obtained with the formulations described in examples B1 and B6 are presented in FIG. 3. Analysis of these curves shows that the formulation based on human insulin comprising oligosaccharide 2 and polyanionic compound 1 as excipient at 7.3 mg/mL (curve plotted with squares corresponding to example B6, Tmin glucose=39±11 min) makes it possible to obtain an action as rapid as that of the commercial formulation of insulin aspart (Novolog®) (curve plotted with triangles corresponding to example B1, Tmin glucose=41±9 min).

Figure 4:
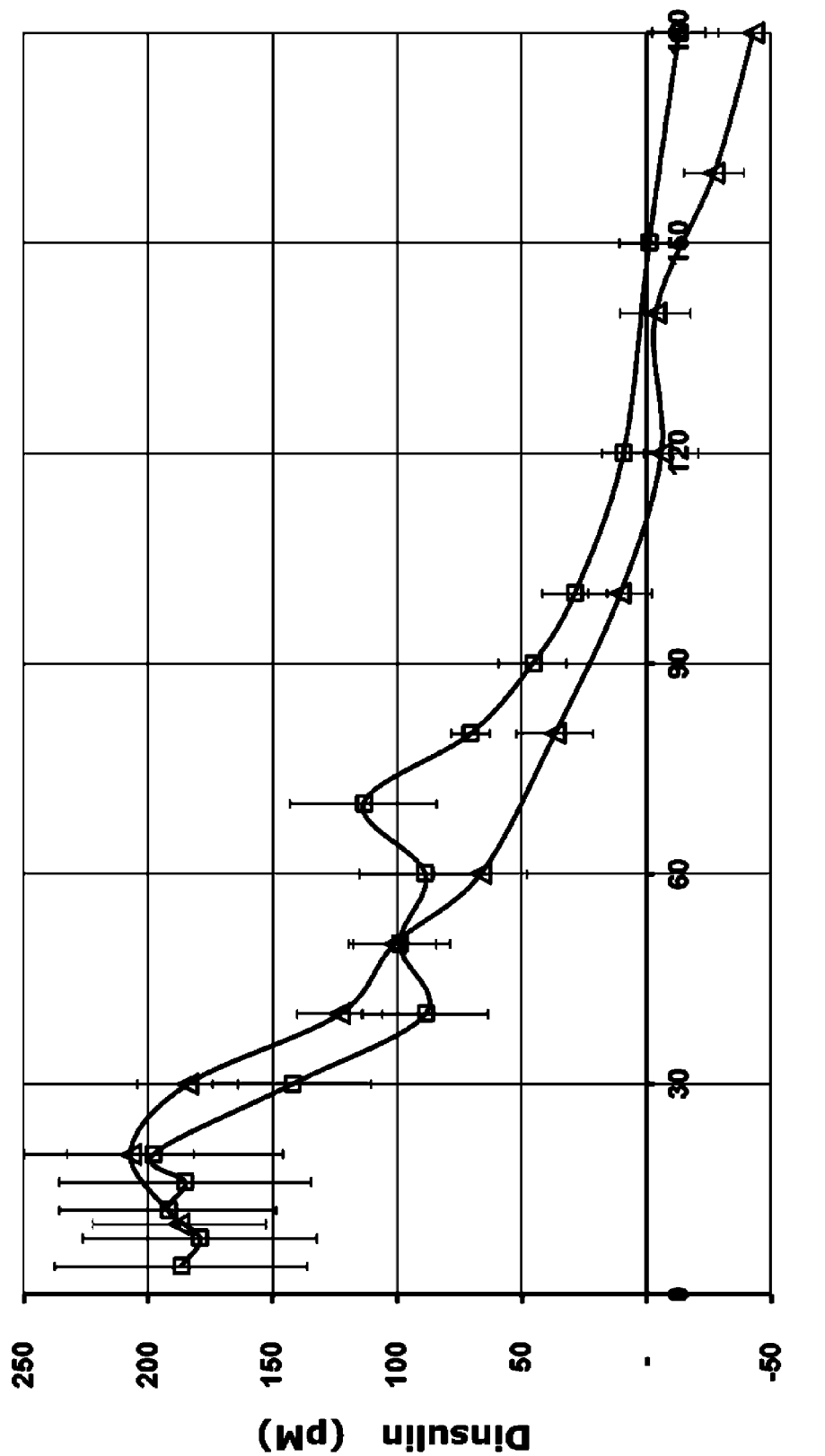
FIG. 4: the curves show that the formulation based on human insulin comprising oligosaccharide 2 and polyanionic compound 1 as excipients at 7.3 mg/mL (curve plotted with squares corresponding to example B6, Tmax insulin=14±9 min) induces an absorption that is more rapid than the commercial formulation of insulin aspart (Novolog®) (curve plotted with triangles corresponding to example B1, Tmax insulin=24±13 min).

The results for pharmacokinetics obtained with the formulations described in examples B1 and B6 are presented in FIG. 4. Analysis of these curves shows that the formulation based on human insulin comprising oligosaccharide 2 and polyanionic compound 1 as excipients at 7.3 mg/mL (curve plotted with squares corresponding to example B6, Tmax insulin=14±9 min) induces an absorption that is more rapid than the commercial formulation of insulin aspart (Novo-loge) (curve plotted with triangles corresponding to example B1, Tmax insulin=24±13 min). As the time parameters of insulin aspart between examples C2 and C3 are similar, it can be deduced from this by extrapolation that the formulation of example B6 also induces an acceleration relative to the human insulin (example B3).

C4. Results for Pharmacodynamics and Pharmacokinetics of the Insulin Solutions from Examples B1 and B7

| Example | Insulin | Oligosaccharide | Excipient | Dose IU/kg | Number of pigs |
|---------|---------|-----------------|-----------|------------|----------------|
| B1 | Aspart | — | — | 0.125 | 14 |
| B7 | Human | 2 | Citrate 9.3 mM | 0.125 | 12 |

Figure 5:
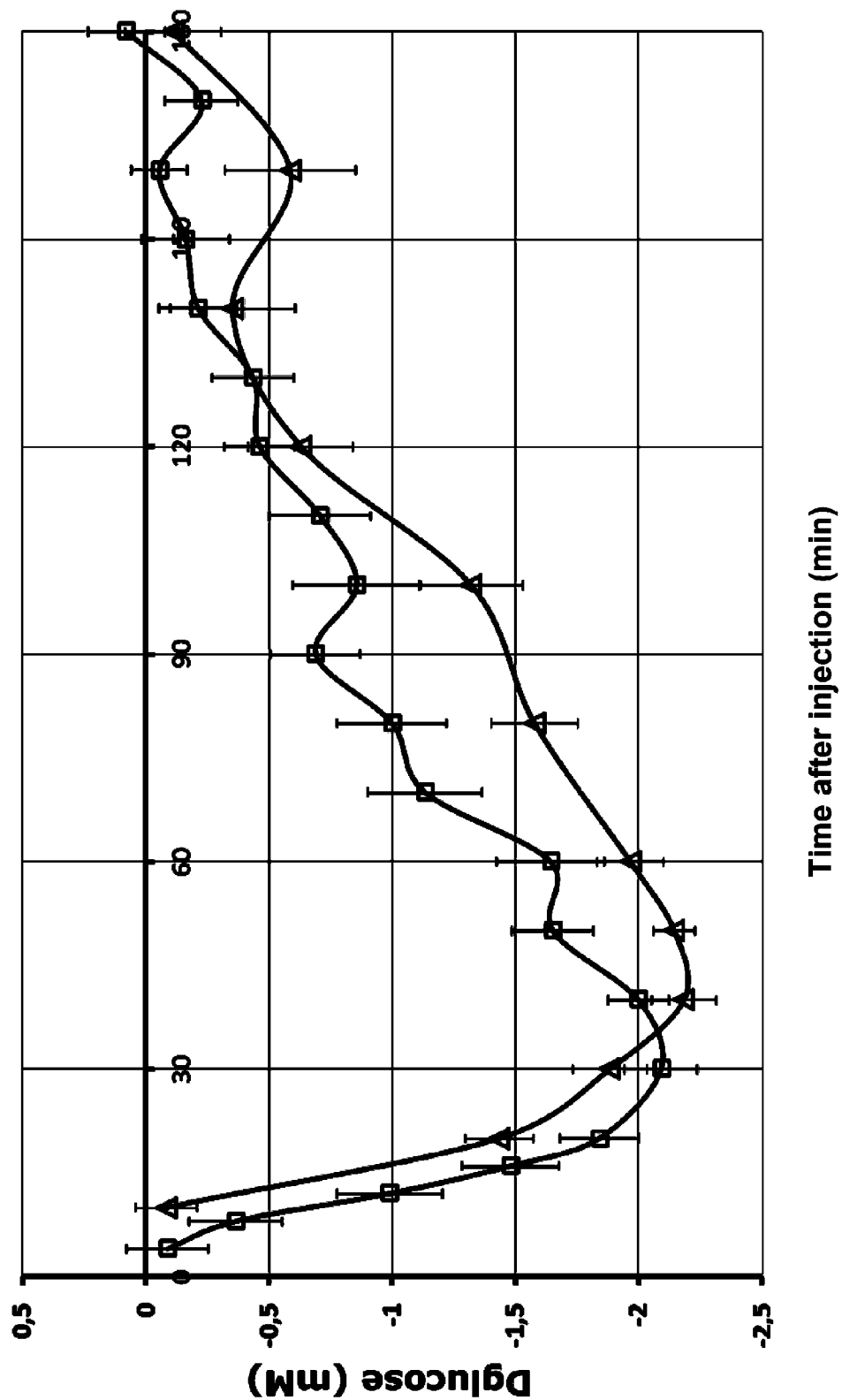
FIG. 5: the curves show that the formulation based on human insulin comprising oligosaccharide 2 and citrate at 9.3 mM as excipients (curve plotted with squares corresponding to example B7, Tmin glucose=36±14 min) has a more rapid action than that of the commercial formulation of insulin aspart (Novolog®) (curve plotted with triangles corresponding to example B1, Tmin glucose=53±24 min).

The results for pharmacodynamics obtained with the formulations described in examples B1 and B7 are presented in FIG. 5. Analysis of these curves shows that the formulation based on human insulin comprising oligosaccharide 2 and citrate at 9.3 mM as excipients (curve plotted with squares corresponding to example B7, Tmin glucose=36±14 min) makes it possible to obtain a more rapid action than that of the commercial formulation of insulin aspart (Novolog®) (curve plotted with triangles corresponding to example B1, Tmin glucose=53±24 min).

Figure 6:
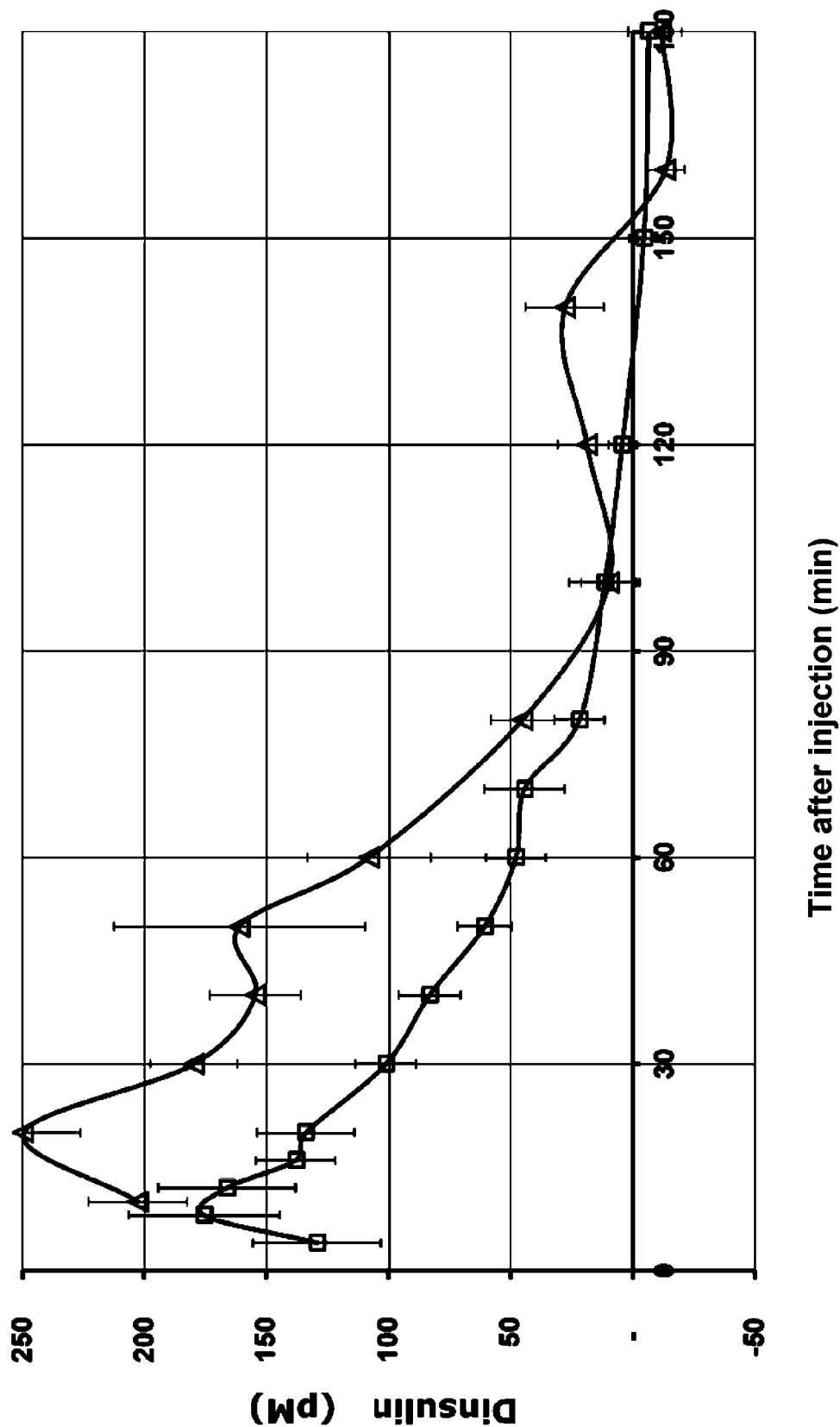
FIG. 6: the curves show that the formulation comprising oligosaccharide 2 and citrate at 9.3 mM as excipients (curve plotted with squares corresponding to example B7, Tmax insulin=15±10 min) induces an absorption that is more rapid than the commercial formulation of insulin aspart (Novolog®) (curve plotted with triangles corresponding to example B1, Tmax insulin=22±10 min).

The results for pharmacokinetics obtained with the formulations described in examples B1 and B7 are presented in FIG. 6. Analysis of these curves shows that the formulation comprising oligosaccharide 2 and citrate at 9.3 mM as excipients (curve plotted with squares corresponding to example B7, Tmax insulin=15±10 min) induces an absorption that is more rapid than the commercial formulation of insulin aspart (Novolog®) (curve plotted with triangles corresponding to example B1, Tmax insulin=22±10 min). As the time parameters of insulin aspart (Novolog®) between examples C2 and C4 are similar, it can be deduced from this by extrapolation that the formulation of example B7 also induces an acceleration relative to the human insulin (example B3).

C5. Results for Pharmacodynamics and Pharmacokinetics of the Insulin Solutions from Examples B2 and B9

| Example | Insulin | Oligosaccharide | Excipient | Dose IU/kg | Number of pigs |
|---------|---------|-----------------|-----------|------------|----------------|
| B2 | Lispro | — | — | 0.09 | 23 |
| B9 | Lispro | 2 | Citrate 9.3 mM | 0.09 | 12 |

Figure 7:
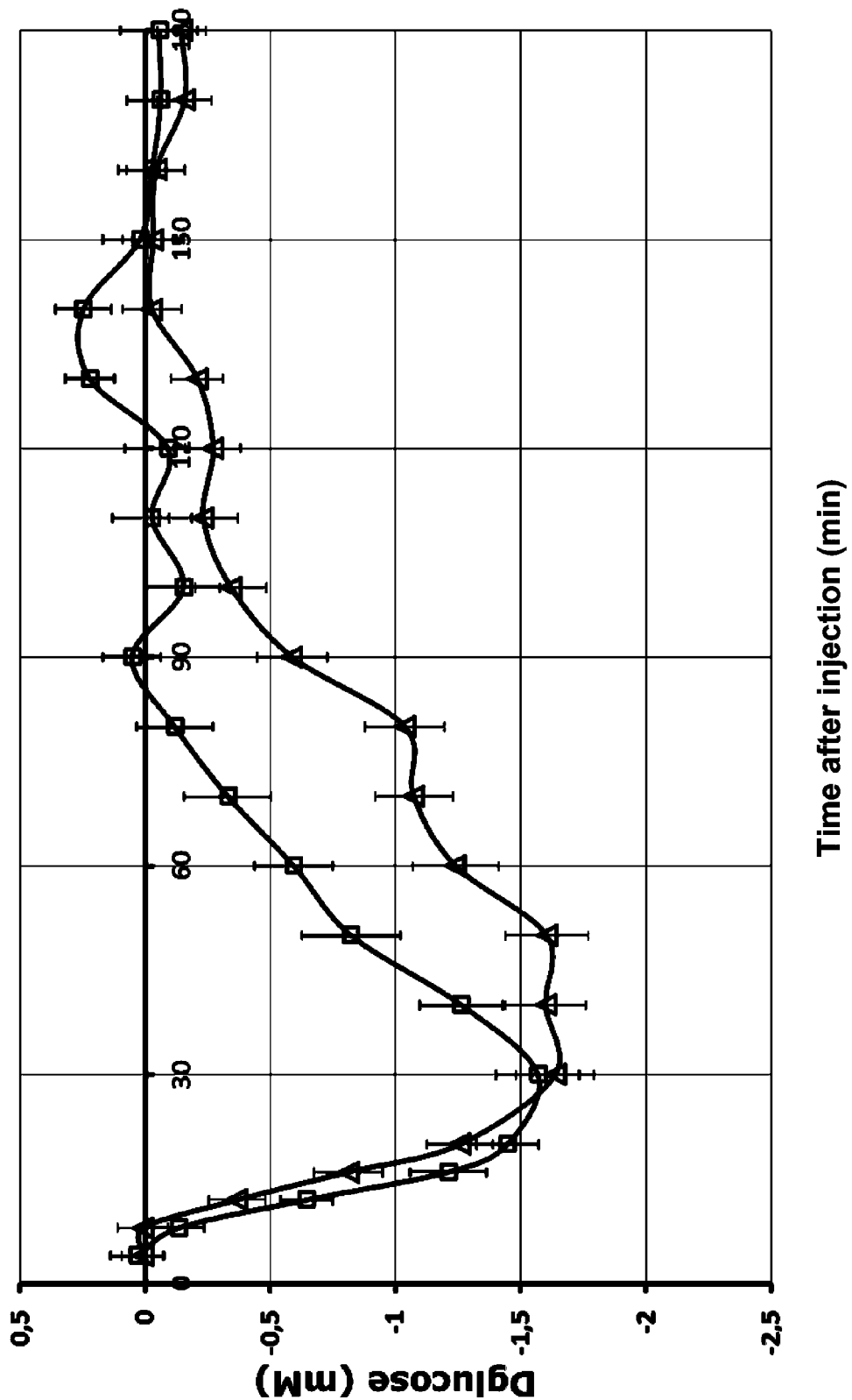
FIG. 7: the curves show that the formulation based on insulin lispro (Humalog®) comprising oligosaccharide 2 and citrate at 9.3 mM as excipients (curve plotted with squares corresponding to example B9, Tmin glucose=32±9 min) has a more rapid action than that of the commercial formulation of insulin lispro (Humalog®) (curve plotted with triangles corresponding to example B2, Tmin glucose=45±16 min).

The results for pharmacodynamics obtained with the formulations described in examples B2 and B9 are presented in FIG. 7. Analysis of these curves shows that the formulation based on insulin lispro (Humalog®) comprising oligosaccharide 2 and citrate at 9.3 mM as excipients (curve plotted with squares corresponding to example B9, Tmin glucose=32±9 min) makes it possible to obtain a more rapid action than that of the commercial formulation of insulin lispro (Humalog®) (curve plotted with triangles corresponding to example B2, Tmin glucose=45±16 min).

Figure 8:
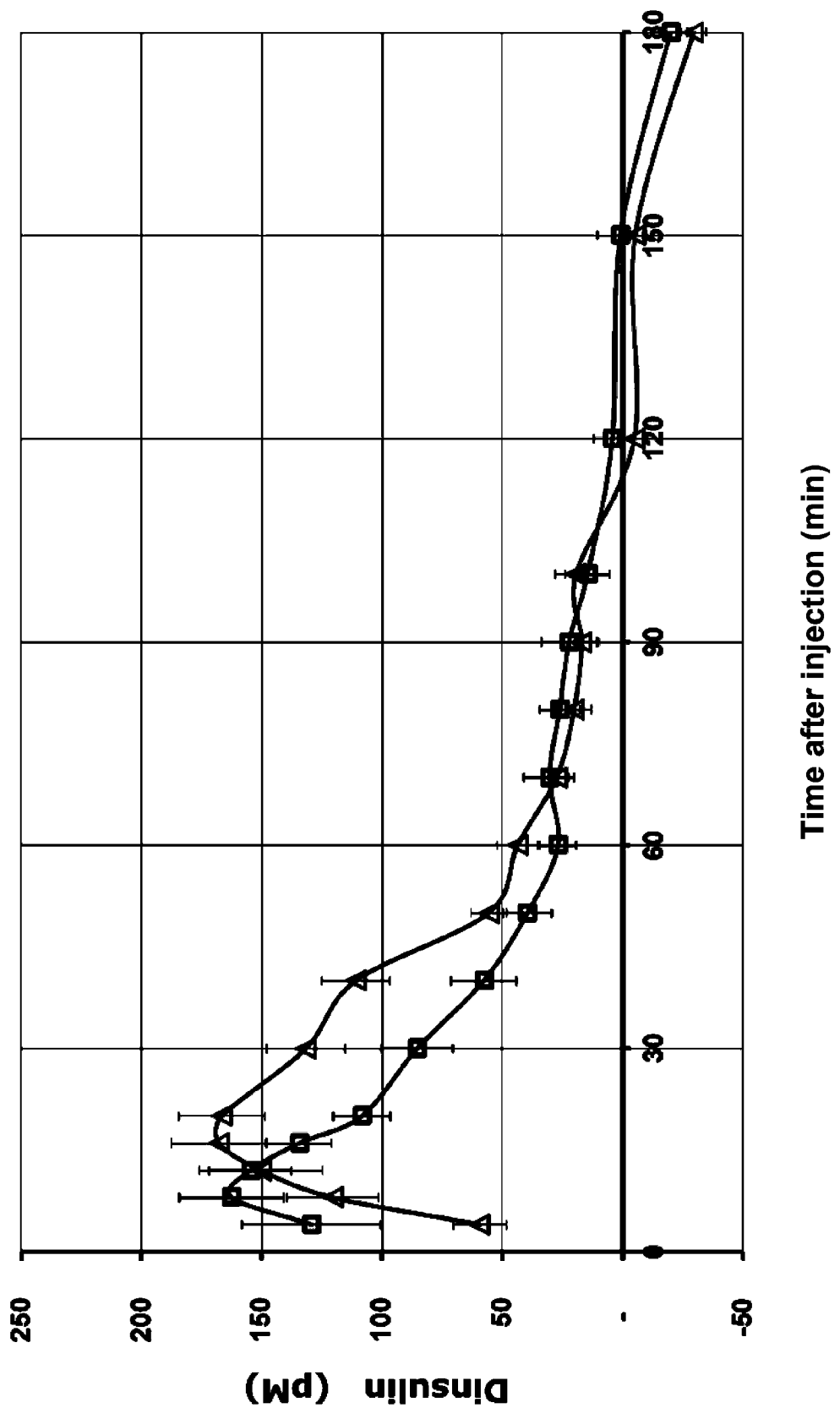
FIG. 8: the curves show that the formulation based on Humalog® comprising oligosaccharide 2 and citrate at 9.3 mM as excipient (curve plotted with squares corresponding to example B9, Tmax insulin=12±7 min) induces an absorption that is more rapid than the commercial formulation of insulin lispro (Humalog®) (curve plotted with triangles corresponding to example B2, Tmax insulin=19±10 min).

The results for pharmacokinetics obtained with the formulations described in examples B2 and B9 are presented in FIG. 8. According to the invention, analysis of these curves shows that the formulation based on Humalog® comprising oligosaccharide 2 and citrate at 9.3 mM as excipient (curve plotted with squares corresponding to example B9, Tmax insulin=12±7 min) induces an absorption that is more rapid than the commercial formulation of insulin lispro (Humalog®) (curve plotted with triangles corresponding to example B2, Tmax insulin=19±10 min).

C6. Results for Pharmacodynamics and Pharmacokinetics of the Insulin Solutions from Examples B2 and B10

| Example | Insulin | Oligosac-charide | Excipient | Dose IU/kg | Number of pigs |
|---|---|---|---|---|---|
| B2 | Lispro | — | — | 0.09 | 11 |
| B10 | Lispro | 2 | Citrate 6 mM | 0.09 | 10 |

Figure 9:
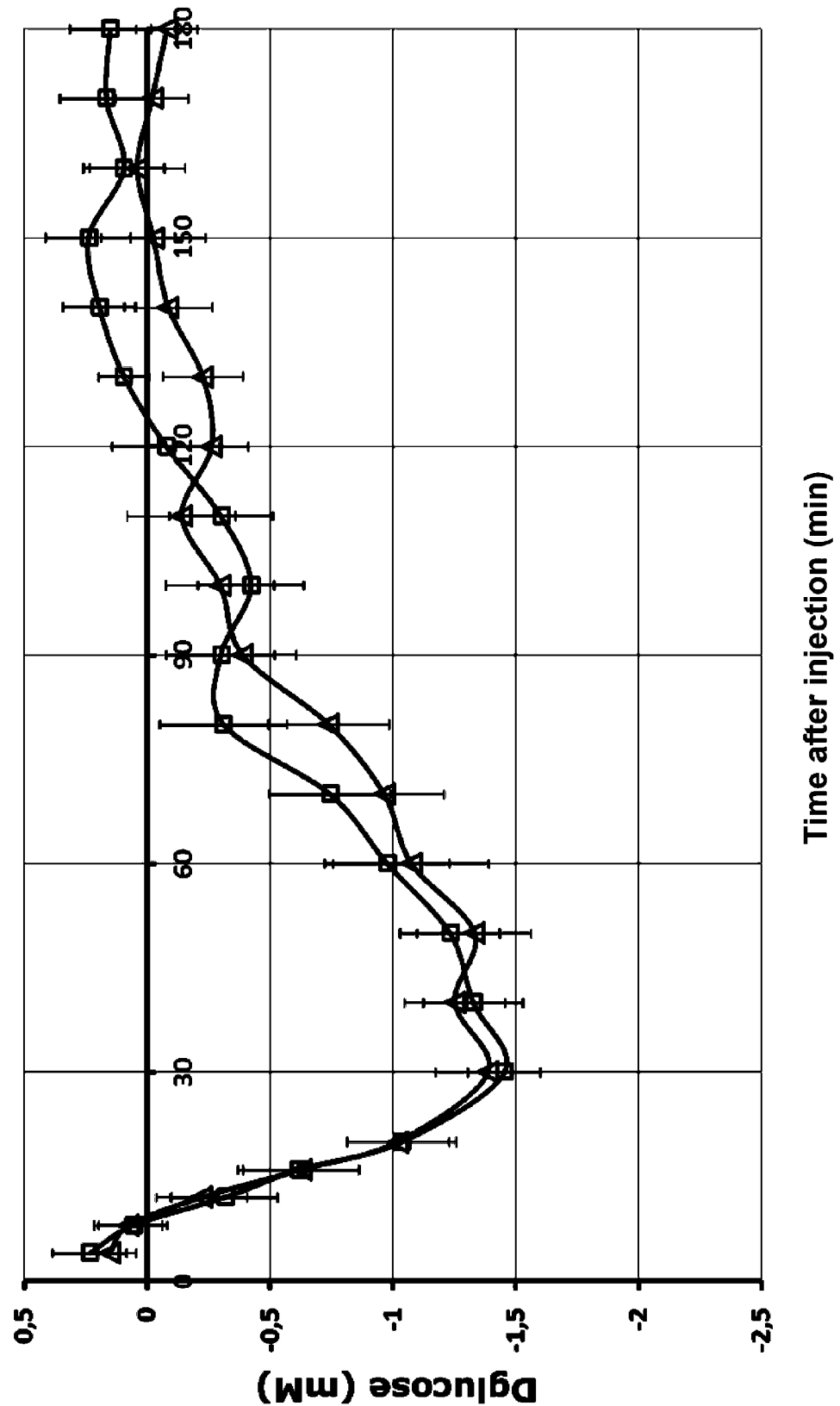
FIG. 9: the curves show that the formulation based on insulin lispro (Humalog®) comprising oligosaccharide 2 and citrate at 6 mM as excipients (curve plotted with squares corresponding to example B10, Tmin glucose=34±12 min) has a more rapid action than that of the commercial formulation of insulin lispro (Humalog®) (curve plotted with triangles corresponding to example B2, Tmin glucose=44±14 min).

The results for pharmacodynamics obtained with the formulations described in examples B2 and B10 are presented in FIG. 9. Analysis of these curves shows that the formulation based on insulin lispro (Humalog®) comprising oligosaccharide 2 and citrate at 6 mM as excipients (curve plotted with squares corresponding to example B10, Tmin glucose=34±12 min) makes it possible to obtain a more rapid action than that of the commercial formulation of insulin lispro (Humalog®) (curve plotted with triangles corresponding to example B2, Tmin glucose=44±14 min).

Figure 10:
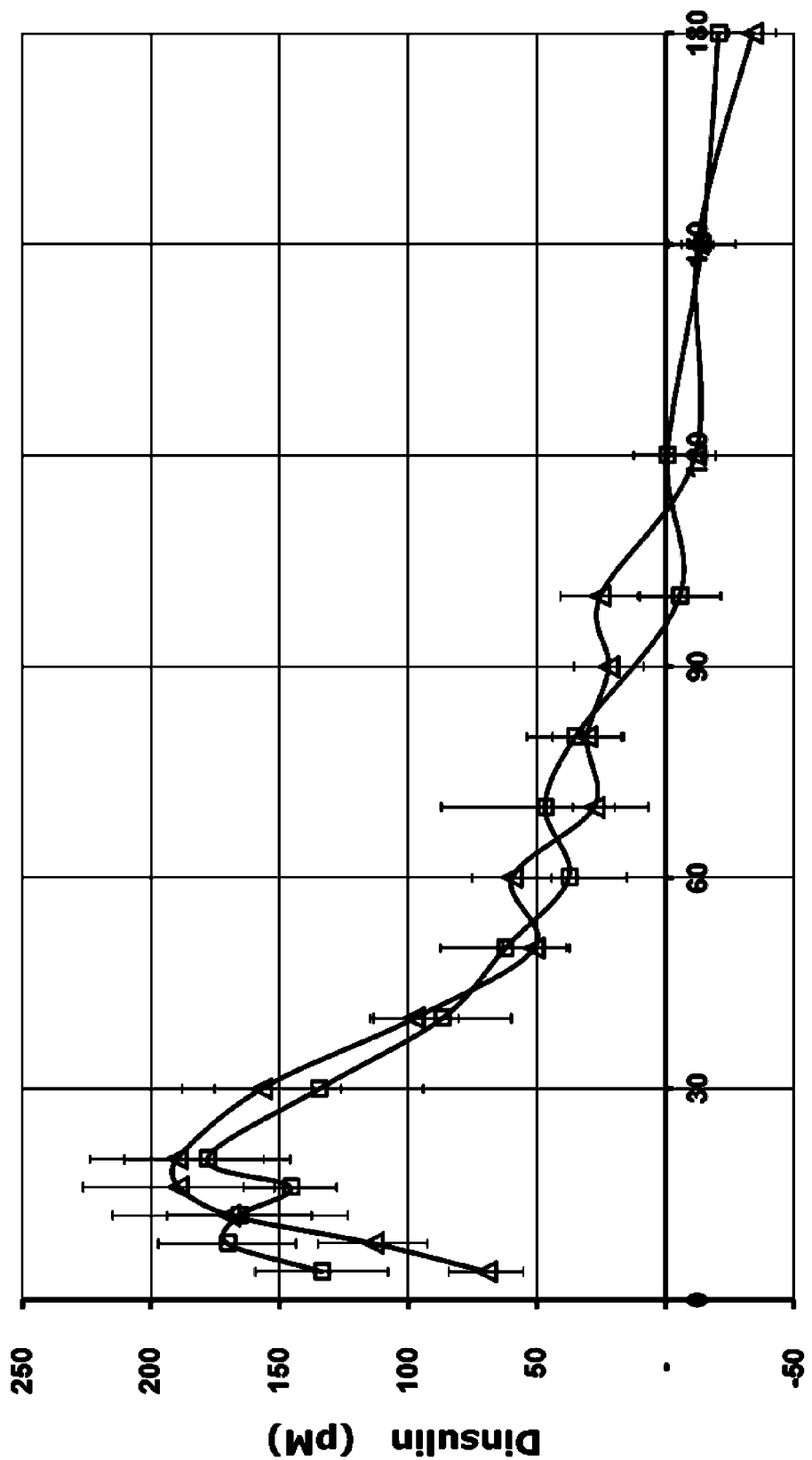
FIG. 10: the curves show that the formulation based on insulin lispro (Humalog®) comprising oligosaccharide 2 and citrate at 6 mM as excipients (curve plotted with squares corresponding to example B10, Tmax insulin=13±8 min) induces an absorption that is more rapid than the commercial formulation of insulin lispro (Humalog®) (curve plotted with triangles corresponding to example B2, Tmax insulin=18±8 min).

The results for pharmacokinetics obtained with the formulations described in examples B2 and B10 are presented in FIG. 10. Analysis of these curves shows that the formulation based on insulin lispro (Humalog®) comprising oligosaccharide 2 and citrate at 6 mM as excipients (curve plotted with squares corresponding to example B10, Tmax insulin=13±8 min) induces an absorption that is more rapid than the commercial formulation of insulin lispro (Humalog®) (curve plotted with triangles corresponding to example B2, Tmax insulin 18±8 min).

C7. Results for Pharmacodynamics and Pharmacokinetics of the Insulin Solutions from Examples B2 and B11.

| Example | Insulin | Oligosac-charide | Excipient | Dose IU/kg | Number of pigs |
|---|---|---|---|---|---|
| B2 | Lispro | — | — | 0.09 | 11 |
| B11 | Lispro | 1 | Citrate 9.3 mM | 0.09 | 11 |

Figure 11:
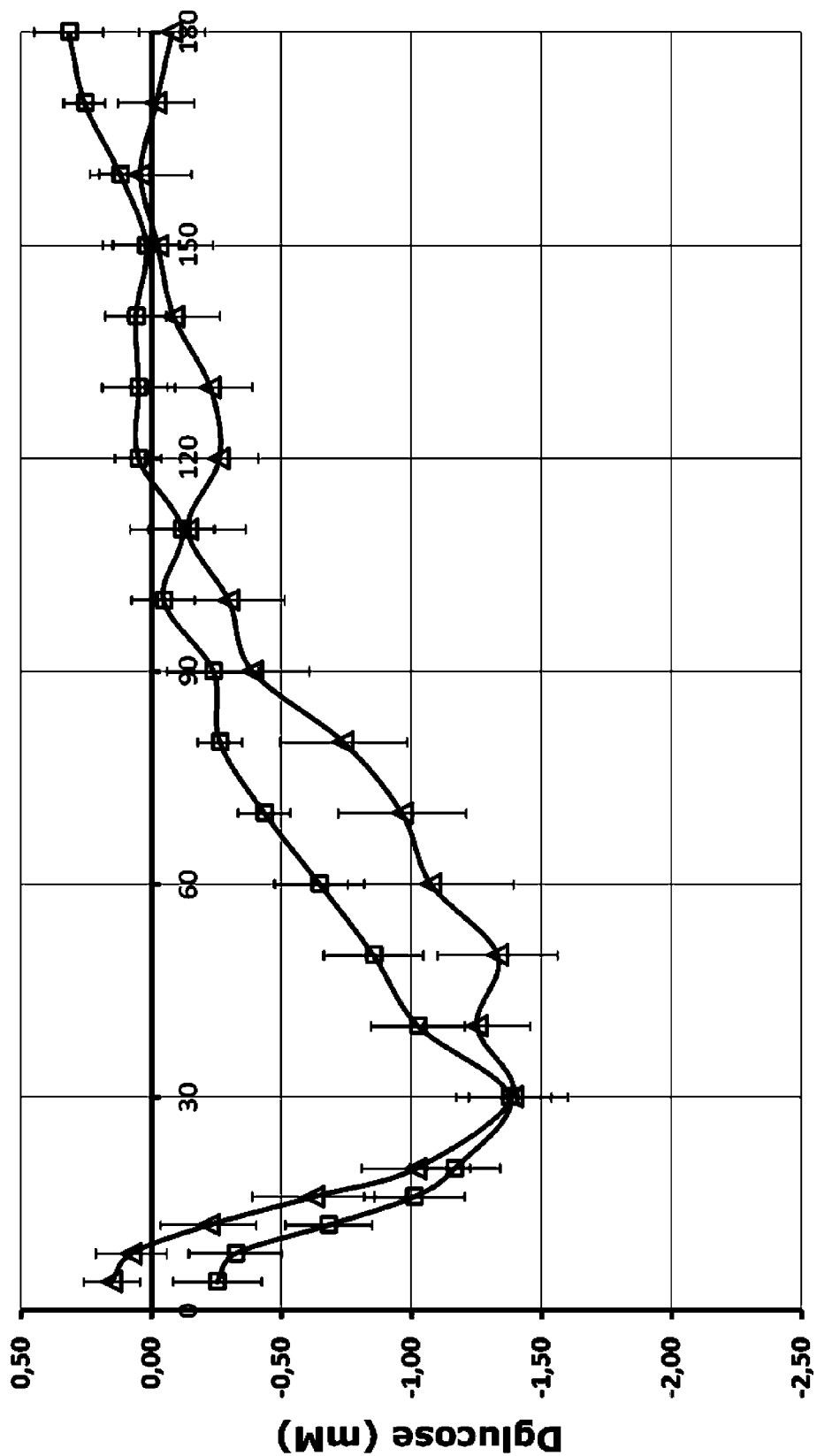
FIG. 11: the curves show that the formulation based on insulin lispro (Humalog®) comprising oligosaccharide 1 and citrate at 9.3 mM as excipients (curve plotted with squares corresponding to example B11, Tmin glucose=31±14 min) has a more rapid action than that of the commercial formulation of insulin lispro (Humalog®) (curve plotted with triangles corresponding to example B2, Tmin glucose=44±14 min).

The results for pharmacodynamics obtained with the formulations described in examples B2 and B11 are presented in FIG. 11. Analysis of these curves shows that the formulation based on insulin lispro (Humalog®) comprising oligosaccharide 1 and citrate at 9.3 mM as excipients (curve plotted with squares corresponding to example B11, Tmin glucose=31±14 min) makes it possible to obtain a more rapid action than that of the commercial formulation of insulin lispro (Humalog®) (curve plotted with triangles corresponding to example B2, Tmin glucose=44±14 min).

Figure 12:
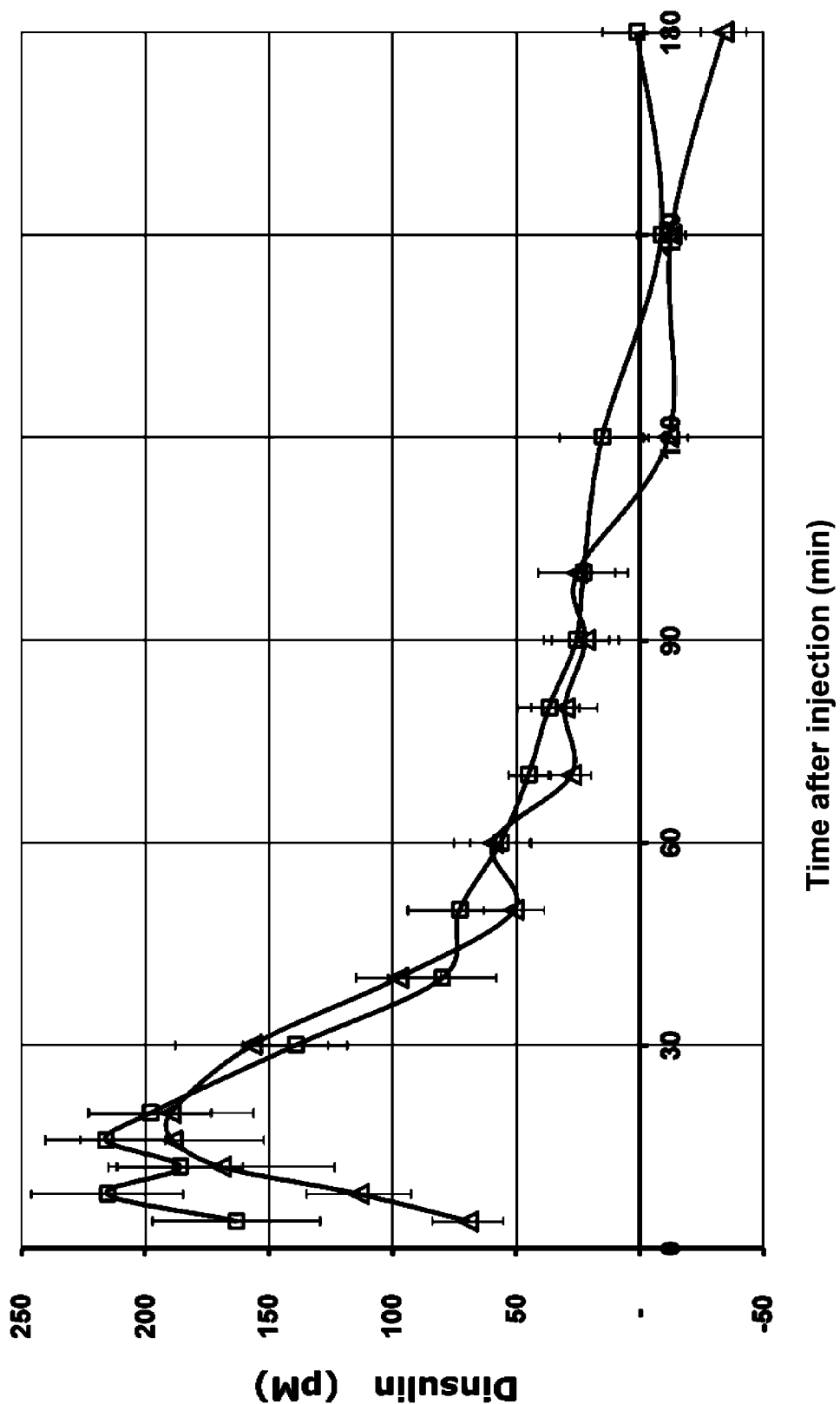
FIG. 12: the curves show that the formulation based on insulin lispro (Humalog®) comprising oligosaccharide 1 and citrate at 9.3 mM as excipients (curve plotted with squares corresponding to example B11, Tmax insulin=15±7 min) induces an absorption that is more rapid than the commercial formulation of insulin lispro (Humalog®) (curve plotted with triangles corresponding to example B2, Tmax insulin=18±8 min).

The results for pharmacokinetics obtained with the formulations described in examples B2 and B11 are presented in FIG. 12. Analysis of these curves shows that the formulation based on insulin lispro (Humalog®) comprising oligosaccharide 1 and citrate at 9.3 mM as excipients (curve plotted with squares corresponding to example B11, Tmax insulin=15±7 min) induces an absorption that is more rapid than the commercial formulation of insulin lispro (Humalog®) (curve plotted with triangles corresponding to example B2, Tmax insulin=18±8 min).

C8. Results for Pharmacodynamics and Pharmacokinetics of the Insulin Solutions from Examples B2 and B12.

| Example | Insulin | Oligosac-charide | Excipient | Dose IU/kg | Number of pigs |
|---|---|---|---|---|---|
| B2 | Lispro | — | — | | 9 |
| B12 | Lispro | 1 | Citrate 18.6 mM | 0.09 | 11 |

Figure 13:
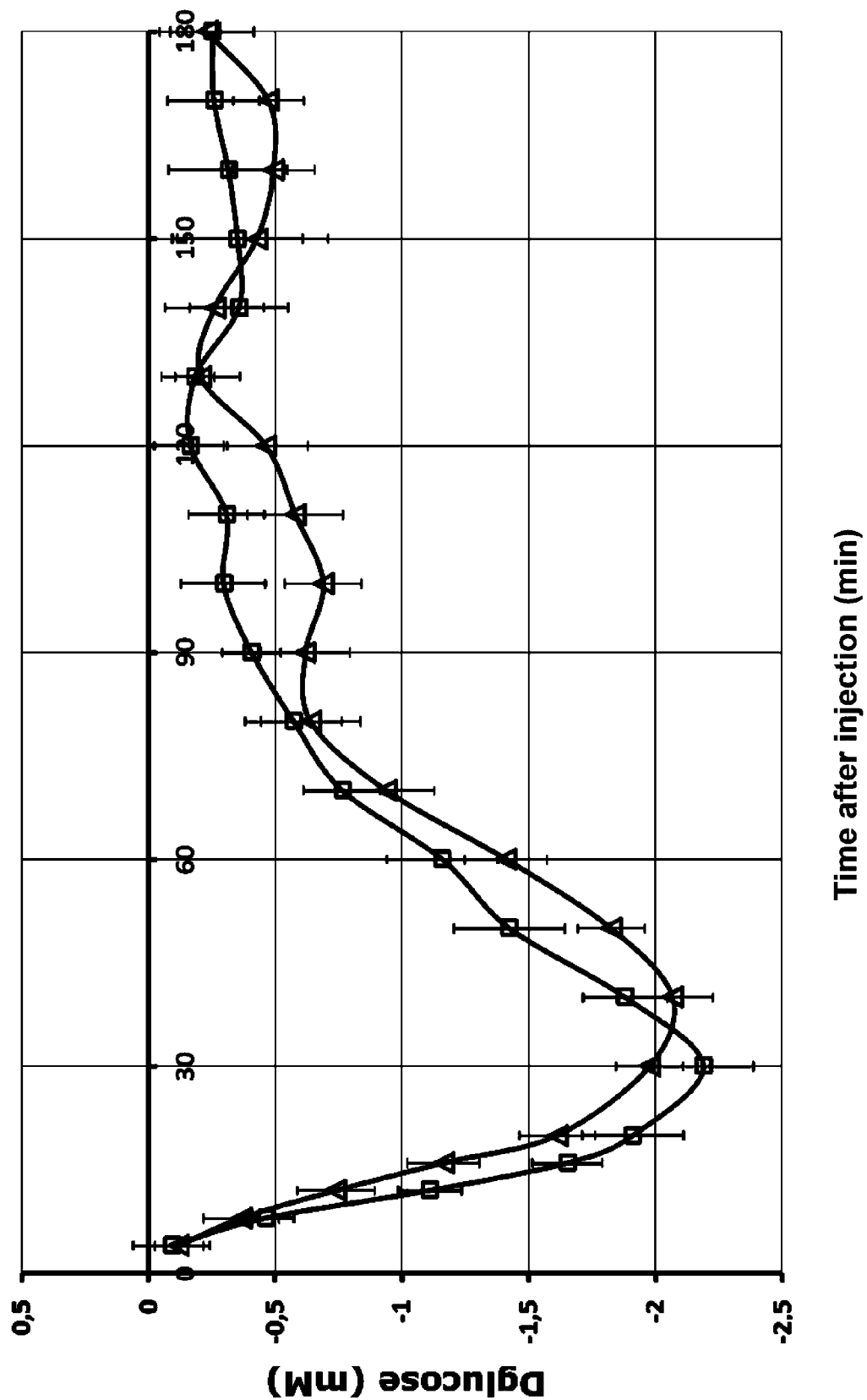
FIG. 13: the curves show that the formulation based on insulin lispro (Humalog®) comprising oligosaccharide 1 and citrate at 18.6 mM as excipients (curve plotted with squares corresponding to example B12, Tmin glucose=30±5 min) has a more rapid action than that of the commercial formulation of insulin lispro (Humalog®) (curve plotted with triangles corresponding to example B2, Tmin glucose=40±12 min).

The results for pharmacodynamics obtained with the formulations described in examples B2 and B12 are presented in FIG. 13. Analysis of these curves shows that the formulation based on insulin lispro (Humalog®) comprising oligosaccharide 1 and citrate at 18.6 mM as excipients (curve plotted with squares corresponding to example B12, Tmin glucose=30±5 min) makes it possible to obtain a more rapid action than that of the commercial formulation of insulin lispro (Humalog®) (curve plotted with triangles corresponding to example B2, Tmin glucose=40±12 min).

Figure 14:
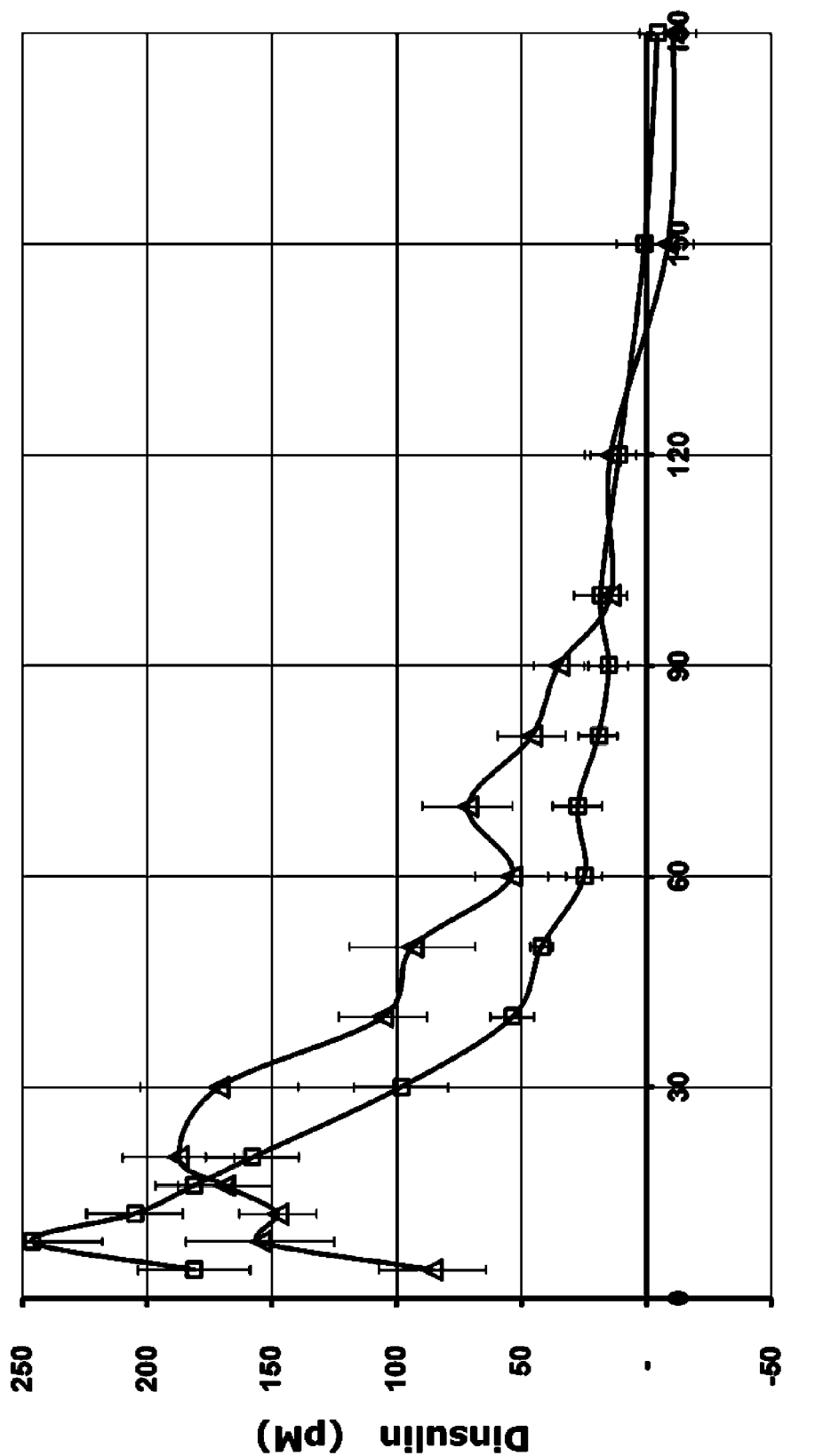
FIG. 14: the curves show that the formulation based on insulin lispro (Humalog®) comprising oligosaccharide 1 and citrate at 18.6 mM as excipients (curve plotted with squares corresponding to example B11, Tmax insulin=10±4 min) induces an absorption that is more rapid than the commercial formulation of insulin lispro (Humalog®) (curve plotted with triangles corresponding to example B2, Tmax insulin=23±12 min).

The results for pharmacokinetics obtained with the formulations described in examples B2 and B12 are presented in FIG. 14. Analysis of these curves shows that the formulation based on insulin lispro (Humalog®) comprising oligosaccharide 1 and citrate at 18.6 mM as excipients (curve plotted with squares corresponding to example B11, Tmax insulin=10±4 min) induces an absorption that is more rapid than the commercial formulation of insulin lispro (Humalog®) (curve plotted with triangles corresponding to example B2, Tmax insulin=23±12 min).

C9. Results for Pharmacodynamics and Pharmacokinetics of the Insulin Solutions from Examples B2 and B13.

| Example | Insulin | Oligosac-charide | Excipient | Dose IU/kg | Number of pigs |
|---|---|---|---|---|---|
| B2 | Lispro | — | — | 0.09 | 9 |
| B13 | Lispro | 2 | Polyanionic compound 1 7.3 mg/mL | 0.09 | 11 |

Figure 15:
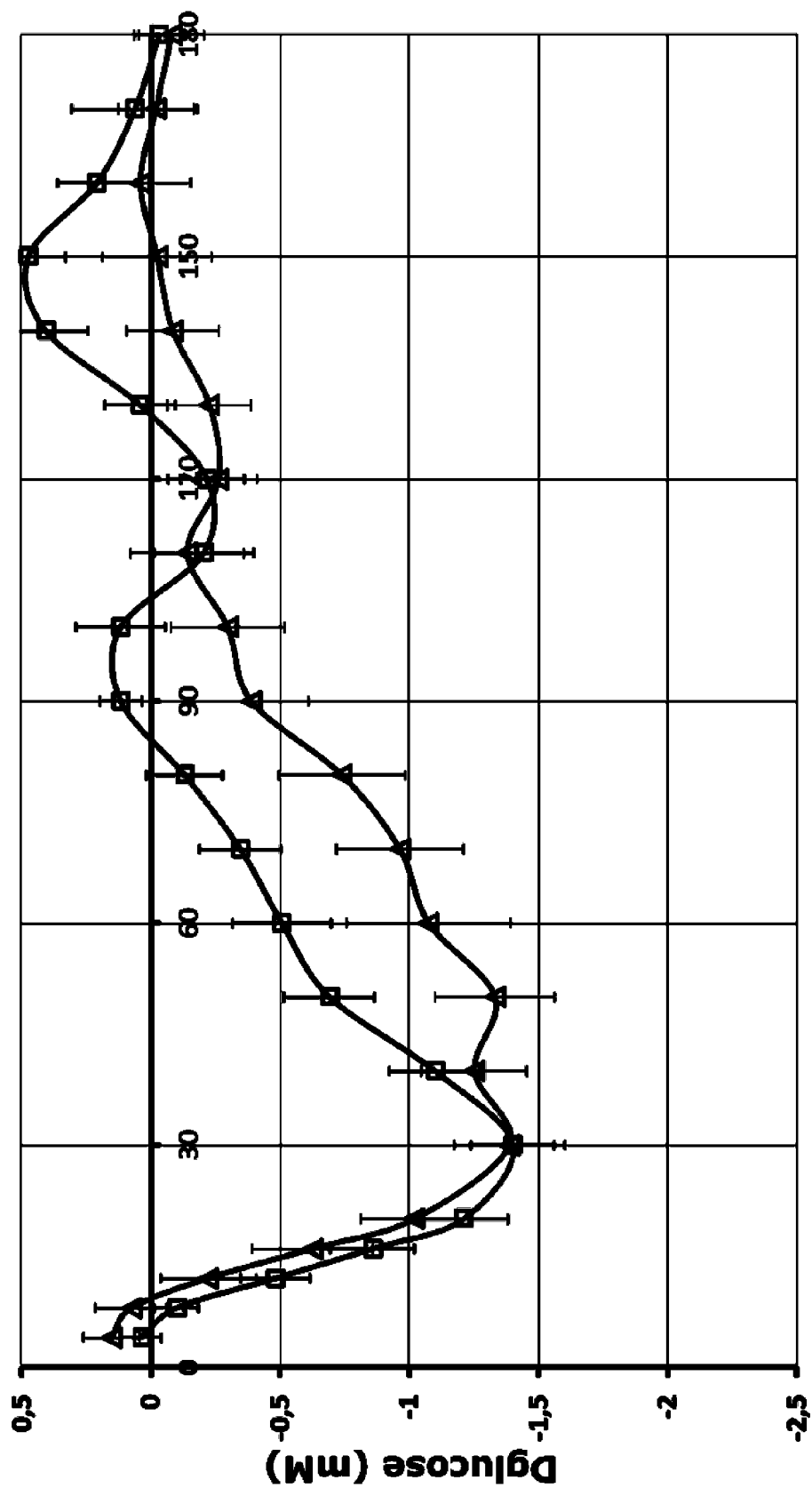
FIG. 15: the curves show that the formulation based on insulin lispro (Humalog®) comprising oligosaccharide 2 and polyanionic compound 1 as excipients at 7.3 mg/mL (curve plotted with squares corresponding to example B13, Tmin glucose=32±12 min) has a more rapid action than that of the commercial formulation of insulin lispro (Humalog®) (curve plotted with triangles corresponding to example B2, Tmin glucose=44±14 min).

The results for pharmacodynamics obtained with the formulations described in examples B2 and B13 are presented in FIG. 15. Analysis of these curves shows that the formulation based on insulin lispro (Humalog®) comprising oligosaccharide 2 and polyanionic compound 1 as excipients at 7.3 mg/mL (curve plotted with squares corresponding to example B13, Tmin glucose=32±12 min) makes it possible to obtain a more rapid action than that of the commercial formulation of insulin lispro (Humalog®) (curve plotted with triangles corresponding to example B2, Tmin glucose=44±14 min).

Figure 16:
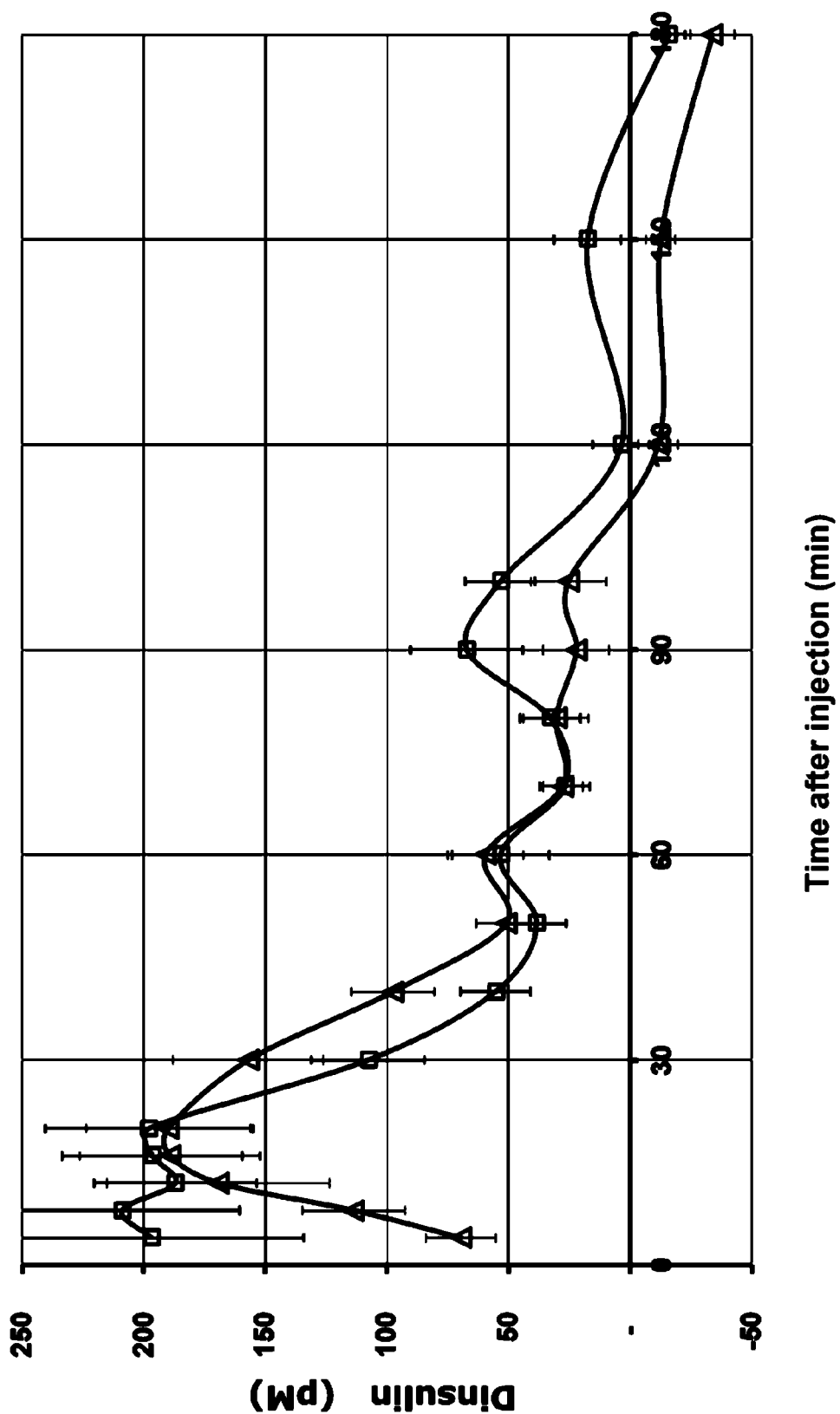
FIG. 16: the curves show that the formulation based on insulin lispro (Humalog®) comprising oligosaccharide 2 and polyanionic compound 1 as excipients at 7.3 mg/mL (curve plotted with squares corresponding to example B13, Tmax insulin=14±7 min) induces a more rapid absorption than the commercial formulation of insulin lispro Humalog®) (curve plotted with triangles corresponding to example B2, Tmax insulin=18±8 min).

The results for pharmacokinetics obtained with the formulations described in examples B2 and B13 are presented in FIG. 16. Analysis of these curves shows that the formulation based on insulin lispro (Humalog®) comprising oligosaccharide 2 and polyanionic compound 1 as excipients at 7.3 mg/mL (curve plotted with squares corresponding to example B13, Tmax insulin=14±7 min) induces a more rapid absorption than the commercial formulation of insulin lispro Humalog®) (curve plotted with triangles corresponding to example B2, Tmax insulin=18±8 min).

C10. Results for Pharmacodynamics and Pharmacokinetics of the Insulin Solutions from Examples B2 and B14.

| Example | Insulin | Oligosaccharide | Excipient | Dose IU/kg | Number of pigs |
|---|---|---|---|---|---|
| B2 | Lispro | — | — | 0.09 | 10 |
| B14 | Lispro | 2 | Polyanionic compound 1 14.6 mg/mL | 0.09 | 11 |

Figure 17:
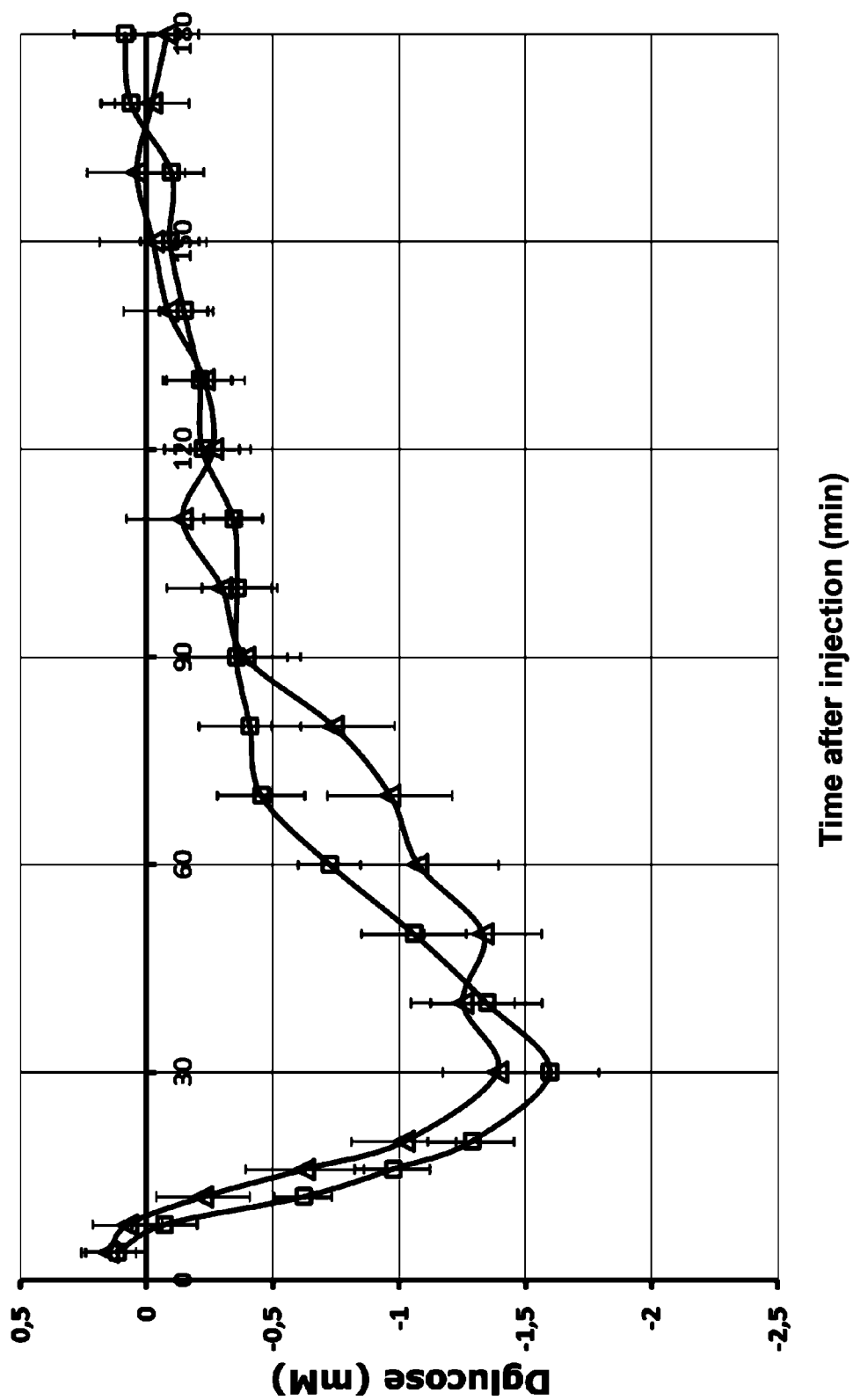
FIG. 17: the curves show that the formulation based on insulin lispro (Humalog®) comprising oligosaccharide 2 and polyanionic compound 1 as excipient at 14.6 mg/mL (curve plotted with squares corresponding to example B14, Tmin glucose=30±7 min) has a more rapid action than that of the commercial formulation of insulin lispro (Humalog®) (curve plotted with triangles corresponding to example B2, Tmin glucose=44±14 min).

The results for pharmacodynamics obtained with the formulations described in examples B2 and B14 are presented in FIG. 17. Analysis of these curves shows that the formulation based on insulin lispro (Humalog®) comprising oligosaccharide 2 and polyanionic compound 1 as excipient at 14.6 mg/mL (curve plotted with squares corresponding to example B14, Tmin glucose=30±7 min) makes it possible to obtain a more rapid action than that of the commercial formulation of insulin lispro (Humalog®) (curve plotted with triangles corresponding to example B2, Tmin glucose=44±14 min).

Figure 18:
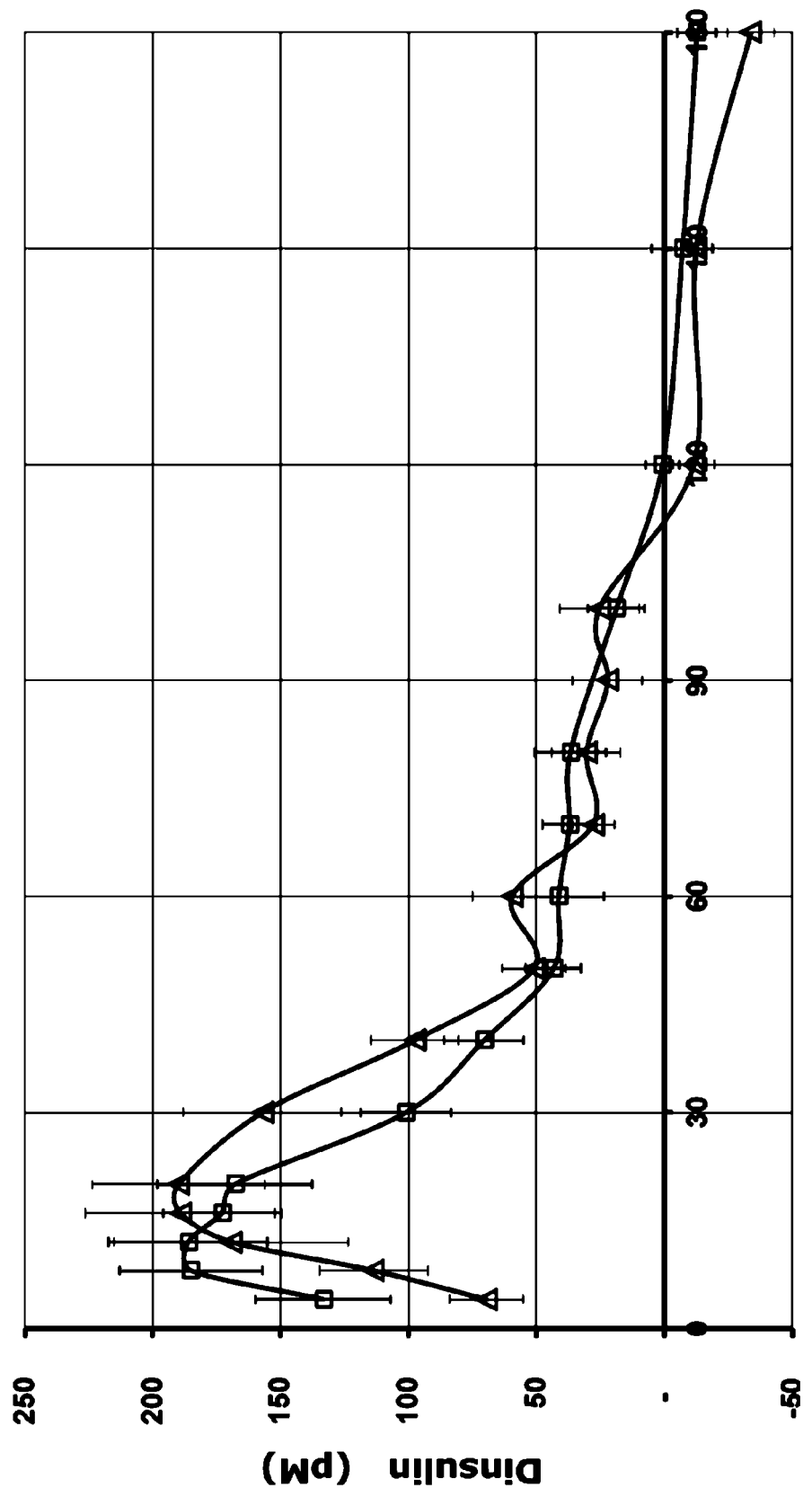
FIG. 18: the curves show that the formulation based on insulin lispro (Humalog®) comprising oligosaccharide 2 and polyanionic compound 1 as excipient at 14.6 mg/mL (curve plotted with squares corresponding to example B14, Tmax insulin=12±5 min) induces a more rapid absorption of Humalog® than the commercial formulation of insulin lispro (Humalog®) (curve plotted with triangles corresponding to example B2, Tmax insulin=18±8 min).

The results for pharmacokinetics obtained with the formulations described in examples B2 and B14 are presented in FIG. 18. Analysis of these curves shows that the formulation based on insulin lispro (Humalog®) comprising oligosaccharide 2 and polyanionic compound 1 as excipient at 14.6 mg/mL (curve plotted with squares corresponding to example B14, Tmax insulin=12±5 min) induces a more rapid absorption of Humalog® than the commercial formulation of insulin lispro (Humalog®) (curve plotted with triangles corresponding to example B2, Tmax insulin=18±8 min).

C11. Results for Pharmacodynamics and Pharmacokinetics of the Insulin Solutions from Examples B2 and B8.

| Example | Insulin | Oligosaccharide | Excipient | Dose IU/kg | Number of pigs |
|---|---|---|---|---|---|
| B2 | Lispro | — | — | 0.09 | 12 |
| B8 | Lispro | 6 | — | 0.09 | 12 |

Figure 19:
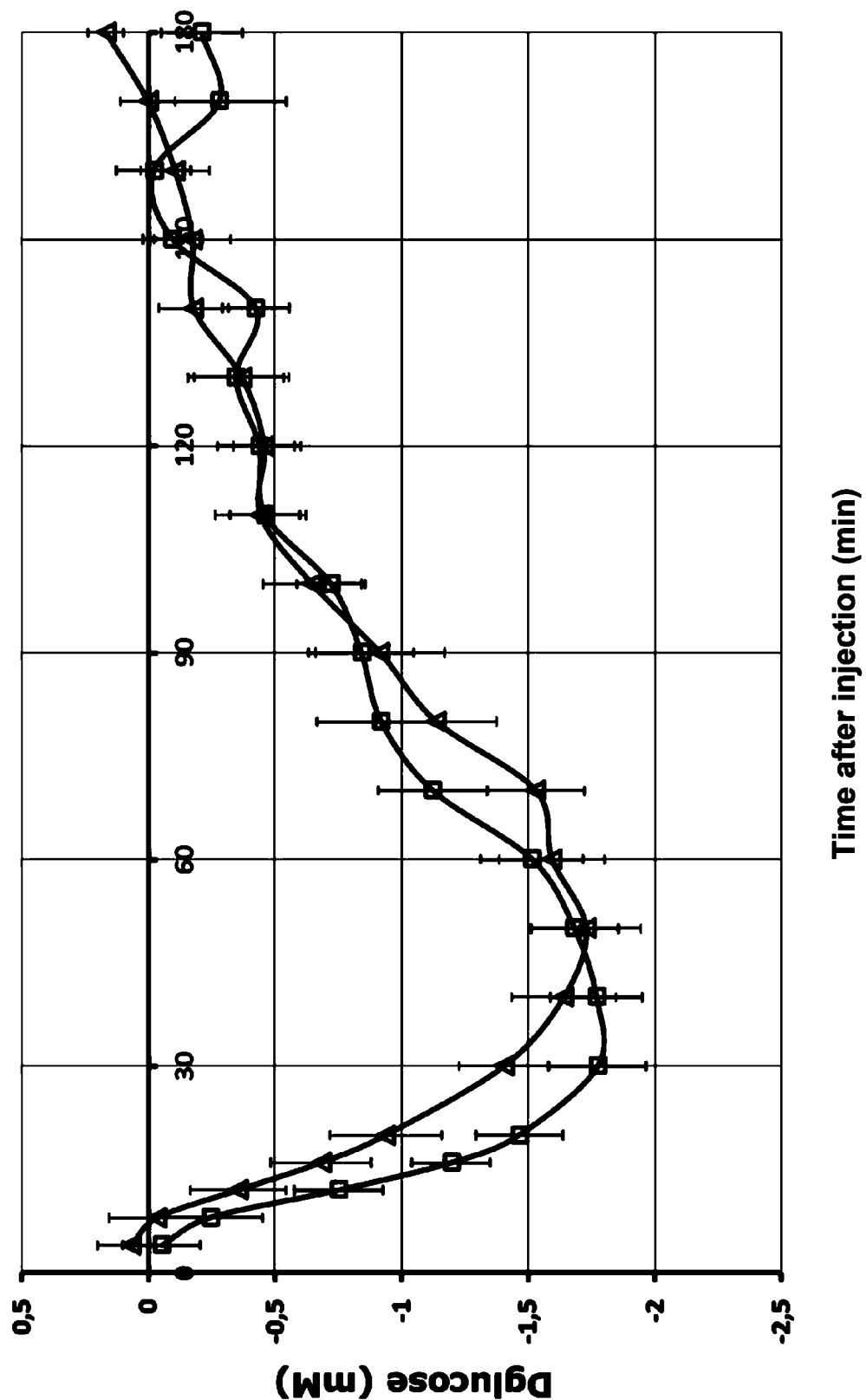
FIG. 19: the curves show that the formulation based on insulin lispro (Humalog®) comprising oligosaccharide 6 (curve plotted with squares corresponding to example B8, Tmin glucose=45±19 min) has not an action that is more rapid than that of the commercial formulation of insulin lispro (Humalog®) (curve plotted with triangles corresponding to example B2, Tmin glucose=50±14 min).

The results for pharmacodynamics obtained with the formulations described in examples B2 and B8 are presented in FIG. 19. Analysis of these curves shows that the formulation based on insulin lispro (Humalog®) comprising oligosaccharide 6 (curve plotted with squares corresponding to example B8, Tmin glucose=45±19 min) does not allow an action to be obtained that is more rapid than that of the commercial formulation of insulin lispro (Humalog®) (curve plotted with triangles corresponding to example B2, Tmin glucose=50±14 min).

Figure 20:
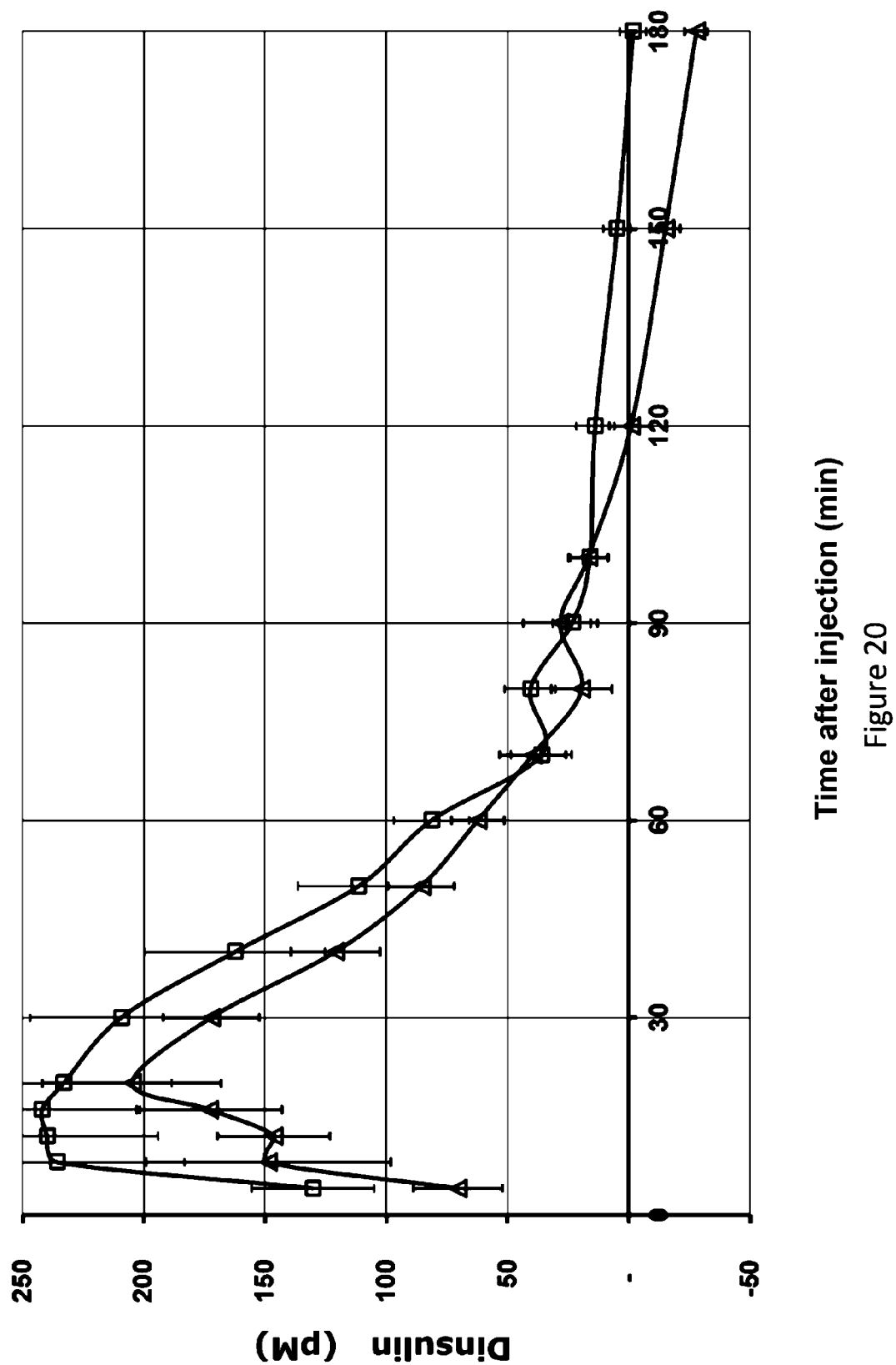
FIG. 20: the curves show that the formulation based on insulin lispro (Humalog®) comprising oligosaccharide 6 (curve plotted with squares corresponding to example B8, Tmax insulin=18±10 min) does not induce a more rapid absorption of Humalog® than the commercial formulation of insulin lispro (Humalog®) (curve plotted with triangles corresponding to example B2, Tmax insulin=20±9 min).

The results for pharmacokinetics obtained with the formulations described in examples B2 and B8 are presented in FIG. 20. Analysis of these curves shows that the formulation based on insulin lispro (Humalog®) comprising oligosaccharide 6 (curve plotted with squares corresponding to example B8, Tmax insulin=18±10 min) does not induce a more rapid absorption of Humalog® than the commercial formulation of insulin lispro (Humalog®) (curve plotted with triangles corresponding to example B2, Tmax insulin=20±9 min).

C12. Results for Pharmacodynamics and Pharmacokinetics of the Insulin Solutions from Examples B9 and B8.

| Example | Insulin | Oligosaccharide | Excipient | Dose IU/kg | Number of pigs |
|---|---|---|---|---|---|
| B9 | Lispro | 2 | Citrate 9.3 mM | 0.09 | 12 |
| B8 | Lispro | 6 | — | 0.09 | 12 |

Figure 21:
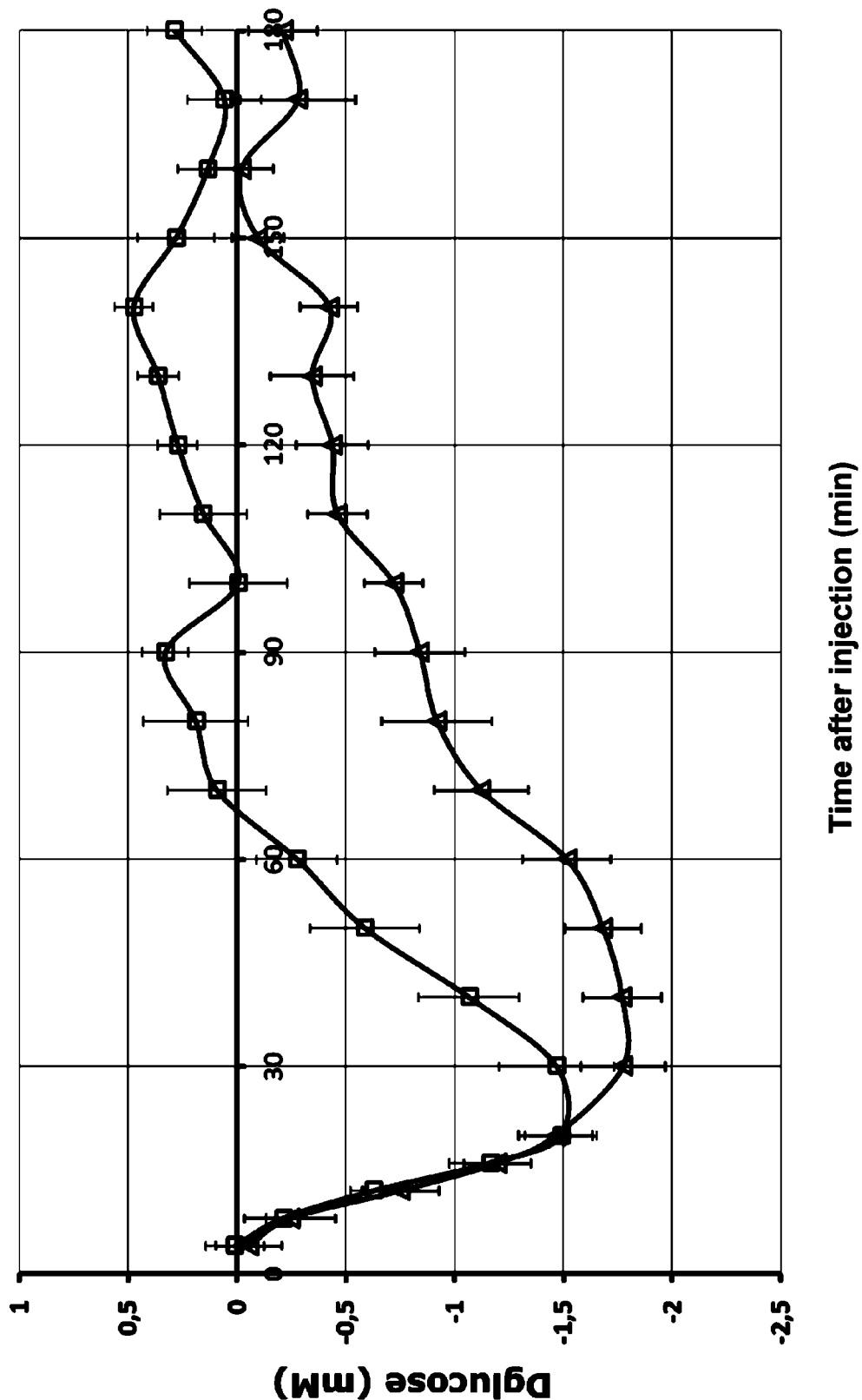
FIG. 21: the curves show that the formulation based on insulin lispro (Humalog®) comprising oligosaccharide 2 and citrate at 9.3 mM as excipient (curve plotted with squares corresponding to example B9, Tmin glucose=32±9 min) has a more rapid action than that of the formulation based on insulin lispro (Humalog®) comprising oligosaccharide 6 (curve plotted with triangles corresponding to example B8, Tmin glucose=45±19 min).

The results for pharmacodynamics obtained with the formulations described in examples B8 and B9 are presented in FIG. 21. Analysis of these curves shows that the formulation based on insulin lispro (Humalog®) comprising oligosaccharide 2 and citrate at 9.3 mM as excipient (curve plotted with squares corresponding to example B9, Tmin glucose=32±9 min) makes it possible to obtain a more rapid action than that of the formulation based on insulin lispro (Humalog®) comprising oligosaccharide 6 (curve plotted with triangles corresponding to example B8, Tmin glucose=45±19 min).

Figure 22:
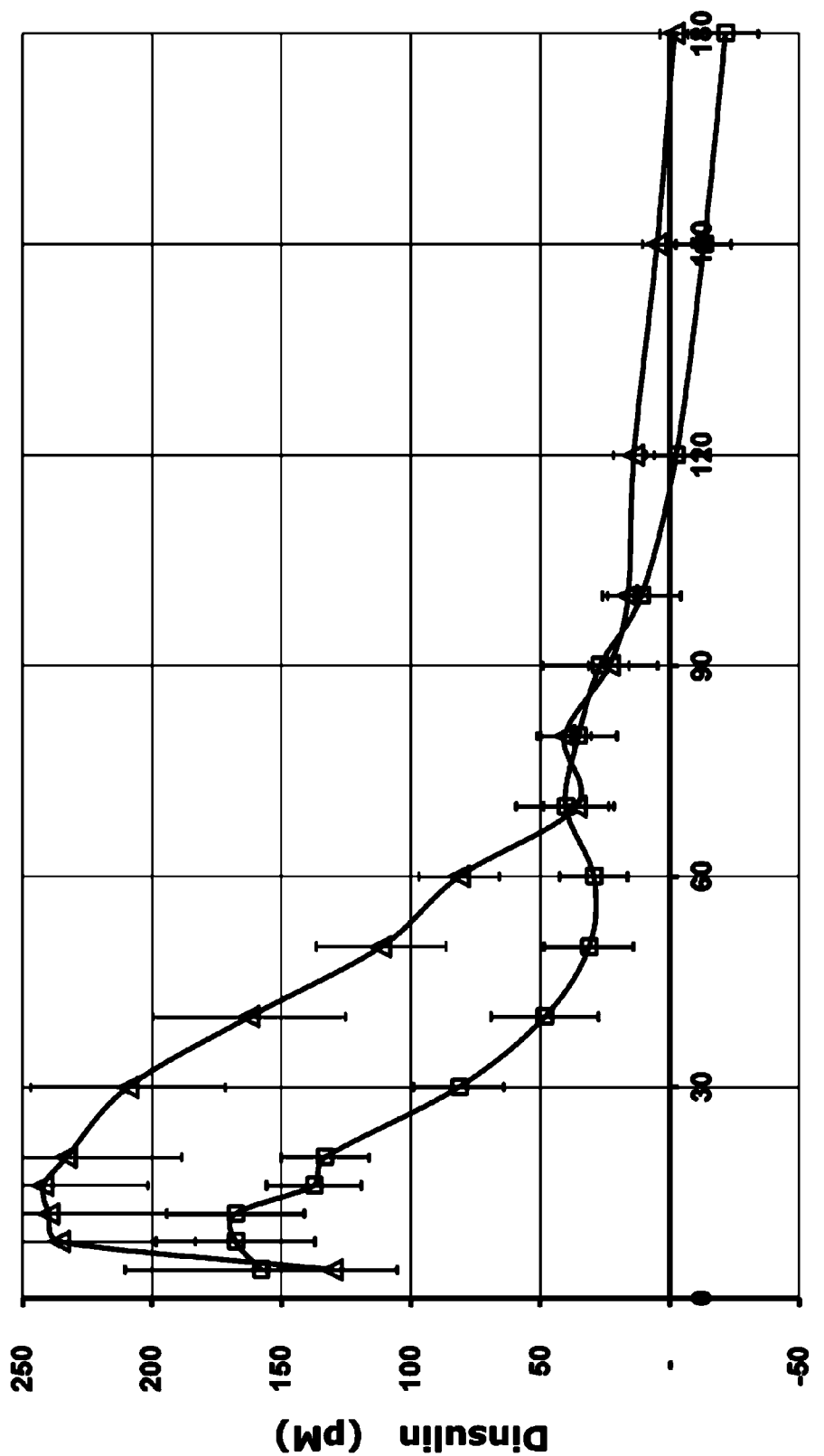
FIG. 22: the curves show that the formulation based on Humalog® comprising oligosaccharide 2 and citrate at 9.3 mM as excipient (curve plotted with squares corresponding to example B9, Tmax insulin=12±7 min) induces a more rapid absorption than the formulation based on insulin lispro (Humalog®) comprising oligosaccharide 6 (curve plotted with triangles corresponding to example B8, Tmax insulin=18±10 min).

The results for pharmacokinetics obtained with the formulations described in examples B8 and B9 are presented in FIG. 22. According to the invention, analysis of these curves shows that the formulation based on Humalog® comprising oligosaccharide 2 and citrate at 9.3 mM as excipient (curve plotted with squares corresponding to example B9, Tmax insulin=12±7 min) induces a more rapid absorption than the formulation based on insulin lispro (Humalog®) comprising oligosaccharide 6 (curve plotted with triangles corresponding to example B8, Tmax insulin=18±10 min).

C13. Results for Pharmacodynamics and Pharmacokinetics of the Insulin Solutions from Examples B2 and B15.

| Example | Insulin | Oligosaccharide | Excipient | Dose IU/kg | Number of pigs |
|---|---|---|---|---|---|
| B2 | Lispro | — | — | 0.09 | 12 |
| B15 | Lispro | 2 at 14.3 mg/mL | — | 0.09 | 12 |

Figure 23:
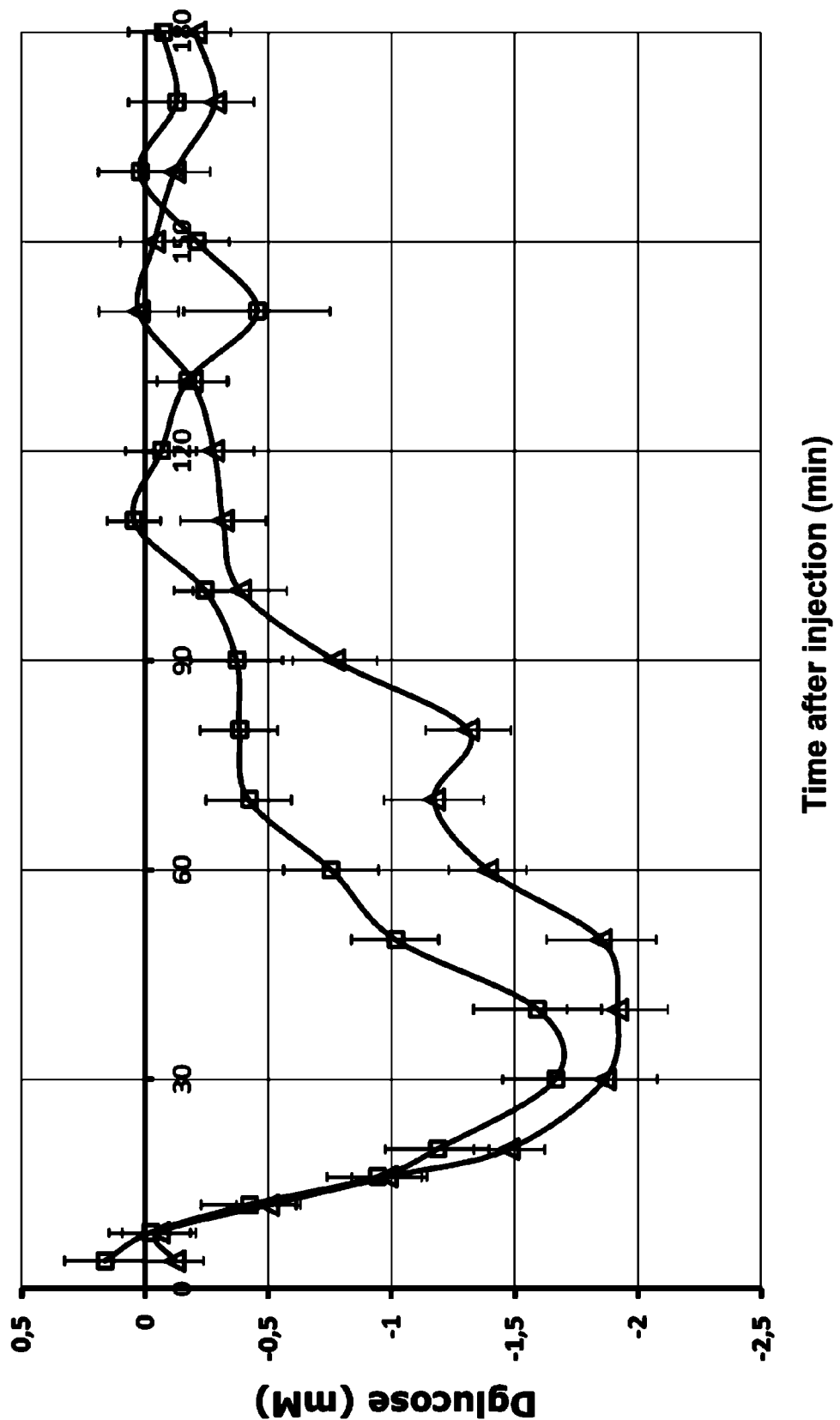
FIG. 23: the curves show that the formulation based on insulin lispro (Humalog®) comprising oligosaccharide 2 at 14.6 mg/mL (curve plotted with squares corresponding to example B15, Tmin glucose=35±5 min) has a more rapid action than that of the commercial formulation of insulin lispro (Humalog®) (curve plotted with triangles corresponding to example B2, Tmin glucose=47±18 min).

The results for pharmacodynamics obtained with the formulations described in examples B2 and B15 are presented in FIG. 23. Analysis of these curves shows that the formulation based on insulin lispro (Humalog®) comprising oligosaccharide 2 at 14.6 mg/mL (curve plotted with squares corresponding to example B15, Tmin glucose=35±5 min) makes it possible to obtain a more rapid action than that of the commercial formulation of insulin lispro (Humalog®) (curve plotted with triangles corresponding to example B2, Tmin glucose=47±18 min).

Figure 24:
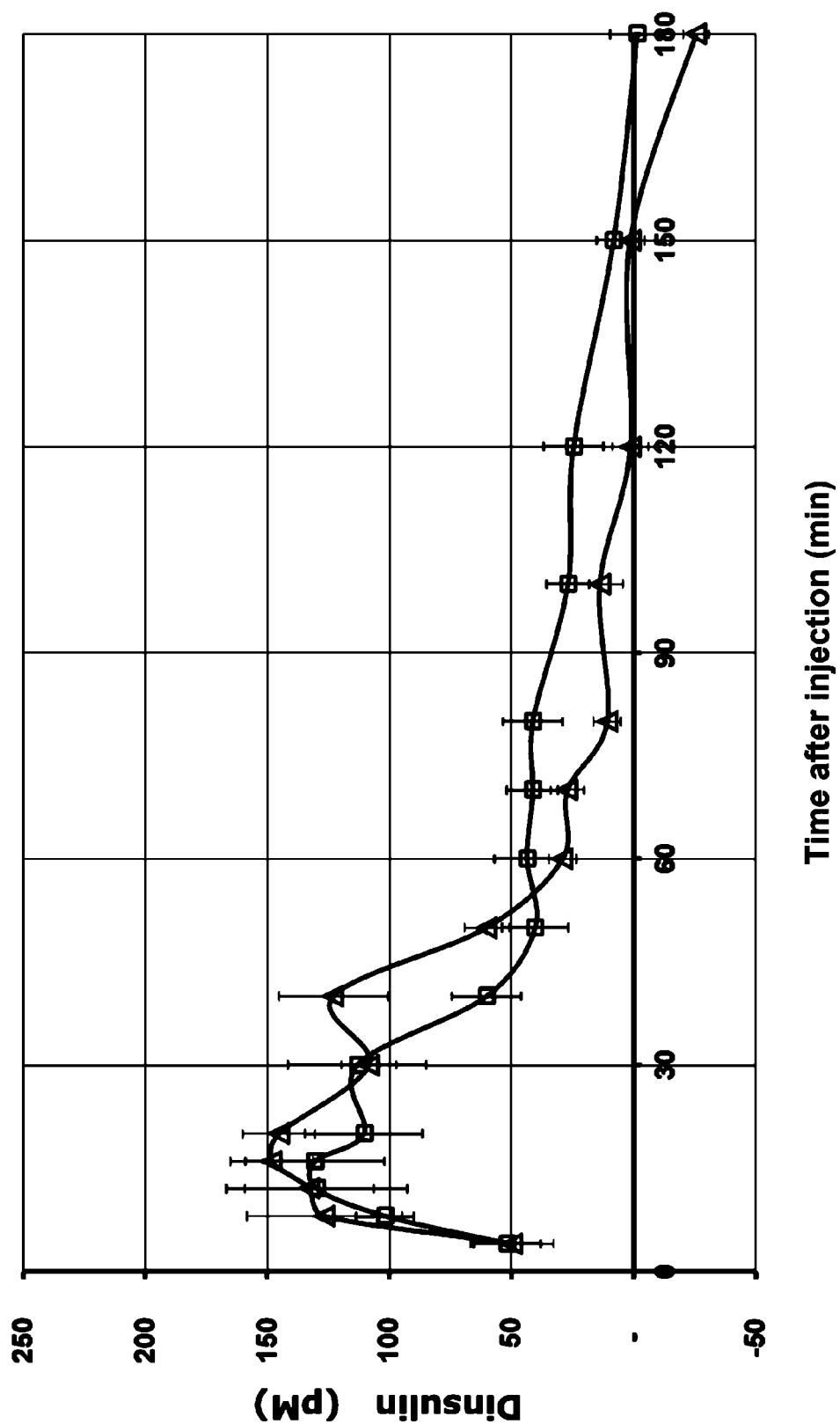
FIG. 24: the curves show that the formulation based on insulin lispro (Humalog®) comprising oligosaccharide 2 at 14.6 mg/Ml (curve plotted with squares corresponding to example B15, Tmax insulin=12±4 min) induces a more rapid absorption of Humalog® than the commercial formulation of insulin lispro (Humalog®) (curve plotted with triangles corresponding to example B2, Tmax insulin=20±11 min).

The results for pharmacokinetics obtained with the formulations described in examples B2 and B15 are presented in FIG. 24. Analysis of these curves shows that the formulation based on insulin lispro (Humalog®) comprising oligosaccharide 2 at 14.6 mg/Ml (curve plotted with squares corresponding to example B15, Tmax insulin=12±4 min) induces a more rapid absorption of Humalog® than the commercial formulation of insulin lispro (Humalog®) (curve plotted with triangles corresponding to example B2, Tmax insulin=20±11 min).

C14. Results for Pharmacodynamics and Pharmacokinetics of the Insulin Solutions from Examples B3 and B96

| Example | Insulin | Oligosaccharide | Excipient | Dose IU/kg | Number of pigs |
|---|---|---|---|---|---|
| B3 | Human | — | — | 0.125 | 10 |
| B96 | Human | 3 | — | 0.125 | 9 |

Figure 25:
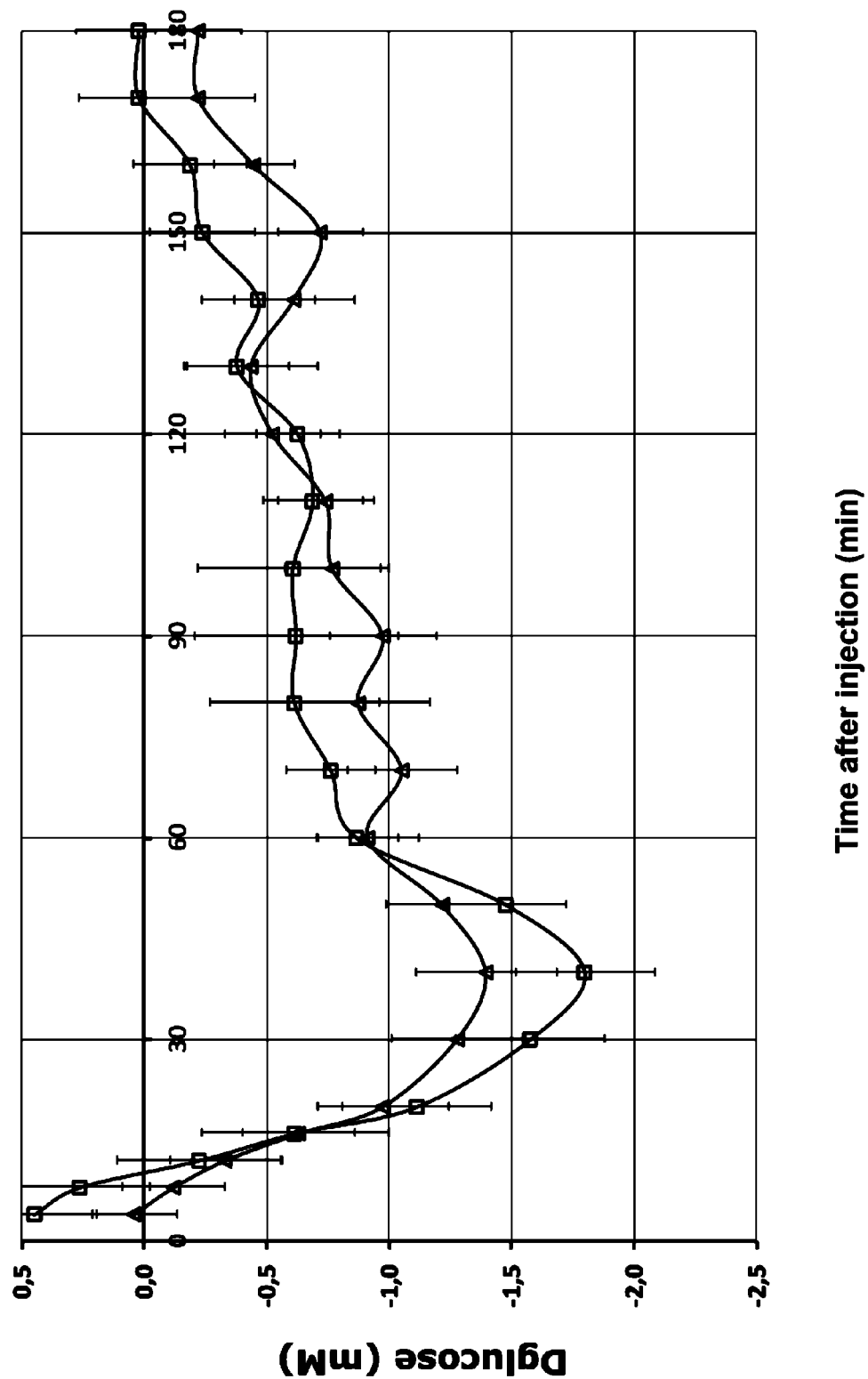
FIG. 25: the curves show that the formulation based on human insulin comprising oligosaccharide 3 as excipient at 7.3 mg/mL (curve plotted with squares corresponding to example B96, Tmin glucose=46±20 min) has a more rapid action than that of the commercial formulation of human insulin (curve plotted with triangles corresponding to example B3, Tmin glucose=64±33 min).

The results for pharmacodynamics obtained with the formulations described in examples B3 and B96 are presented in FIG. 25. Analysis of these curves shows that the formulation based on human insulin comprising oligosaccharide 3 as excipient at 7.3 mg/mL (curve plotted with squares corresponding to example B96, Tmin glucose=46±20 min) makes it possible to obtain a more rapid action than that of the commercial formulation of human insulin (curve plotted with triangles corresponding to example B3, Tmin glucose=64±33 min).

Figure 26:
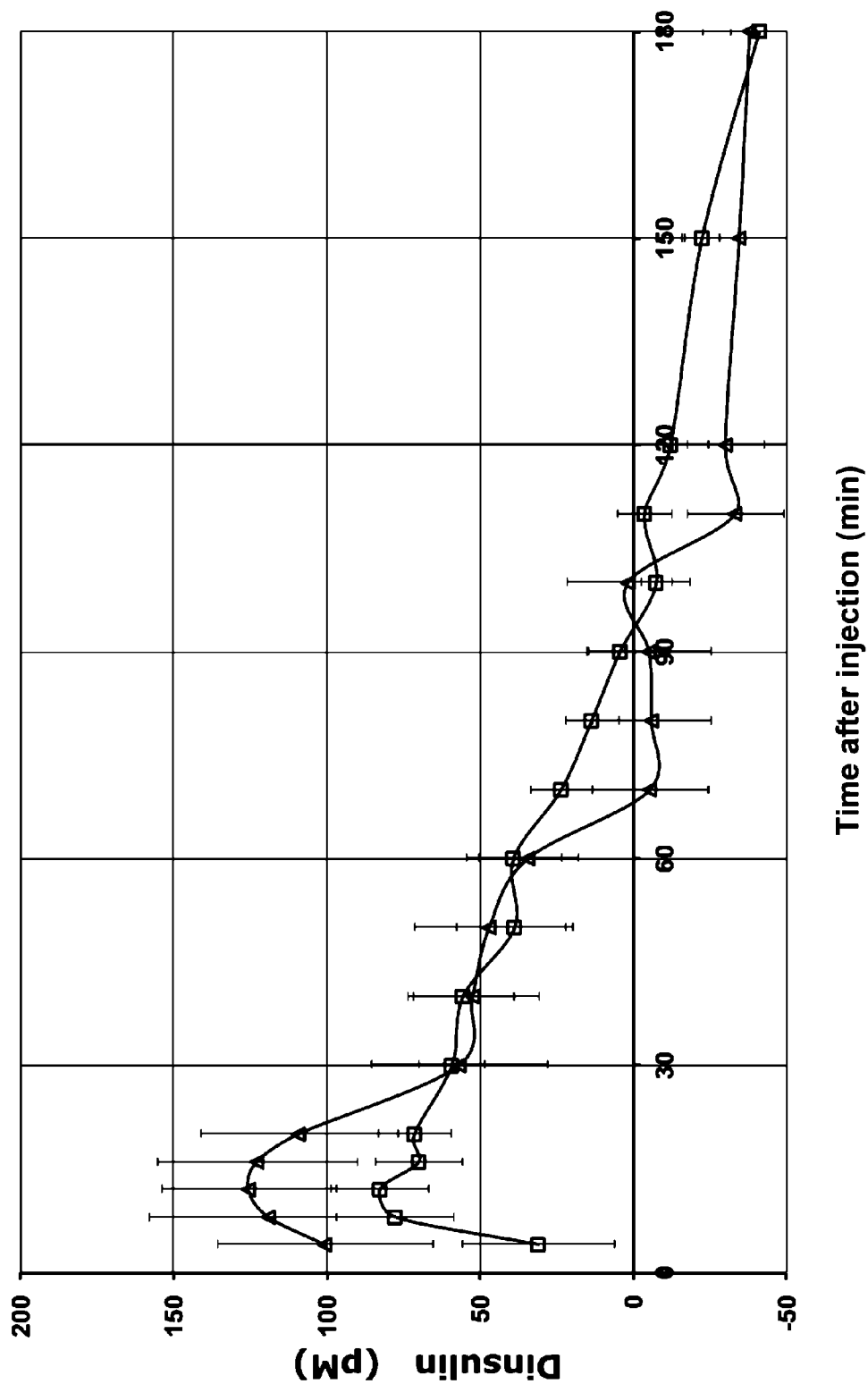
FIG. 26: the curves shows that the formulation based on human insulin comprising oligosaccharide 3 as excipient at 7.3 mg/mL (curve plotted with squares corresponding to example B96, Tmax insulin=12±6 min) induces an absorption that is more rapid than the commercial formulation of human insulin (curve plotted with triangles corresponding to example B3, Tmax insulin=26±20 min).

The results for pharmacokinetics obtained with the formulations described in examples B3 and B96 are presented in FIG. 26. Analysis of these curves shows that the formulation based on human insulin comprising oligosaccharide 3 as excipient at 7.3 mg/mL (curve plotted with squares corresponding to example B96, Tmax insulin=12±6 min) induces an absorption that is more rapid than the commercial formulation of human insulin (curve plotted with triangles corresponding to example B3, Tmax insulin=26±20 min).

D Circular Dichroism

D1. State of Association of Insulin Lispro (Humalog®) by Circular Dichroism (CD) in the Presence of Oligosaccharides Circular dichroism makes it possible to study the secondary and quaternary structure of insulin. The insulin monomers organize into dimers and hexamers. The hexamer is the form of insulin that is the most stable physically and chemically. There are two hexameric forms, form R6 and form T6. Insulin lispro has a strong CD signal at 251 nm characteristic of the hexameric form R6 (the most stable form). Loss of the CD signal at 251 nm is connected with destabilization of the hexamer (and therefore the first sign of transformation of the hexamer to dimer).

Figure 27:
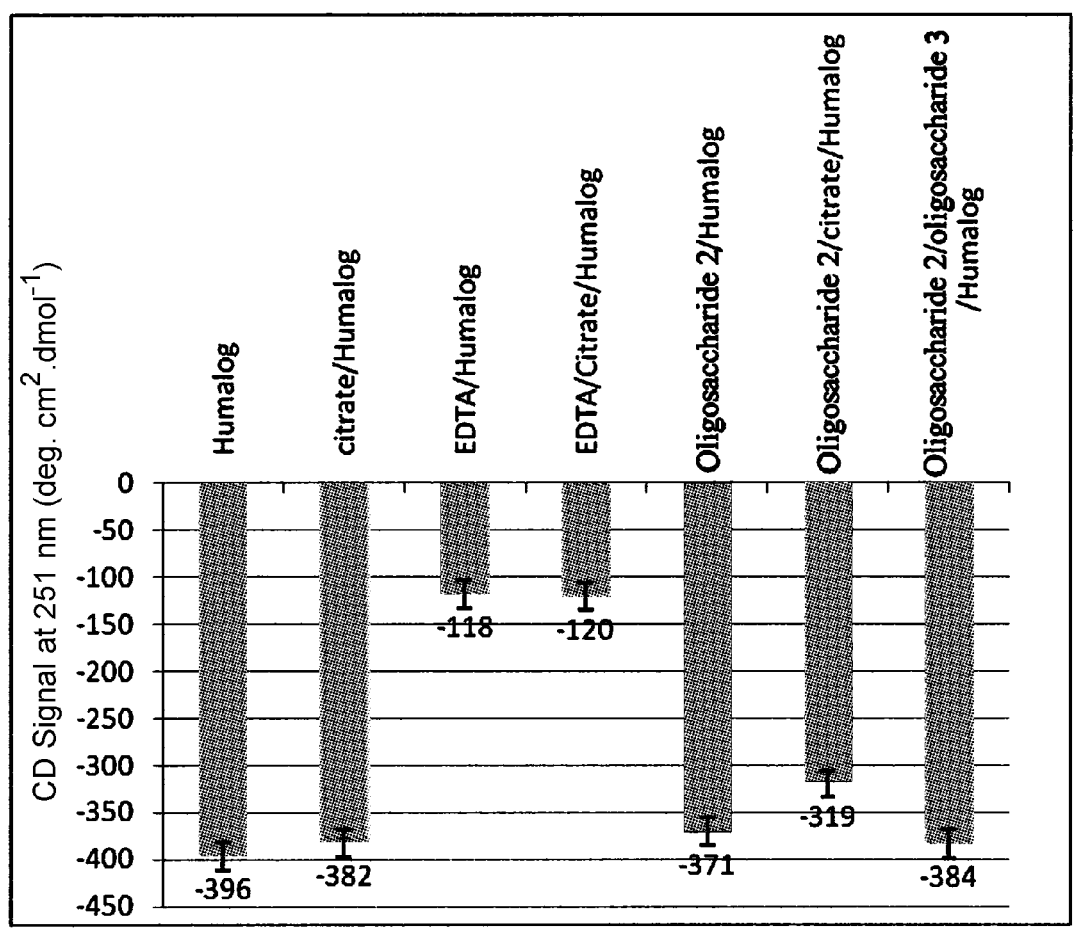
FIG. 27: Bar charts representing CD signals at 251 nm (deg·cm2·dmol-1) intensities of (from left to right) Humalog®, Citrate/Humalog®, EDTA/Humalog®, EDTA/Citrate/Humalog®, Oligosaccharide 2/Citrate/Humalog® and Oligosaccharide 2/Oligosaccharide 3/Humalog® formulations. The charts show that EDTA and the EDTA/citrate mixture completely destructures the R6 form of insulin lispro (Humalog®). EDTA therefore has a marked effect of destabilization of the hexamer. In contrast, the citrate alone, oligosaccharide 2 alone as well as the oligosaccharide 2/citrate mixture have almost no effect on the CD signal at 251 nm. These compounds therefore have hardly any impact on the R6 structure of the hexamer and especially on the hexameric structure of insulin, in contrast to EDTA, which destabilizes the hexamer.

EDTA and the EDTA/citrate mixture completely destructures the R6 form of insulin lispro (FIG. 27). EDTA therefore has a marked effect of destabilization of the hexamer. In contrast, the citrate alone, oligosaccharide 2 alone as well as the oligosaccharide 2/citrate mixture have almost no effect on the CD signal at 251 nm. These compounds therefore have hardly any impact on the R6 structure of the hexamer and especially on the hexameric structure of insulin, in contrast to EDTA, which destabilizes the hexamer.

D2. State of Association of Human Insulin by Circular Dichroism (CD) in the Presence of Oligosaccharides The CD signal at 276 nm (in the absence of m-cresol) is characteristic of the hexameric form of human insulin (signal of the hexamer around −300 nm, signal of the dimer between −200 nm and −250 nm and signal of the monomer below −200). Loss of the CD signal at 276 nm is therefore characteristic of destabilization of the hexamer to dimers or monomers.

Figure 28:
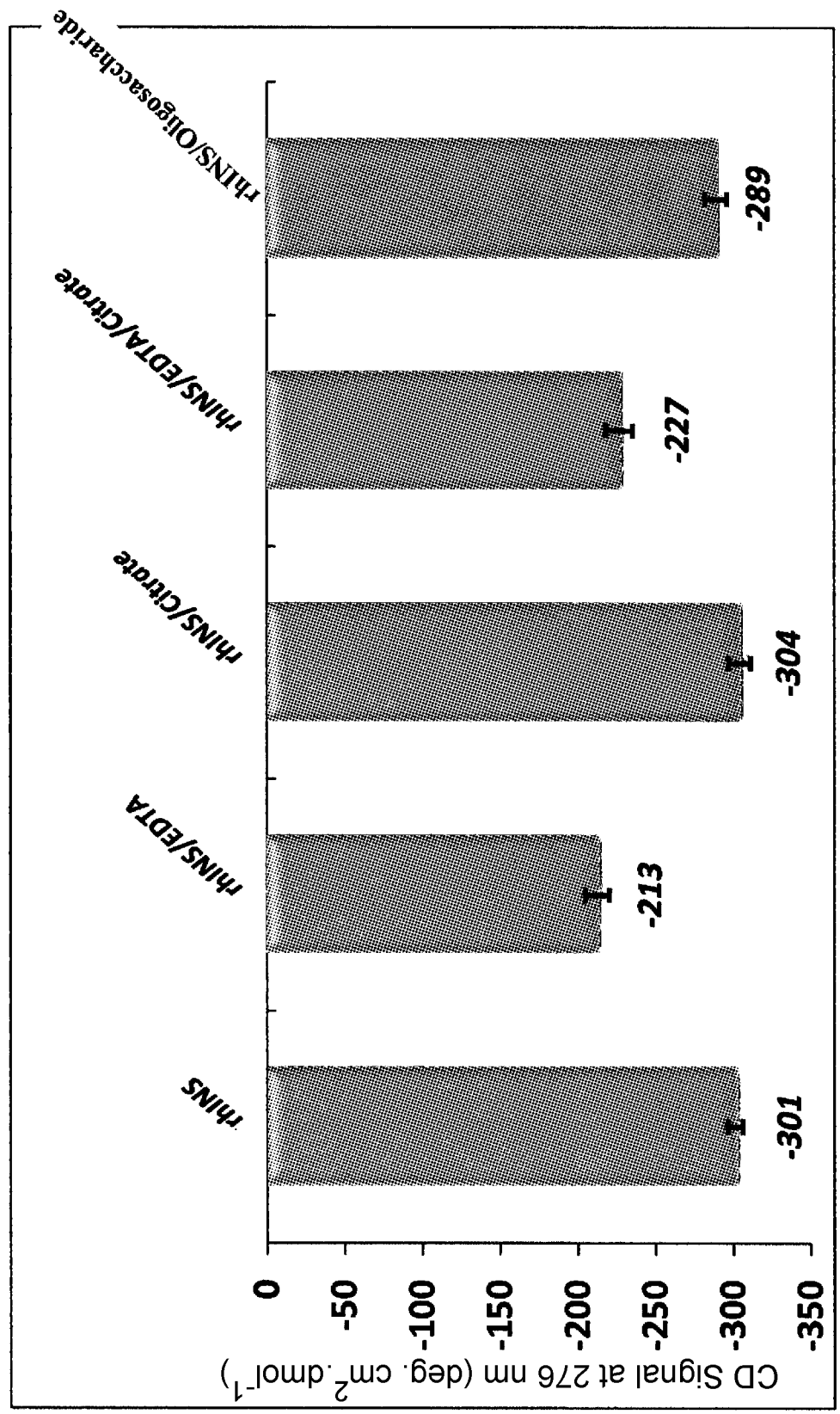
FIG. 28: Bar charts representing CD signals at 276 nm (deg·cm2·dmol-1) intensities of (from left to right) rhINS, rhINS/EDTA, rhINS/Citrate, rhINS/EDTA/Citrate and rhINS/Oligosaccharide 1 formulations. The bar charts show that EDTA and the EDTA/Citrate combination have a very marked effect on the hexameric structure of human insulin (complete dissociation of the hexamer to dimers). Conversely, oligosaccharide 1 does not have a significant effect on the hexameric structure of human insulin. In contrast to EDTA, the formulations based on oligosaccharide 1 do not dissociate the hexamer of human insulin.

EDTA and the EDTA/citrate combination have a very marked effect on the hexameric structure of human insulin (complete dissociation of the hexamer to dimers, FIG. 28). Conversely, oligosaccharide 1 does not have a significant effect on the hexameric structure of human insulin. In contrast to EDTA, the formulations based on oligosaccharide 1 do not dissociate the hexamer of human insulin.

E Dissolution of Human Insulin and Insulin Analog at the Isoelectric Point

E1. Dissolution of Human Insulin at its Isoelectric Point

Human insulin has an isoelectric point at 5.3. At this pH, human insulin is precipitated. A test demonstrating the formation of a complex of human insulin with the various oligosaccharides or polysaccharides is carried out at the isoelectric point. If interaction exists, it is possible to dissolve the insulin at its isoelectric point.

A solution of human insulin at 200 IU/mL is prepared. Solutions of oligosaccharides or of polysaccharides at different concentrations (8, 30 or 100 mg/mL) in water are prepared. An equivolume mixture (50/50) between the solution of insulin and the solution of oligosaccharide or of polysaccharide is effected to give a solution containing 100 UI/ML of human insulin and the desired concentration of polysaccharide (4, 15 or 50 mg/mL). The pH of the various solutions is adjusted to pH 5.3 by adding 200 mM acetic acid.

The appearance of the solution is documented. If the solution is cloudy, the oligosaccharide or the polysaccharide at the concentration tested does not allow dissolution of the insulin. If the solution is translucent, the oligosaccharide or the polysaccharide permits dissolution of the insulin at the concentration tested. In this way it is possible to determine the concentration of oligosaccharide or polysaccharide necessary for dissolving the insulin at its isoelectric point. The lower this concentration, the greater is the affinity of the oligosaccharide or of the polysaccharide for the insulin.

| Polysaccharide/Oligosaccharide | Dissolution of human insulin at 100 IU/mL by the polysaccharide/oligosaccharide at 4 mg/mL | Dissolution of human insulin at 100 IU/mL by the polysaccharide/oligosaccharide at 15 mg/mL | Dissolution of human insulin at 100 IU/mL by the polysaccharide/oligosaccharide at 50 mg/mL |
|---|---|---|---|
| Counterexamples | | | |
| Polysaccharide 1 | Yes | Yes | Yes |
| Polysaccharide 4 | Yes | Yes | Yes |
| Polysaccharide 3 | Yes | Yes | Yes |
| Polysaccharide 2 | Yes | Yes | Yes |
| Polysaccharide 5 | Yes | Yes | Yes |
| Examples | | | |
| Oligosaccharide 3 | No | Yes | Yes |
| Oligosaccharide 6 | No | Yes | Yes |
| Oligosaccharide 2 | No | Yes | Yes |
| Oligosaccharide 1 | No | No | No |
| Oligosaccharide 4 | No | No | No |

E2. Dissolution of Insulin Lispro at its Isoelectric Point

Insulin lispro has an isoelectric point at 5.3. At this pH, insulin lispro is precipitated. A test demonstrating the formation of a complex of insulin lispro with various oligosaccharides or polysaccharides is carried out at the isoelectric point. If interaction exists, it is possible to dissolve the insulin at its isoelectric point.

The commercial formulation of insulin lispro (Humalog®) is dialyzed against buffer PO4 1 mM (pH 7). After dialysis, the concentration of insulin lispro is about 90 IU/mL. The lyophilizate of oligosaccharide or of polysaccharide is weighed and dissolved in the solution of insulin lispro to give formulations containing insulin lispro at 90 IU/mL and the oligosaccharide or the polysaccharide at the desired concentrations (4, 15 or 50 mg/mL). The pH of the various solutions is adjusted to pH 5.3 by adding 200 mM acetic acid.

The appearance of the solution is documented. If the solution is cloudy, the oligosaccharide or the polysaccharide at the tested concentration does not allow dissolution of the insulin. If the solution is translucent, the oligosaccharide or the polysaccharide permits dissolution of the insulin at the concentration tested. In this way it is possible to determine the concentration of oligosaccharide or of polysaccharide necessary for dissolving the insulin at its isoelectric point. The lower this concentration, the greater is the affinity of the oligosaccharide or of the polysaccharide for the insulin.

| Polysaccharide/Oligosaccharide | Dissolution of insulin lispro at 90 IU/mL by the polysaccharide/oligosaccharide at 4 mg/mL | Dissolution of insulin lispro at 90 IU/mL by the polysaccharide/oligosaccharide at 15 mg/mL | Dissolution of insulin lispro at 90 IU/mL by the polysaccharide/oligosaccharide at 50 mg/mL |
|---|---|---|---|
| Counterexamples | | | |
| Polysaccharide 1 | Yes | Yes | Yes |
| Polysaccharide 3 | Yes | Yes | Yes |
| Polysaccharide 2 | Yes | Yes | Yes |
| Examples | | | |
| Oligosaccharide 3 | No | Yes | Yes |
| Oligosaccharide 6 | No | Yes | Yes |
| Oligosaccharide 2 | No | No | Yes |
| Oligosaccharide 1 | No | No | No |
| Oligosaccharide 4 | No | No | No |

F Interaction with Albumin

F1:

In order to determine the interactions between the various polysaccharides or oligosaccharides and a model protein such as albumin, a Centricon test (membrane with cutoff of 50 kD) was carried out. A solution of polysaccharide or of oligosaccharide at 7.3 mg/mL was diluted to one-third in a solution of BSA at 20 mg/mL in PBS (concentration in the mixture: 2.43 mg/mL of polymer, 13.3 mg/mL of albumin and about 100 mM of salt).

This mixture was centrifuged on the Centricon to cause about half of the volume to pass through the membrane. The albumin is retained quantitatively on the membrane of the Centricon. The polysaccharides and oligosaccharides analyzed largely pass through the membrane (for the polysaccharides with the highest molecular weights, about 20% of the polysaccharide is retained).

After centrifugation the polysaccharide or oligosaccharide is determined by UV in the filtrate. The percentage of BC bound to the albumin is calculated from the following equation:

[polysaccharide or oligosaccharide in the filtrate in the presence of albumin]/[polysaccharide or oligosaccharide in the filtrate in the absence of albumin]*100

It can be seen very clearly that the polysaccharides with molecular weight 5-15 kD are strongly retained by the albumin in this test. In contrast, the oligosaccharides of lower molecular weight 1-2 kD are retained far less by the albumin in this test.

| Polysaccharides/Oligosaccharides | % Polysaccharide/Oligosaccharide bound to the BSA |
|---|---|
| Counterexamples | |
| Polysaccharide 4 | 97% |
| Polysaccharide 1 | 95% |
| Polysaccharide 3 | 77% |
| Polysaccharide 5 | 86% |
| Polysaccharide 2 | 82% |
| Examples | |
| Oligosaccharide 4 | 27% |
| Oligosaccharide 1 | 34% |
| Oligosaccharide 2 | 48% |
| Oligosaccharide 3 | 45% |
| Oligosaccharide 6 | 51% |

What is claimed is:

1. A composition in aqueous solution, comprising insulin and at least one oligosaccharide whose average degree of polymerization is from 3 to 6 and whose polydispersity index (PDI) is above 1.0, said oligosaccharide having partially substituted carboxyl functional groups, the unsubstituted carboxyl functional groups being salifiable.

2. The composition as claimed in claim 1, wherein the composition further comprises at least one polyanionic compound.

3. The composition as claimed in claim 2, wherein the polyanionic compound is selected from the group consisting of anionic molecules; anionic polymers; and compounds consisting of a skeleton formed from a discrete number p, wherein $1 \leq p \leq 8$, of identical or different saccharide units, bound by identical or different glycosidic bonds that are naturally carriers of carboxyl groups or are substituted with carboxyl groups.

4. The composition as claimed in claim 1, wherein the composition is free of polyanionic compound.

5. The composition as claimed in claim 1, wherein the insulin is a human insulin.

6. The composition as claimed in claim 1, wherein the insulin is an insulin analog.

7. The composition as claimed in claim 6, wherein the insulin analog is selected from the group consisting of insulin lispro, insulin aspart and insulin glulisine.

8. The composition as claimed in claim 6, wherein the insulin analog is insulin lispro.

9. The composition as claimed in claim 1, wherein the oligosaccharide/insulin weight ratio is between 0.4 and 10.

10. The composition as claimed in claim 1, wherein the oligosaccharide is selected from the oligosaccharides of the following general formula I:

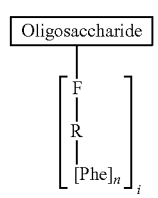

Formula I in which:
- the oligosaccharide is a dextran,
- F results from the coupling between linker arm R and an —OH of the oligosaccharide and being either an ester, carbamate or ether,
- R is a chain comprising between 1 and 15 carbons, optionally branched and/or unsaturated, comprising one or more heteroatoms, and having at least one carboxyl group,
- Phe is a residue of a phenylalanine derivative, of absolute configuration L or D, produced from coupling between the amine of the phenylalanine derivative and at least one acid carried by group R prior to attachment to Phe,
- n represents the mole fraction of R substituted with Phe and is between 0.3 and 0.9,
- i represents the average mole fraction of groups F—R—[Phe]n borne per saccharide unit and is between 0.5 and 2.5,
- when R is not substituted with Phe, the acid or acids of group R are carboxylates with an alkaline cation.

11. The composition as claimed in claim 10, wherein the composition is free of polyanionic compound.

12. A pharmaceutical formulation comprising a composition as claimed in claim 1.

13. The pharmaceutical formulation as claimed in claim 12, wherein the concentration of insulin is between 240 and 3000 µM or 40 to 500 IU/mL.

14. The pharmaceutical formulation as claimed in claim 12, wherein the concentration of insulin is between 600 and 1200 µM or 100 and 200 IU/mL.

15. A method for preparing a pharmaceutical formulation of insulin, comprising the step of mixing the insulin with at least one oligosaccharide whose average degree of polymerization is from 3 to 6 and whose polydispersity index (PDI) is above 1.0, wherein the method optionally comprises a step of adding a polyanionic compound to the formulation, and wherein after administration, the formulation accelerates the passage of insulin into the blood and reduces glycemia more rapidly relative to an oligosaccharide-free formulation.

16. The method as claimed in claim 15, wherein the oligosaccharide is selected from the oligosaccharides of the following general formula I:

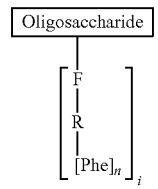

Formula I in which:
- the oligosaccharide is a dextran,
- F results from the coupling between linkage R and an —OH of the oligosaccharide and being either an ester, carbamate or ether,
- R is a chain comprising between 1 and 15 carbons, optionally branched and/or unsaturated, comprising one or more heteroatoms, and having at least one carboxyl group,
- Phe is a residue of a phenylalanine derivative, of absolute configuration L or D, produced from coupling between the amine of the phenylalanine derivative and at least one acid carried by group R prior to attachment to Phe,
- n represents the mole fraction of R substituted with Phe and is between 0.3 and 0.9,
- i represents the average mole fraction of groups F—R—[Phe]n borne per saccharide unit and is between 0.5 and 2.5,
- when R is not substituted with Phe, the acid or acids of group R are carboxylates with an alkaline cation.

17. The method as claimed in claim 15, wherein the polyanionic compound is selected from the group consisting of anionic molecules; anionic polymers; and compounds consisting of a skeleton formed from a discrete number p, wherein $1 \leq p \leq 8$, of identical or different saccharide units, bound by identical or different glycosidic bonds that are naturally carriers of carboxyl groups or are substituted with carboxyl groups.

18. The method as claimed in claim 15, wherein the method does not comprise the step of adding a polyanionic compound.

19. A method of preparing a formulation of human insulin having an insulin concentration between 240 and 3000 µM or 40 and 500 IU/mL, comprising the step of mixing the human insulin with at least one oligosaccharide whose average degree of polymerization is from 3 to 6 and whose polydispersity index (PDI) is above 1.0, wherein the method optionally comprises a step of adding at least one polyanionic compound to the formulation, and wherein onset of action of the formulation in humans is less than that of the reference formulation at the same insulin concentration in the absence of oligosaccharide.

20. The method as claimed in claim 19, wherein the method further comprises the step of adding at least one polyanionic compound to said formulation.

21. The method as claimed in claim 20, wherein the polyanionic compound is selected from the group consisting of anionic molecules; anionic polymers; and compounds consisting of a skeleton formed from a discrete number p, wherein $1 \leq p \leq 8$, of identical or different saccharide units, bound by identical or different glycosidic bonds that are naturally carriers of carboxyl groups or are substituted with carboxyl groups.

22. The method as claimed in claim 19, wherein the method does not comprise the step of adding a polyanionic compound to said formulation.

23. The method as claimed in claim 19, wherein the oligosaccharide is selected from the oligosaccharides of the following general formula I:

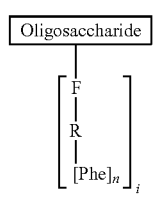

Formula I in which:
- the oligosaccharide is a dextran,
- F results from the coupling between linkage R and an —OH of the oligosaccharide and being either an ester, carbamate or ether,
- R is a chain comprising between 1 and 15 carbons, optionally branched and/or unsaturated, comprising one or more heteroatoms, and having at least one carboxyl group,
- Phe is a residue of a phenylalanine derivative, of absolute configuration L or D, produced from coupling between the amine of the phenylalanine derivative and at least one acid carried by group R prior to attachment to Phe,
- n represents the mole fraction of R substituted with Phe and is between 0.3 and 0.9,
- i represents the average mole fraction of groups F—R—[Phe]n borne per saccharide unit and is between 0.5 and 2.5,
- when R is not substituted with Phe, the acid or acids of group R are carboxylates with an alkaline cation.

24. A method of preparing a formulation of human insulin having an insulin concentration of 600 μM or 100 IU/mL, comprising the step of mixing the human insulin with at least one oligosaccharide whose average degree of polymerization is from 3 to 6 and whose polydispersity index (PDI) is above 1.0, wherein the method optionally comprises a step of adding at least one polyanionic compound to the formulation, and wherein onset of action of the formulation in humans is less than 60 minutes.

25. The method as claimed in claim 24, wherein the method further comprises the step of adding at least one polyanionic compound to said formulation.

26. The method as claimed in claim 24, wherein the method does not comprise the step of adding a polyanionic compound to said formulation.

27. A method of preparing a formulation of insulin analog having an insulin concentration between 240 and 3000 μM or 40 and 500 IU/mL, comprising the step of mixing the insulin analog with at least one oligosaccharide whose average degree of polymerization is from 3 to 6 and whose polydispersity index (PDI) is above 1.0, wherein the method optionally comprises a step of adding at least one polyanionic compound to the formulation, and wherein onset of action of the formulation in humans is less than that of the reference formulation at the same insulin concentration in the absence of oligosaccharide.

28. The method as claimed in claim 27, wherein the method further comprises the step of adding at least one polyanionic compound to said formulation.

29. The method as claimed in claim 27, wherein the method does not comprise the step of adding a polyanionic compound to said formulation.

30. A method of preparing a formulation of insulin analog having an insulin concentration of 600 μM or 100 IU/mL, comprising the step of mixing the insulin analog with at least one oligosaccharide whose average degree of polymerization is from 3 to 6 and whose polydispersity index (PDI) is above 1.0, wherein the method optionally comprises a step of adding at least one polyanionic compound to the formulation, and wherein onset of action of the formulation in humans is less than 30 minutes.

31. The method as claimed in claim 30, wherein the method further comprises the step of adding at least one polyanionic compound to said formulation.

32. The method as claimed in claim 30, wherein the method does not comprise the step of adding a polyanionic compound to said formulation.

\* \* \* \* \*